United States Patent
Ganeshalingam et al.

(10) Patent No.: US 9,215,162 B2
(45) Date of Patent: Dec. 15, 2015

(54) BIOLOGICAL DATA NETWORKS AND METHODS THEREFOR

(75) Inventors: Lawrence Ganeshalingam, Los Gatos, CA (US); Patrick Nikita Allen, Scotts Valley, CA (US)

(73) Assignee: Annai Systems Inc., Carlsbad, CA (US)

( * ) Notice: Subject to any disclaimer, the term of this patent is extended or adjusted under 35 U.S.C. 154(b) by 0 days.

(21) Appl. No.: 13/417,192

(22) Filed: Mar. 9, 2012

(65) Prior Publication Data

US 2012/0230339 A1    Sep. 13, 2012

Related U.S. Application Data

(60) Provisional application No. 61/451,086, filed on Mar. 9, 2011, provisional application No. 61/539,942, filed on Sep. 27, 2011, provisional application No. 61/539,931, filed on Sep. 27, 2011.

(51) Int. Cl.
  G06F 19/22    (2011.01)
  H04L 12/701   (2013.01)
  G06F 9/52     (2006.01)

(52) U.S. Cl.
  CPC .............. H04L 45/00 (2013.01); G06F 19/22 (2013.01); G06F 9/52 (2013.01); G06F 2209/484 (2013.01)

(58) Field of Classification Search
  CPC ......... H04L 45/00; G06F 19/16; G06F 19/18; G06F 19/22; G06F 9/52; G06F 2209/484
  See application file for complete search history.

(56) References Cited

U.S. PATENT DOCUMENTS

| | | |
|---|---|---|
| 5,668,810 A   | 9/1997  | Cannella |
| 6,119,120 A   | 9/2000  | Miller |
| 6,582,932 B1  | 6/2003  | Fukiage et al. |
| 6,920,396 B1* | 7/2005  | Wallace et al. ................. 702/19 |
| 7,158,892 B2  | 1/2007  | Robson et al. |
| 7,248,582 B2  | 7/2007  | Belgaied et al. |
| 7,292,709 B2  | 11/2007 | Imajo |
| 7,354,720 B2  | 4/2008  | Cuppoletti et al. |
| 7,359,379 B2  | 4/2008  | Jarabek et al. |
| 7,366,352 B2  | 4/2008  | Kravec et al. |
| 7,428,554 B1  | 9/2008  | Coberley et al. |
| 7,467,219 B2  | 12/2008 | Hodges et al. |

(Continued)

FOREIGN PATENT DOCUMENTS

| | | |
|---|---|---|
| EP | 0429201         | 5/1991 |
| KR | 1020070115964 A | 12/2007 |
| WO | WO 97-22076     | 6/1997 |
| WO | WO 2004-015579  | 2/2004 |
| WO | WO 2006-084391  | 8/2006 |
| WO | WO 2006/102128  | 9/2006 |

OTHER PUBLICATIONS

Office Action for U.S. Appl. No. 12/828,234, mailed on Mar. 13, 2013.

(Continued)

*Primary Examiner* — Xavier Wong
(74) *Attorney, Agent, or Firm* — Cooley LLP

(57) ABSTRACT

A system and method of transmitting and receiving information pertaining to biological sequence data is disclosed. The method includes receiving, at a network interface of a node of a network, a data packet including a first header containing network routing information and a second header associated with a layered model representative of the biological sequence data. The method also includes parsing the data packet and separating the first header from the second header.

25 Claims, 37 Drawing Sheets

(56) References Cited

U.S. PATENT DOCUMENTS

| | | | |
|---|---|---|---|
| 7,739,390 B2 | 6/2010 | Brahmbhatt et al. | |
| 7,820,378 B2 | 10/2010 | Van Den Boom et al. | |
| 7,856,317 B2 | 12/2010 | Schilling | |
| 7,885,969 B2 | 2/2011 | Natarajan et al. | |
| 7,996,876 B1 | 8/2011 | Everson et al. | |
| 8,412,462 B1 | 4/2013 | Ganeshalingam et al. | |
| 2002/0029113 A1 | 3/2002 | Wang et al. | |
| 2002/0103937 A1 | 8/2002 | Tillmann | |
| 2002/0111742 A1 | 8/2002 | Rocke et al. | |
| 2003/0039362 A1 | 2/2003 | Califano et al. | |
| 2003/0055824 A1 | 3/2003 | Califano et al. | |
| 2003/0082544 A1 | 5/2003 | Fors et al. | |
| 2003/0097227 A1 | 5/2003 | Bloch et al. | |
| 2003/0113756 A1 | 6/2003 | Mertz | |
| 2003/0224419 A1 | 12/2003 | Corcoran et al. | |
| 2003/0236393 A1 | 12/2003 | Trucksis | |
| 2004/0005558 A1 | 1/2004 | Anderson et al. | |
| 2004/0006433 A1 | 1/2004 | Robson et al. | |
| 2005/0049795 A1* | 3/2005 | Fikuda et al. | 702/20 |
| 2005/0053968 A1* | 3/2005 | Bharadwaj et al. | 435/6 |
| 2005/0060599 A1 | 3/2005 | Inami | |
| 2005/0075794 A1 | 4/2005 | Hoffman | |
| 2005/0119535 A1 | 6/2005 | Yanagihara | |
| 2005/0131649 A1 | 6/2005 | Larsen | |
| 2005/0164247 A1* | 7/2005 | Brunkow et al. | 435/6 |
| 2005/0267693 A1 | 12/2005 | Allard et al. | |
| 2005/0267971 A1 | 12/2005 | Fritz | |
| 2006/0285685 A1 | 12/2006 | Msezane | |
| 2007/0026406 A1 | 2/2007 | El Ghaoui | |
| 2007/0042372 A1 | 2/2007 | Arita | |
| 2007/0101154 A1 | 5/2007 | Bardsley et al. | |
| 2007/0168135 A1 | 7/2007 | Agarwal | |
| 2007/0190534 A1 | 8/2007 | Birch-Machin et al. | |
| 2007/0271604 A1 | 11/2007 | Webster et al. | |
| 2007/0288172 A1 | 12/2007 | Aronow et al. | |
| 2008/0016201 A1 | 1/2008 | Thompson | |
| 2008/0077607 A1 | 3/2008 | Gatawood et al. | |
| 2008/0255877 A1 | 10/2008 | Fernandez | |
| 2008/0271053 A1 | 10/2008 | Kramer et al. | |
| 2008/0281818 A1* | 11/2008 | Tenenbaum et al. | 707/6 |
| 2009/0203986 A1 | 8/2009 | Winnick | |
| 2010/0014496 A1 | 1/2010 | Kalika et al. | |
| 2010/0050253 A1 | 2/2010 | Baughman | |
| 2010/0161607 A1 | 6/2010 | Singh | |
| 2010/0169107 A1 | 7/2010 | Ahn et al. | |
| 2010/0169313 A1 | 7/2010 | Kenedy et al. | |
| 2010/0169338 A1 | 7/2010 | Kenedy et al. | |
| 2010/0169340 A1 | 7/2010 | Kenedy et al. | |
| 2010/0262718 A1 | 10/2010 | Ikeno | |
| 2012/0047202 A1 | 2/2012 | Van Ackere et al. | |
| 2012/0089339 A1 | 4/2012 | Ganeshalingam et al. | |
| 2012/0089603 A1 | 4/2012 | Ganeshalingam et al. | |
| 2012/0089607 A1 | 4/2012 | Ganeshalingam et al. | |
| 2012/0089608 A1 | 4/2012 | Ganeshalingam et al. | |
| 2012/0089652 A1 | 4/2012 | Ganeshalingam et al. | |
| 2012/0095693 A1 | 4/2012 | Ganeshalingam et al. | |
| 2012/0230326 A1 | 9/2012 | Ganeshalingam et al. | |
| 2012/0230338 A1 | 9/2012 | Ganeshalingam et al. | |
| 2012/0232874 A1 | 9/2012 | Ganeshalingam et al. | |
| 2012/0233201 A1 | 9/2012 | Ganeshalingam et al. | |
| 2012/0233202 A1 | 9/2012 | Ganeshalingam et al. | |
| 2012/0236861 A1 | 9/2012 | Ganeshalingam et al. | |
| 2013/0246460 A1 | 9/2013 | Maltbie et al. | |
| 2014/0164515 A1 | 6/2014 | Maltbie et al. | |
| 2014/0164516 A1 | 6/2014 | Maltbie et al. | |

OTHER PUBLICATIONS

Office Action for U.S. Appl. No. 13/223,077, mailed on Nov. 20, 2012.
Office Action for U.S. Appl. No. 13/223,084, mailed on Feb. 7, 2013.
Office Action for U.S. Appl. No. 13/223,088, mailed on Jan. 2, 2013.
Office Action for U.S. Appl. No. 13/223,092, mailed Feb. 7, 2013.
Office Action for U.S. Appl. No. 13/223,097, mailed Nov. 16, 2012.
International Search Report and Written Opinion for PCT/US2011/050073 mailed Apr. 25, 2012.
International Search Report and Written Opinion for PCT/US2011/050075 mailed Apr. 25, 2012.
International Search Report and Written Opinion for PCT/US2011/050077 mailed Apr. 27, 2012.
International Search Report for PCT/US2011/050078, mailed on Mar. 21, 2012.
Written Opinion for PCT/US2011/050078, mailed on Mar. 21, 2012.
International Search Report and Written Opinion for PCT/US2011/050079 mailed Apr. 9, 2012.
International Search Report and Written Opinion for PCT/US2011/050080 mailed May 1, 2012.
International Search Report for PCT/US2012/028642, mailed on Oct. 23, 2012.
International Search Report for PCT/US2012/028643, mailed Sep. 3, 2012.
International Search Report for PCT/US2012/028644, mailed Sep. 3, 2012.
International Search Report for PCT/US2012/028645, mailed Sep. 3, 2012.
International Search Report for PCT/US2012/028647, mailed Sep. 26, 2012.
International Search Report for PCT/US2012/028650, mailed Sep. 27, 2012.
International Search Report for PCT/US2012/028652, mailed Oct. 23, 2012.
International Search Report for PCT/US2012/057668, mailed Jan. 17, 2013.
Calabretta, et al., "Optical Signal Processing Based on Self-Induced Polarization Rotation in a Semiconductor Optical Amplifier"; Journal of Lightwave Technology, 22(2) Feb. 2004.
Tanebaum, et al., "The JCVI Standard Operating Procedure for Annotating Prokaryotic Metagenmic Shotgun Sequencing Data", Standards in Genomic Sciences, 2(2):229-237 (2010).
International Search Report for PCT/US2012/028642, mailed Sep. 19, 2013.
International Search Report for PCT/US2012/028643, mailed Sep. 19, 2013.
International Search Report for PCT/US2012/028644, mailed Sep. 19, 2013.
International Search Report for PCT/US2012/028645, mailed Sep. 19, 2013.
International Search Report for PCT/US2012/028647, mailed Sep. 19, 2013.
International Search Report for PCT/US2012/028650, mailed Sep. 19, 2013.
International Search Report for PCT/US2012/028652, mailed Sep. 19, 2013.
Office Action for U.S. Appl. No. 13/417,193, mailed May 23, 2013.
Office Action for U.S. Appl. No. 13/223,071, mailed Jun. 5, 2014.
Office Action for U.S. Appl. No. 13/223,071, mailed Nov. 13, 2013.
Office Action for U.S. Appl. No. 13/223,084, mailed Aug. 6, 2014.
Office Action for U.S. Appl. No. 13/223,084, mailed May 12, 2014.
Office Action for U.S. Appl. No. 13/223,084, mailed Sep. 27, 2013.
Office Action for U.S. Appl. No. 13/223,092, mailed Jun. 25, 2014.
Office Action for U.S. Appl. No. 13/223,092, mailed May 12, 2014.
Office Action for U.S. Appl. No. 13/223,092, mailed Sep. 6, 2013.
Office Action for U.S. Appl. No. 13/223,097, mailed Jun. 5, 2014.
Office Action for U.S. Appl. No. 13/223,097, mailed Sep. 18, 2013.
Office Action for U.S. Appl. No. 13/290,992, mailed Sep. 13, 2013.
Office Action for U.S. Appl. No. 13/417,184, mailed Jun. 16, 2014.
Office Action for U.S. Appl. No. 13/417,184, mailed Nov. 26, 2013.
Office Action for U.S. Appl. No. 13/417,187, mailed May 21, 2014.
Office Action for U.S. Appl. No. 13/417,188, mailed May 29, 2014.
Office Action for U.S. Appl. No. 13/417,188, mailed Nov. 4, 2013.
Office Action for U.S. Appl. No. 13/417,189, mailed May 27, 2014.
Office Action for U.S. Appl. No. 13/417,189, mailed Nov. 4, 2013.
Office Action for U.S. Appl. No. 13/417,190, mailed Nov. 29, 2013.
Office Action for U.S. Appl. No. 13/417,193, mailed Feb. 13, 2014.
International Search Report and Written Opinion for International Application No. PCT/US2013/047438, mailed Nov. 1, 2013.

(56) References Cited

OTHER PUBLICATIONS

Networking Tutorial, The CTDP Networking Guide, Version 0.6.3 (Feb. 3, 2001), pp. 1-149.
http://data.microarrays.ca/cpg/index.htm, Jan. 2006.
PCT/US011/050078 International Search Report mailed Mar. 21, 2012.
U.S. Appl. No. 12/837,452 (002/02)Non-Final Rejection mailed Apr. 5, 2012.
Notification of Transmittal of the International Search Report and the Written Opinion of the International Searching Authority, or the Declaration; and Written Opinion mailed Oct. 23, 2012 of PCT/US2012/028642.
Notification of Transmittal of the International Search Report and the Written Opinion of the International Searching Authority, or the Declaration; and Written Opinion mailed Sep. 3, 2012 of PCT/US2012/028643.
Notification of Transmittal of the International Search Report and the Written Opinion of the International Searching Authority, or the Declaration; and Written Opinion mailed Sep. 3, 2012 of PCT/US2012/028644.
Notification of Transmittal of the International Search Report and the Written Opinion of the International Searching Authority, or the Declaration; and Written Opinion mailed Sep. 3, 2012 of PCT/US2012/028645.
Notification of Transmittal of the International Search Report and the Written Opinion of the International Searching Authority, or the Declaration; and Written Opinion mailed Sep. 3, 2012 of PCT/US2012/028647.
Notification of Transmittal of the International Search Report and the Written Opinion of the International Searching Authority, or the Declaration; and Written Opinion mailed Sep. 27, 2012 of PCT/US2012/028650.
Notification of Transmittal of the International Search Report and the Written Opinion of the International Searching Authority, or the Declaration; and Written Opinion mailed Oct. 23, 2012 of PCT/US2012/028652.
U.S. Appl. No. 12/828,234 (001/00) Non-Final Rejection mailed May 22, 2012.
U.S. Appl. No. 12/837,452 (002/02) Non-Final Rejection mailed Apr. 5, 2012.

* cited by examiner

Various data types that are processed at network nodes

Processing sequence variants at a network node

SEQUENCE LISTING

```
<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: Example sequence fragment

<400> SEQUENCE: 1
ggaggctagt tagtata                                                    17

<210> SEQ ID NO 2
<211> LENGTH: 66
<212> TYPE: DNA
<213> ORGANISM: Artificial Sequence
<220> FEATURE:
<223> OTHER INFORMATION: Example sequence fragment

<400> SEQUENCE: 2
agttgacacc tgtccacacg ttaaacaggt tccataagat tgtgccgtta aatactcagg      60
caatct                                                                66

<210> SEQ ID NO 3
<211> LENGTH: 16
<212> TYPE: DNA
<213> ORGANISM: Artificial Sequence
<220> FEATURE:
```

```
<223> OTHER INFORMATION: Example sequence fragment

<400> SEQUENCE: 3
ttaaacaggt tccata                                                    16
```

BIOLOGICAL DATA NETWORKS AND METHODS THEREFOR

CROSS-REFERENCE TO RELATED APPLICATIONS

The present application claims the benefit of priority under 35 U.S.C. §119(e) of U.S. Provisional Patent Application Ser. No. 61/451,086, entitled BIOLOGICAL DATA NETWORK, filed on Mar. 9, 2011, of U.S. Provisional Patent Application Ser. No. 61/539,942, entitled SYSTEM AND METHOD FOR SECURE, HIGHSPEED TRANSFER OF VERY LARGE FILES, filed Sep. 27, 2011, and of U.S. Provisional Patent Application Ser. No. 61/539,931, entitled SYSTEM AND METHOD FOR FACILITATING NETWORK-BASED TRANSACTIONS INVOLVING SEQUENCE DATA, filed Sep. 27, 2011, the content of each of which is hereby incorporated by reference herein in its entirety for all purposes. This application is related to U.S. Utility patent application Ser. No. 12/837,452, entitled METHODS AND SYSTEMS FOR PROCESSING GENOMIC DATA, filed on Jul. 15, 2010, which claims priority to U.S. Provisional Patent Application Ser. No. 61/358,854, entitled METHODS AND SYSTEMS FOR PROCESSING GENOMICS DATA, filed on Jun. 25, 2010, and to U.S. Utility patent application Ser. No. 12/828,234, entitled METHODS AND SYSTEMS FOR PROCESSING GENOMIC DATA, filed on Jun. 30, 2010, which claims priority to U.S. Provisional Patent Application Ser. No. 61/358,854, entitled METHODS AND SYSTEMS FOR PROCESSING GENOMICS DATA, filed on Jun. 25, 2010, the content of each of which is hereby incorporated by reference herein in its entirety for all purposes. This application is also related to U.S. Utility patent application Ser. No. 13/223,077, entitled METHODS AND SYSTEMS FOR PROCESSING POLYMERIC SEQUENCE DATA AND RELATED INFORMATION, filed on Aug. 31, 2011, and to U.S. Utility patent application Ser. No. 13/223,084, entitled METHODS AND SYSTEMS FOR PROCESSING POLYMERIC SEQUENCE DATA AND RELATED INFORMATION, filed on Aug. 31, 2011, and to U.S. Utility patent application Ser. No. 13/223,088, entitled METHODS AND SYSTEMS FOR PROCESSING POLYMERIC SEQUENCE DATA AND RELATED INFORMATION, filed on Aug. 31, 2011, and to U.S. Utility patent application Ser. No. 13/223,092, entitled METHODS AND SYSTEMS FOR PROCESSING POLYMERIC SEQUENCE DATA AND RELATED INFORMATION, filed on Aug. 31, 2011, and to U.S. Utility patent application Ser. No. 13/223,097, entitled METHODS AND SYSTEMS FOR PROCESSING POLYMERIC SEQUENCE DATA AND RELATED INFORMATION, filed on Aug. 31, 2011, the content of each of which is hereby incorporated by reference herein in its entirety for all purposes. This application is also related to U.S. Utility patent application Ser. No. 13/417,184, entitled BIOLOGICAL DATA NETWORKS AND METHODS THEREFOR, filed on Mar. 9, 2012, and to U.S. Utility patent application Ser. No. 13/417,187, entitled BIOLOGICAL DATA NETWORKS AND METHODS THEREFOR, filed on Mar. 9, 2012, and to U.S. Utility patent application Ser. No. 13/417,188, entitled BIOLOGICAL DATA NETWORKS AND METHODS THEREFOR, filed on Mar. 9, 2012, and to U.S. Utility patent application Ser. No. 13/417,189, entitled BIOLOGICAL DATA NETWORKS AND METHODS THEREFOR, filed on Mar. 9, 2012, and to U.S. Utility patent application Ser. No. 13/417,190, entitled BIOLOGICAL DATA NETWORKS AND METHODS THEREFOR, filed on Mar. 9, 2012, and to U.S. Utility patent application Ser. No. 13/417,193, entitled BIOLOGICAL DATA NETWORKS AND METHODS THEREFOR, filed on Mar. 9, 2012, the disclosures of which are hereby incorporated by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ANNA_006_06US_SeqList_ST25.txt, date recorded: May 8, 2012, file size 2 kilobytes).

FIELD

This application is generally directed to processing and networking polymeric sequence information, including biopolymeric sequence information such as DNA sequence information.

BACKGROUND

Deoxyribonucleic acid ("DNA") sequencing is the process of determining the ordering of nucleotide bases (adenine (A), guanine (G), cytosine (C) and thymine (T)) in molecular DNA. Knowledge of DNA sequences is invaluable in basic biological research as well as in numerous applied fields such as, but not limited to, medicine, health, agriculture, livestock, population genetics, social networking, biotechnology, forensic science, security, and other areas of biology and life sciences.

Sequencing has been done since the 1956s, when academic researchers began using laborious methods based on two-dimensional chromatography. Due to the initial difficulties in sequencing in the early 1956s, the cost and speed could be measured in scientist years per nucleotide base as researchers set out to sequence the first restriction endonuclease site containing just a handful of bases. Thirty years later, the entire 3.2 billion bases of the human genome have been sequenced, with a first complete draft of the human genome done at a cost of about three billion dollars. Since then sequencing costs have rapidly decreased.

Today, the cost of sequencing the human genome is on the order of $5000 and is expected to hit the $1000 mark later this year with the results available in hours, much like a routine blood test. As the cost of sequencing the human genome continues to plummet, the number of individuals having their DNA sequenced for medical, as well as other purposes, will likely increase significantly. Currently, the nucleotide base sequence data collected from DNA sequencing operations are stored in multiple different formats in a number of different databases.

Such databases also contain annotations and other attribute information related to the DNA sequence data including, for example, information concerning single nucleotide polymorphisms (SNPs), gene expression, copy number variations methylation sequence. Moreover, transcriptomic and proteomic data are also present in multiple formats in multiple databases. This renders it impractical to exchange and process the sources of genome sequence data and related information collected in various locations, thereby hampering the potential for scientific discoveries and advancements.

SUMMARY

In one aspect the disclosure is directed to a method of transmitting information pertaining to biological sequence data. The method includes generating a data packet including a first header containing network routing information and a second header associated with a layered model representative of the biological sequence data. The method also includes storing the data packet within a queue and transmitting the data packet to a node of a network.

In another aspect the disclosure relates to a method of receiving information pertaining to biological sequence data. The method includes receiving, at a network interface of a node of a network, a data packet including a first header containing network routing information and a second header associated with a layered model representative of the biological sequence data. The method also includes parsing the data packet and separating the first header from the second header.

In yet another aspect the disclosure relates to a network node which includes a packet generator configured to generate a data packet. The data packet includes a first header containing network routing information and a second header associated with a layered model representative of the biological sequence data. The network node further includes a queue communicatively coupled to the packet generator, the queue storing the data packet. In addition, the network node includes a transmit controller for controlling transmission of the data packet to another node of a network.

The disclosure also pertains to a network node including a network interface configured to receive a data packet. The data packet includes a first header containing network routing information and a second header associated with a layered model representative of the biological sequence data. The network node also includes a processing module communicatively coupled to the network interface, the processing module parsing the data packet and separating the first header from the second header.

BRIEF DESCRIPTION OF THE DRAWINGS

Various objects and advantages and a more complete understanding of the disclosure are apparent and more readily appreciated by reference to the following Detailed Description and to the appended claims when taken in conjunction with the accompanying Drawings wherein:

DETAILED DESCRIPTION

Introduction

Figure 1:
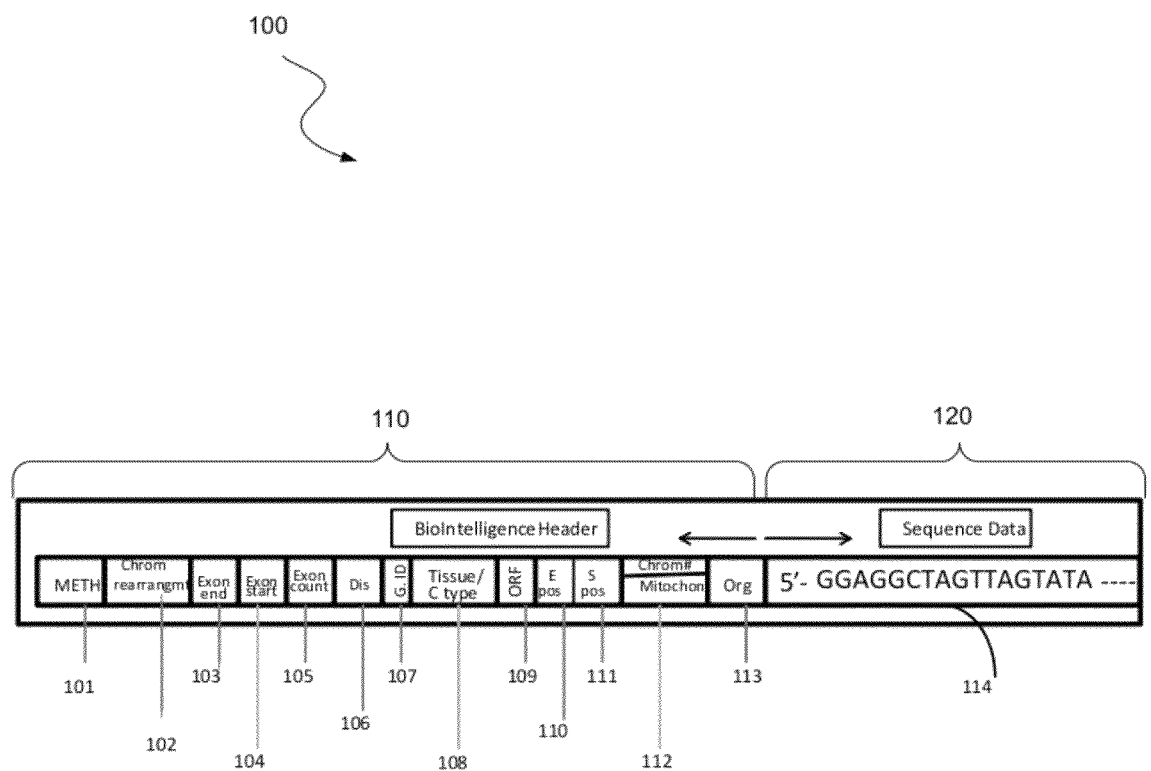
FIG. 1 is a representation is provided of a biological data unit comprised of a payload containing DNA sequence data (SEQ ID NO.: 1) and a BioIntelligence header containing information having biological relevance to the DNA sequence data (SEQ ID NO.: 1) within the payload.

This disclosure relates generally to an innovative new biological data network and related methods capable of efficiently handling the massive quantities of DNA sequence data and related information expected to be produced as sequencing costs continue to decrease. The disclosed network and approaches permit such sequence data and related medical or other information to be efficiently stored in data containers provided at either a central location or distributed throughout a network, and facilitate the efficient network-based searching, transfer, processing, management and analysis of the stored information in a manner designed to meet the demands of specific applications.

The disclosed approaches permit such sequence data and any related medical, biological, referential or other information, be it computed, human-entered/directed or a combination thereof, to be efficiently transmitted and/or shared or otherwise conveyed from a centralized location or either partly or wholly distributed throughout the biological data network. These approaches also facilitate data formats and encodings used in the efficient processing, management and analysis of various "omics" (i.e., proto/onco/pharma) information. The innovative new biological data network or, equivalently, network, is configured to operate with respect to biological data units stored at various network locations.

Each biological data unit will generally be comprised of one or more headers associated with or relating to a payload containing a representation of segmented DNA sequence data or other non-sequential data of interest. The term header in this context refers to one or more pieces of information that have relevance to the payload, without regard to how or where such information is physically stored or represented within the network. As is discussed below, it will be appreciated that certain operations performed by the nodes or elements of the biological data network may be effected with respect to the entirety of the biological data units undergoing processing; that is, with respect to representations of both the segmented sequence data and headers of such biological data units.

However, the elements of the biological data network may perform other operations by, for example, comparing or correlating only the headers of the biological data units being processed. In this way network bandwidth may be conserved by obviating the need for network transport of segmented biological sequence data, or some representation thereof, in connection with various processing operations involving biological units nominally stored at different network locations.

The biological data network may be comprised of a plurality of network nodes configured with processing and analytical capabilities, which are individually or collectively capable of responding to machine or user queries or requests for information. As is discussed below, the functionality of the new biological data network may be integrated into the current architectural framework of the Open Systems Interconnection (OSI) seven-layer model and the Transmission Control Protocol and Internet Protocol (TCP/IP) model for network and computing communications. This will allow service providers to configure existing network infrastructure to accommodate biological sequence data to deliver optimized quality of service for medical and health professionals practicing genomics-based personalized medicine. Alternatively or in addition, the new biological data network may be realized as an Internet-based overlay network capable of providing biological, medical and health-related intelligence to applications supported by the network.

The new biological data network facilitates overcoming the daunting challenges associated with analysis of various pertinent omics data types together with, and in the context of, all relevant, available prior knowledge. In this regard the new biological data network may facilitate development of an integrated ecosystem in which distributed databases are accessible on a network and in which the data stored therein is configured to be linked by. This new biological data network may enable, for example, forming, securing, linking, searching, filtering, sorting, aggregating and connecting an individual's genome data with a layered data model of existing knowledge in order to facilitate extraction of new and meaningful information.

Overview of Biological Data Units and Headers

As disclosed herein, the innovative new biological data network is configured to operate with respect to biological data units stored at various network locations. Biological data units can be considered as a set of information that is known or can be predicted to be associated with certain segments of genome sequences. Biological data units will generally be comprised of one or more headers associated with or relating to a payload containing a representation of segmented DNA sequence data or other non-sequential data of interest.

The biological data units may be generated by dividing source DNA sequences into segments and associating one or more headers (also referred to herein as "BI headers" or annotations or attributes) with one or more segments of genome sequence data. The various component parts XML metadata files that are of the header information contained in biological data units can be stored in distributed storage containers that are accessible on a network. Furthermore, the different segments of a whole genome sequence data contained in the payload of biological data units may be stored in multiple BAM files at various different locations on a network.

Each BI header can be considered a specific piece of information or set of information that may be associated with or have biological relevance to one or more specific segments of DNA sequence data within the payload of the biological data unit. It should be appreciated that any information that is relevant to the segmented sequence data payload of a biological data unit can be placed in the one or more headers of the data unit or, as is discussed below, within headers of other biological data units. It should also be clearly understood that the information contained in any biological data unit can be highly distributed and network linked in such a manner that allows filtration and dynamic recombination of any permutation of associated attributes and sequence segments.

The headers may be arranged in any order, whether dependent upon or independent of the payload data. However, in one embodiment the headers are each respectively associated with at least one layer of a biological data model of existing knowledge that is representative of the biological sequence data which, for example, may be stored as BAM files within the payloads of the distributed biological data units with which such headers or XML metadata attributes are associated.

Although the present disclosure provides specific examples of the use of BI headers in the context of a layered data model, it should be understood that BI headers may be realized in essentially any form capable of embedding information within, or associating such information with, all or part of any biological or other polymeric sequence or plurality thereof. For example, one or more BI headers could be associated with any permutation of segments of DNA sequence or other such polymeric sequence or within any combination thereof, in any analog or digital format.

The BI headers could also be placed within a representation of associated polymeric sequence data, or could be otherwise associated with any electronic file or other electronic structure representative of molecular information. In other words, the one or more metadata attributes that are stored in multiple storage containers on a network may compose headers that are specifically associated with at least one segment of sequence contained in a file transfer session.

In the case in which data is embedded within DNA or other biological sequence information, the BI headers or tags including the data may be placed in front of, behind or in any arbitrary position within any particular segmented sequence data or multiple segmented data sequences. In other words, in one particular embodiment of the invention, information that is associated directly or indirectly may be stored within the base calls of reads that are contained in BAM files or any other sequence file format or internal memory structures, for example. This approach would involve a method for integrating, at least one specific attribute of information that is associated with a genome sequence between and or among the base calls contained within reads of sequence data files.

In addition, the data may be embedded in a contiguous or disbursed manner among and within the base calls of the segmented sequence data. When this highly structured and layered approach is applied to the storage configuration of this sequence data and associated information it will advantageously facilitate the computationally efficient, effective and rapid analysis of, for example, the massive quantities of genome sequence data being generated by next-generation, high-throughput DNA sequencing machines.

In particular, distributed biological data units containing segmented DNA sequence data and associated attributes may be stored, sorted, filtered and operated on for various scope and depth of analysis based upon the said associated information which is contained within the headers. This obviates the need to manipulate, transfer and otherwise breach the security of the segmented DNA sequence data in order to process and analyze such data.

One embodiment of the layered data model of the existing body of relevant knowledge includes not only of or pertaining to biologically-relevant data but also other metadata which are associated with the nucleic acid sequence files. Such MetaIntelligence™ metadata may include, for example, facts, information, knowledge and prediction derived from biological, clinical, pharmacological, environmental, medical or other health-related data, including but not limited to other biological sequence data such as methylation sequence data as well as information on differential expression, alternative splicing, copy number variation and other related information.

The DNA sequence information included within the biological data units described herein may be obtained from a variety of sources. For example, DNA sequence information may be obtained "directly" from DNA sequencing apparatus, as well as from sequence data files that are stored in private and publicly accessible genome data repositories. Additionally, it may be computationally derived and/or manually gathered or inferred. In the case of the database of Genotypes and Phenotypes at the National Center for Biotechnology Information at the National Library of Medicine, the DNA sequence entries may be stored as BAM, SRF, fastq as well as in the FASTA format, which includes annotated information concerning the sequence data files. In one embodiment certain of the information contained within the one or more headers of each biological data unit would be obtained from publicly accessible databases containing genome data sequences.

Turning now to FIG. 1, a representation is provided of a biological data unit comprised of a payload containing DNA sequence data and a header containing information having biological relevance to the DNA sequence data within the payload. Furthermore, it should be appreciated that information contained in a particular header may also point or associate with sequence data that is stored in at least one data container as the payload portion of biological data units.

In addition, it should be understood that the header information and sequence payload that is contained within biological data units relate directly to attributes in XML metadata files and BAM sequence files, respectively. Any key value can associate with one or more sequence files or segments of sequence within such files. In one particular aspect of the disclosed approach, the key value may be information of or pertaining to a drug or its effect and the sequence may be a segment of sequence contained in a GeneTorrent™ Object file transfer session.

The header information may associate with or relate to for example a microRNA sequence or the regulatory region of a gene or interaction with another gene product from at least one molecular pathway. Since the example that is presented as FIG. 1 shows that the payload contains DNA sequence data, the biological data unit of FIG. 1 may also be referred to herein as a DNA protocol data unit (DPDU). The DPDU can be considered as distributed biological data units that are encapsulated with information for transfer, control and other data that is relevant to the protocol.

In one embodiment, the exemplary biological data unit that is depicted in FIG. 1 would be associated with the DPDUs that are encapsulated and involved in a computer-implemented method for processing data units. For example, in the case where the sequence payload is RNA sequence data which may be derived from RNA-seq or deduced from the DNA sequence data could be included within RNA protocol data units (RPDU) comprised of a plurality of RNA specific headers and a payload comprised of the RNA sequence data. The header information contained in distributed components of RPDUs may include but not be limited to information on differential expression, splicing, processing and other post-transcriptional modifications of RNA.

Similarly, a protein protocol data unit (PPDU) comprised of peptide-specific headers and a payload containing a representation of amino acid sequence data. The biological sequence data that is contained in the payload of PPDUs may be from mass spectrophotometry protein sequencing data or deduced from the DNA sequence data of the DPDU of FIG. 1. Furthermore, the header information may be information such as the protein's concentration in body fluids or the extent of protein activity which could also be associated with the DPDU(s) of the representative gene.

A Network-Based Layered Biological Data Model

Figure 2:
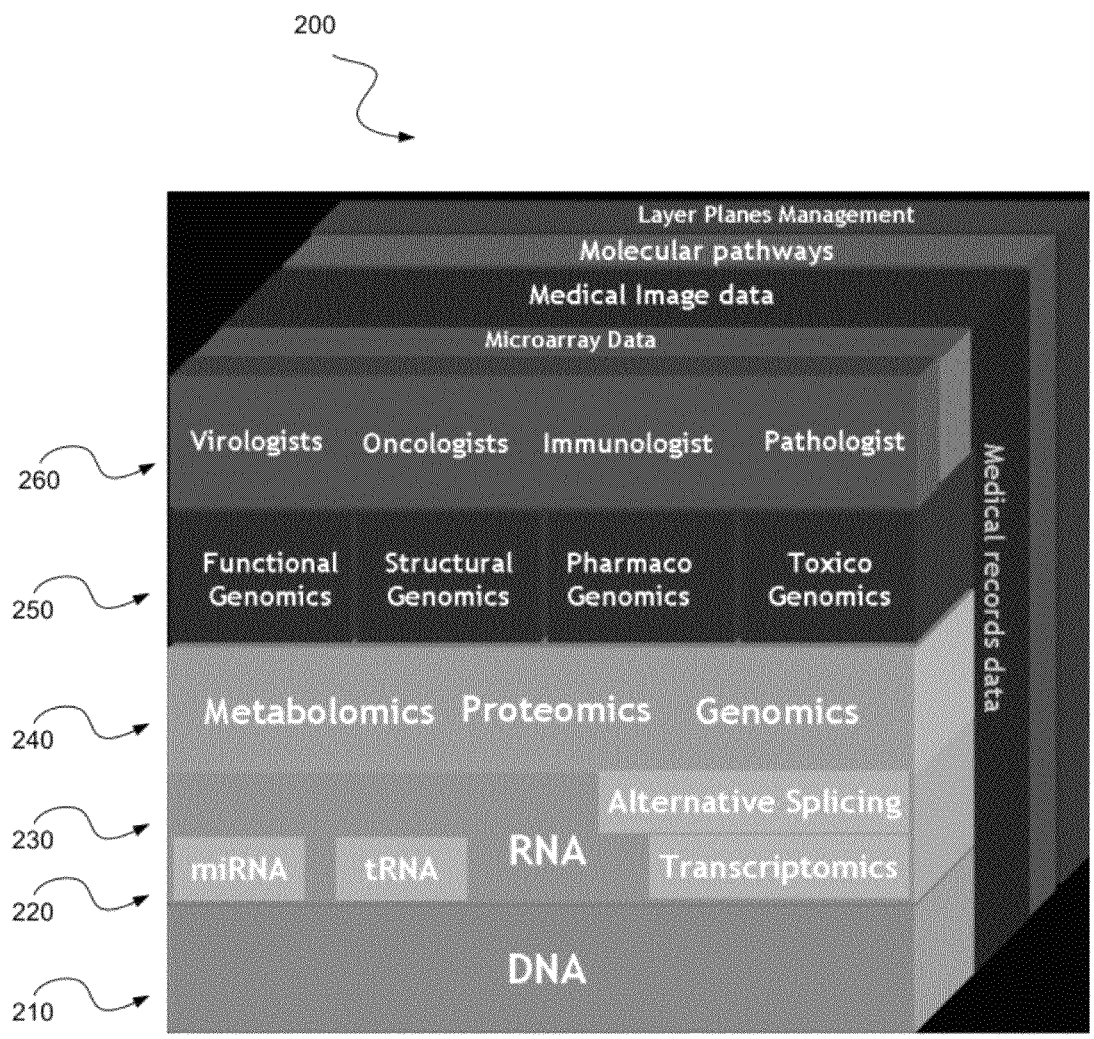
FIG. 2 illustratively represents a biological data model which includes a plurality of interrelated layers.

Referring now to FIG. 2, representation of genome sequence data using distributed biological data units having header information corresponding to the different layers of the biological data model 200 is expected to facilitate efficient processing of such sequence data. For example, in cases in which it is desired to query one or more data containers containing large numbers of biological data units, the multi-layered representation of FIG. 2 enables queries to be configured in such a manner to be analyzed using only the information within the xml metadata files that contain portions of the distributed data units and without the need to directly examine the segmented sequence data contained within the payload of such data units.

As a consequence, data from different smart repositories can be processed in real time, and access to various types of data allows for more sophisticated analysis of biological, medical, clinical and other related datasets. This is believed to represent a significant advance relative to conventional database-centric processing techniques, which typically rely upon evaluation of the entirety of the sequence information stored within a database.

It should be appreciated that the multi-layered, multi-dimensional data architecture represented by FIG. 2 provides but one example of the many different architectures capable of being implemented using biological data units containing headers. It should also be understood that the data layers are exemplary and not intended to limit the scope or extent of the invention. As shown in FIG. 2, the biological data model 200 includes a DNA layer 210, an RNA layer 220, a protein layer 230, a systems biology layer 240, an application layer 250, a top level field-specific layer 260, a medical data layer 270, a molecular pathways layer 280 and a management layer 290. In various embodiments the information associated with each of these layers may be included within the header and/or payload of biological data units that are configured in a way that is consistent with the data model 200.

The DNA layer 210 will generally contain information, data and knowledge associated with DNA found in public and private databases, as well as information published or generally accepted by the scientific community as being credible. For example and without limitation, the information included within the DNA layer 210 may comprise: 1) the nucleotide sequence of DNA segment, 2) chromosome number, positions and location, 3) nucleotide start and end positions of a particular segment of sequence, 4) name of the gene if and when the segment encodes known gene, 5) annotations for the enhancer and promoter region, 6) identification of open reading frames that are present within the segment of genome sequence, 7) transcription start site and start codon used for translation, 8) annotations for the identification of introns and exons, 9) known, unknown and predicted mutations, 10) the various types of mutations, 11) phenotypic effects, 12) any metadata or annotation or knowledge or possible predictions on any sequence of DNA found in any other database.

The RNA layer 220 is positioned adjacent to and is intimately associated with the DNA layer 210. The information included within this pair of layers is highly interrelated. The RNA layer 220 contains information that is related to or pertaining to RNA sequence, modification, function and structure. In certain embodiments this layer may contain information relating to various types of RNA including, for example, mRNA, tRNA, rRNA, miRNA, siRNA, and other non-coding RNAs. The layer 220 may also include information concerning snRNA involved with splicing and guiding RNA in telomerase.

Examples of specific information which may be included within the RNA layer 220 include, without limitation: 1) the primary base sequence of the pre-mRNA and mature mRNA sequences, 2) information on the sequences and locations of known and predicted ribosome binding site, 3) initiation site for protein synthesis or translation start codon, 4) processing and molecular modification of mRNA, 5) positions and sequence of splice junctions, 6) know and predictable alternative splicing data, 7) polyA tail data, 8) microRNA binding data, 9) RNA expression data from microarray and polysome analysis, 10) and essentially any other data concerning RNA contained within any other database.

In the exemplary representation of FIG. 2, the protein layer 230 resides directly on top of the RNA layer 220. In this configuration, information flows from the RNA layer 220 to the protein layer 230 and can associate with information from the DNA layer 210 through the RNA layer 220. This means, for example, that data from the prior knowledge information contained in the protein layer 230 can be processed and analyzed along with existing knowledge from the DNA layer. The following types of information may, for example and without limitation, be included within this layer: 1) amino acid sequence of a protein, 2) any available existing information on the post-translational modifications of a protein encoded by the segmented genome sequence, 3) any information on the activity of a protein or related polypeptides, 4) information on the crystal structure, 5) NMR data, 6) well-established mass spectrometry data that is relevant to the segmented sequence, 7) any information on protein-protein interactions, 8) any protein-nucleic acid interactions, 9) any pathway involvement information, 10) other data, related information, annotation and attribute information concerning any protein, polypeptide or nascent peptide published or stored within any other accessible genome data repository.

The biological systems layer 240 may include information relating to, for example and without limitation, transcriptomics, genomics, epigenomics, proteomics, metabolomics and other biological-system-related data. As the field of bioinformatics advances further, this layer may be scaled to accommodate other systems-level information, e.g., interactomics, immunomics, chromosomomics, and the like. This layer biological systems layer 240 is preferably situated between the protein layer 230 and the application layer 250. The application layer 250 serves to facilitate user-definable interaction with the prior knowledge that is included within lower layers of the data model 200. in the application layer 250 may use application-specific filtering of attributes to deliver query, analysis and processing results in real time.

The top-level expert application layer 260 uses data from microarray gene expression analysis, mass spectrometry proteomics data, copy-number variation data, single nucleotide polymorphisms and/or other data related to disease conditions, phenotypic expression, behavior, pharmacogenetics, epigenetic markers to run applications relating to processing, transport, analysis, compression, retrieval, storage and any other such operation capable of being applied to biological sequence data. In the embodiment of the data model of existing knowledge that is represented in FIG. 2, the layer 260 resides on top of the cubical data model 200 along with the suite of application layer software programs and related information in section 250, and is adjacent the medical data layer 270.

The medical information layer that is presented in section 270 may contain, without limitation, clinical data, personal health history and record data, medication data, lab test result data, image data (mammograms, x-ray, MRI, CAT scan, ultrasound, etc.), any other relevant, related, correlated or associated data. In this case, accepted discoveries, knowledge, calculations or predictions that are strongly linked with the clinical measurements and information may be configured in a way that is consistent with the ability to interrogate this prior knowledge base with metadata attributes.

The molecular pathways layer 280 will generally include information concerning pathways and molecular systems as well as the proteins, nucleic acids and metabolites that participate in the biological cycle. This layer of the layered molecular model may include specific information on the differential expression of certain genes at the level of organs, tissues, cell types, systems and pathways as they are related to the pertinent data found in headers of the biological data units that are involved in the response to a query. In another aspect of the invention the information represented in the pathway layer 280 may involve the measure of specific molecular activities of the proteins that are participants in a particular pathway.

The metadata attribute information that resides within the layer 280 of the layered data model of existing knowledge may be focused on, for example and without limitation, protein-protein interactions, protein-nucleic acid interactions, as we as the various types of interactions that may exist between and among different molecules of nucleic acids and protein-metabolite interactions. This type of information could prove to be very powerful for elucidating key biological pathways, and thus may be incredibly useful for identifying new and important drug targets. Furthermore, the information that is comprised in this layer may also include, for example, sequence data and annotations in pathway specific databases such as Reactome, IntAct and Rhea at EBI. The management layer 290 sits atop the z-dimension of layers within the prior knowledge data model 1600 and serves as the engine that controls and manages the flow of data across the cubical structure.

As may be appreciated with reference to FIG. 2, the illustrated biological data model is representative of the associations between and among layers of existing knowledge as well as the intra and interrelationships that exist among and between the highly distributed biological data units described above. In particular, the headers consisting of information pertaining to the DNA-specific, RNA-specific and peptide specific biological data units are each associated with at least one of the "layers" of the biological data model of FIG. 2, i.e., the DNA, RNA and peptide layers, respectively.

Alternatively, a given biological data unit which may be stored in multiple storage containers may comprise a payload containing a representation of biological sequence data and a plurality of headers, each of which is associated with one or more of the layers of the biological data model of FIG. 2. As is discussed below, although each header may be characterized as being associated with a certain layer of a data model, each may also point to or otherwise reference information in the header or payload of a separate biological data unit that may be stored in multiple storage containers may further be associated with a different layer of the biological data model.

headers may be associated with any form of intelligence or information capable of being represented as headers, tags or other parametric information which relates to the biological sequence data within the payload of a biological data unit. Alternatively or additionally, headers may point to relevant or unique (or arbitrarily assigned for the processing purpose) information that is associated with the biological sequence data within the payload.

A header may be associated with any information which is either known or predicted based upon scientific evidence, and may also serve as a placeholder for information which is currently unknown but which later may be discovered or otherwise becomes known. For example, such information may include any type of information related to the source biological sequence data including, for example, analytical or statistical information, testing-based data such as gene expression data from microarray analysis, theories or facts based on research and studies (either clinical or laboratory), or information at the community or population level based study or any such related observation from the wild or nature.

In one embodiment relevant information concerning a certain segment of DNA sequence or biological sequence data may be considered metadata and could, for example, include clinical, pharmacological, phenotypic or environmental data capable of being embedded and stored in more than one storage container but with very close association with the sequence data as part of the payload or included within a look-up table.

One distinct advantage to storing metadata and sequence files in a manner that allows for effective and robust tracking and linking of the data is that it enables DNA and other biological sequences that make up large data files to be more efficiently processed and managed. The type of information that may be embedded or associated with segments of DNA sequences or any other biological, chemical or synthetic polymeric sequence can be represented in the form of packet headers, but any other format or method capable of representing this information in association with one or more segments of biological sequence data within a data unit is within the scope of the teachings presented herein.

The systems described herein are believed to be capable of facilitating real-time processing of biological sequence data and other related data such as, for example and without limitation, gene expression data, deletion analysis from comparative genomic hybridization, quantitative polymerase chain reaction, quantitative trait loci data, CpG island methylation analysis, alternative splice variants, microRNA analysis, SNP and copy number variation data as well as mass spectrometry data on related protein sequence and structure. Such real-time processing capability may enable a variety of applications including, for example, medical applications.

The types of medical applications that could be facilitated by this approach may include an automated computer-implemented algorithm that allows the storing, filtering, sorting and tracking of an individual's whole genome sequence in segments as they relate to all the attributes and annotations in association with a biological data model of existing knowledge to extract meaningful and relevant results to specific queries. The processing and analysis of this data will unveil a new class of rich information that can be utilized in accordance with the layered data model of prior knowledge.

BI headers may be used for the embedding of biologically relevant information, in full or in part, in combination with any polymeric sequence or part or combination thereof, and may be placed at either end of such polymeric sequence or in association within any combination of such polymeric sequences. In addition, embedded information can be considered to be information that is clustered and linked in such a way that relevant information that is related to sequence data files are linked to allow for precipitation of meaningful new insight. Furthermore, the various components of the metadata information and sequence segments can be accessible from multiple storage containers on a network.

BI headers may be configured to be in any format and may be associated with one or more segments of polymeric sequence data. Furthermore, in certain cases the components of biological data units may be stored in a centralized container and in such case the BI Headers may be positioned in front of or behind (tail) the polymeric sequence data, or at any set of arbitrary locations within the representation of the segmented sequence data. Moreover, the BI headers may comprise contiguous strings of information or may be themselves segmented and the constituent segments placed (randomly or in accordance with a known pattern) among and between the segments of sequence data which is comprised within one or more biological data units.

The use of BI headers in representing genome sequence data in a structured format advantageously provides an enhanced capability for classifying and filtering the sequence data based upon any of several stored existing knowledge fields that are related to the said sequence segment. This approach allows for the sequence data to be sorted based on the abstracted descriptive information which is contained within the BI headers relating to the segmented sequence data of a specific biological data unit.

For example, the segmented genome sequence data represented by a plurality of biological data units could be processed such that, a particular gene that is normally known to be located at a certain position on chromosome 1 could be sorted along with other genes or gene products from the same or a different chromosome if the corresponding genes or gene products are associated with a particular molecular pathway, drug treatment, health condition, diagnosis, disease or phenotype. Alternatively, it should be known that certain chromosomal rearrangements could generate a similar result when a portion of one chromosome is transferred through translocation and becomes part of another.

In the general case not all of the segments of DNA sequence data within the set of biological data units resulting from segmentation of an individual genome will directly associate with every field of the applicable BI header attributes. For example, a certain biological data unit may contain a segment of DNA sequence lacking an open reading frame, in which case the exon count field of the DNA-specific BI header would not be applicable. In any case, the particular header information type along with other header information types are maintained as place holders for future scaling of the depth and scope of intelligence that is contained within the XML metadata files. This permits biological information relating to the segmented DNA sequence data of a certain biological data unit which is not yet known to be easily added to the appropriate layer of the biological data model once the information becomes known and, in certain cases, scientifically validated.

In certain exemplary embodiments disclosed herein, the biological or other polymeric sequence data contained within the payload of a biological data unit is represented in a two-bit binary format. However, it should be appreciated that other representations are within the scope of the teachings herein. For example, the instruction set architecture described in co-pending application Ser. No. 12/828,234 (the "'234 application") may be employed in certain embodiments described herein to more efficiently represent and process the segmented genome sequence data within the payload of biological data units. Accordingly, in order to facilitate comprehension of these certain embodiments, a description is provided below of certain aspects of the instruction set architecture described in the '234 application.

Representation of Polymeric Sequence Data Using Biological Data Units

One aspect the present disclosure describes an innovative methodology for biological sequence manipulation well-suited to address the difficulties that are related to the processing comparative sequence analysis of large quantities of DNA sequence data. The disclosed methodologies enable segmented representations of such sequence data to be efficiently stored (either locally or in a distributed fashion), searched, moved, processed, managed and analyzed in an optimal manner in light of the demands of specific applications.

The disclosed method involves breaking whole genome DNA sequence entries into deliberate segments and packetizing the fragments in association with header information to form biological data units. In one embodiment much of the header information may be obtained from private or public databases containing information pertaining to involved molecular pathways, drug databases, published research data that can be found in well-established databases such as, for example, dbGaP and EMBL. The DNA sequence entries within many public databases may be stored in a BAM file format, which accommodates the inclusions of annotated information concerning the sequence. For example, an entry for a DNA sequence recorded in the BAM file format could include annotated information identifying the name of the organism from which the DNA was isolated and the gene or genes contained in the specific sequence entry.

Alternatively, the sequence file may contain the base sequence information while the ancillary metadata information could be contained in XML files as specific attributes that are associated with a particular segment of the sequence. The associated information that is contained in these files may relate with prior knowledge that is configured in a biological model that is consistent with a layered data model.

In addition, the information that is pertinent to which chromosome the particular DNA sequence segment was obtained and the starting and ending base positions of the sequence would also typically be available. Furthermore, other public and private databases include information relating to, for example, the location of human CpG islands and their methylation sequence, as well as the genes with which such islands are associated (see, e.g., http://data.microarrays.ca/cpg/index.htm).

For each identifiable gene there will be an essential need for a normal control state of the particular gene. Database entries that contain genes that are identified as being associated with a RefSeqGene, which pertains to a project within NCBI's Reference Sequence (RefSeq) project, provide another potential source of header information. The RefSeqGene project defines the DNA sequences of genes that are well-characterized by leaders in the scientific community to be used as reference standards which is a part of the Locus Reference Genomic (LRG) project. In particular, sequences labeled with the keyword RefSeqGene serve as a stable foundation for reporting mutations, for establishing conventions for numbering exons and introns, and for defining the coordinates of other biologically significant variation. DNA sequence entries that associate directly with the RefSeqGene will be well-supported, exist in nature, and, to the extent for which it is possible, represent a prevalent, 'normal' allele.

It should be appreciated that there may be different schemas for segmentation and packetizing sequence entries in order to associate the highly relevant attribute information with specific sequence segments. For example, in the case in which it is suitable to segment sequence entries into packets containing genes or, alternatively, into introns and exons, relevant data is available for placement into the header information relating to the metadata attributes of the biological data units containing such sequence segments.

Biological Data Units Including Headers

Referring again to FIG. 1, the header 110 is seen to include a number of fields containing information of biological relevance to the DNA sequence data within the payload 120 of the biological data unit 100. The information that is contained within the header may be stored in multiple containers on a biological data network. See, e.g., FIG. 5.

In one approach, biological data units are created at least in part by specifically linking information from XML metadata files with particular segments of BAM file sequence data. In this case, the biological data units can be considered a unit of information that a certain relationship that can be stored or streaming from and to multiple nodes on a network. In this case the information that is contained within the BI header distributed and is able to link with sequence segments specifically. The protocols used for the transmission of these precisely related cluster of information in biological data units is integrated with a computer implemented program that defines and classifies the link between and among the header information and the segment of sequence payload.

It should be appreciated that FIG. 1 provides only one specific exemplary representation of the type of biologically relevant information which may be included within a header of distributed biological data units. Accordingly, including other types of relevant attributes and information within a header or the equivalent, regardless of how the data is represented or configured, is believed to be within the scope of the present disclosure.

In addition, although the following generally describes information as being contained or included within various sections of the header 110, it should be understood that in various embodiments such headers may distributed and may contain pointers, tags or links to other structures or memory locations storing the associated header information.

Similarly, the payload 120 may contain a representation of the segmented DNA sequence data of interest, or may include one or more pointers or links to other structures or locations containing a representation of such sequence data. In this case, the various segments of a particular whole genome sequence may be stored in a distributive manner in multiple containers that are accessible on a network.

A first section 101 of the header 110 provides information concerning CpG methylation sequence data that pertains to the various positions of the DNA sequence segment within the payload 120 of the biological data unit 100. In other words, the information that is contained in the ancillary files that are associated with the sequence points to section 101. Identification of these CpG islands and the methylation sequence will likely play an important role in understanding regulation of the associated genes and any involvement with disease.

The header information that is contained in section 110 also includes a property of chromosome banding pattern in section 102 containing information concerning any chromosomal rearrangement observed, known, yet unknown and or may be predicted to be involved with at least one segment of genome sequence data linked to this attribute. These types of cytogenetic abnormalities are often associated with severe phenotypic effects. This information may be configured to be in any other format to represent the genomic effects of chromosomal rearrangements which are known to be common in cancer tumor genomics.

Header sections 103 and 104 provide information identifying the beginning and ending positions for the exons that are contained in the DNA sequence segment included within the payload 120. In the case of whole exome sequencing this information represents exons throughout the whole genome that are expressed in genes. Since exon selection has tissue and cell type specificity, these positions may be different in the various cell types resulting from a splice variant or alternative splicing. Along with this DNA coding information for individual exons, header section 105 may represent information in a metadata file of a count of the number of exons contained in the DNA sequence segment included within the payload 120. This type of information is known to be relevant in disorder involving exon skipping and exon duplication.

Certain particular attribute-informational link specifically with one or more DNA sequence segments within payload 120 having some association with a disease will be represented by the attribute information contained within section 106. Information that is pertaining to certain known molecular pathways or systems that may have molecular interactions with other genes or gene products that would also be described within this section of the BI header. Alternatively, since variations of said certain gene could be involved in one or more diseases, such information would also generally be contained within header section 106.

To the extent the DNA sequence segment in the payload 120 contains a part of a gene, a gene or plurality of genes, then the header section 107 provides all of the pertinent information that relate specifically to the applicable known gene name or gene ID. Header section 108 may represent the type of information that specifies the tissue or cell type which may be relevant to the extent and level of expression of the various exons that may be encoded in the said gene or segment of genome that is described in section 105.

The metadata attribute located in the header section 109 will provide information concerning all possible open reading frames present within the segment of genome sequence data that is contained within the payload 102. This type of attribute will be crucial for characterizing disease associated variants which are contained within what appears to be open reading frames that express no proteins or peptides that are detectable with today's methods.

Header section 110 and 111 represent the metadata annotations that specify the start and end positions of the DNA sequence segment that is linked to a specific segment of a BAM file, represented by the payload 102. These positions may be considered arbitrary since the positions in the sequence could be more than one reference sequence.

Section 112 indicates if the segmented DNA sequence data within the payload 102 is chromosomal, microbial or mitochondrial. Furthermore, section 113 provides information concerning the genus and species of the origin of the DNA sequence segment represented with the payload 102. It should be appreciated that sections 112 and 113 will provide the information that describes all the DNA sequence data that is associated with an individual including and not limited to microbes attached on the outside and found on the inside of said individual as well as genome sequence data from plants and other higher animals found in the digestive track.

All of the metadata annotations and attributes that are within the header 110 will generally contain prior knowledge information relating to the that is relevant to the DNA sequence which is functionally utilized while the data is being sorted, filtered and processed. This packetized structure of the DNA sequence data that is represented in bits and encapsulated with headers and other relevant information advantageously facilitates processing by existing network elements operative in accordance with layered or stacked protocol architectures.

For example, The Cancer Genome Atlas consortium has elected to implement biological data units comprised of headers consisting of information contained in XML metadata files and payloads comprised of genome sequence data contained in the BAM files. In this exemplary implementation a first specific type of information may reference the tissue type or cell type of the sequence files (section 108 of FIG. 1).

Similarly, second specific type of information type may reference a disease type (section 104 of FIG. 1).

Figure 3:
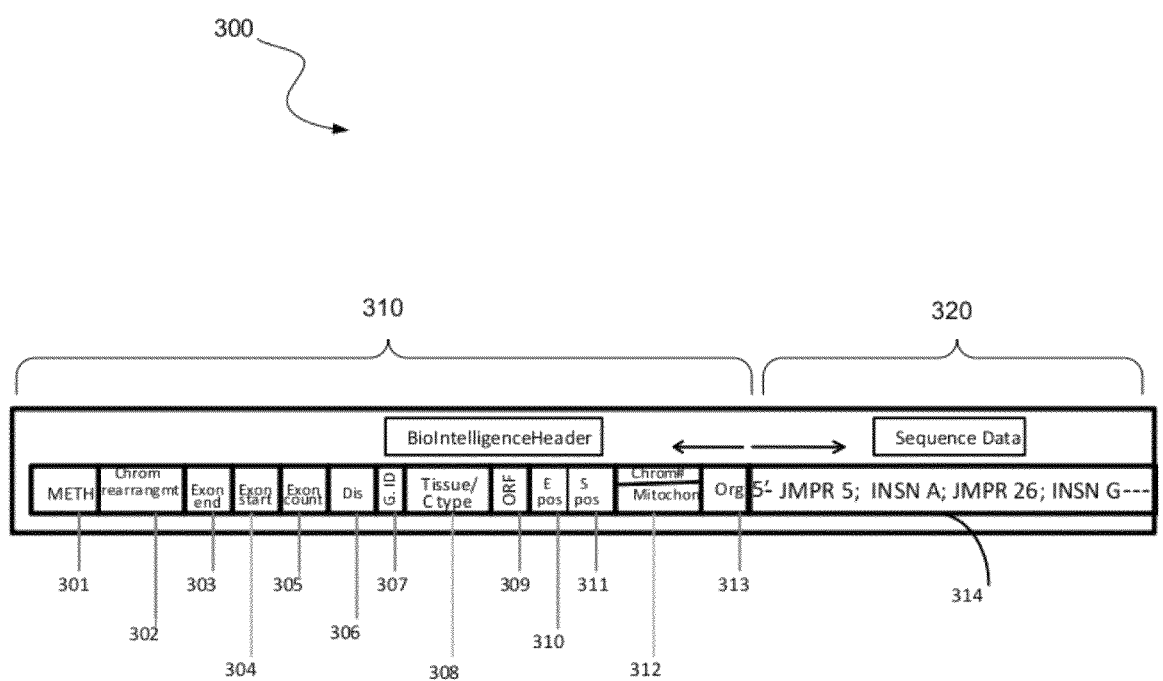
FIG. 3 depicts a biological data unit having a header and a payload containing an instruction-based representation of segmented DNA sequence data.

Attention is now directed to FIG. 3, which depicts a biological data unit 300 having a header 310 and a payload 320 containing an instruction-based representation of segmented DNA sequence data. The type of information that is illustrated in 310 is exemplary. Moreover, this information may be stored in one or more storage containers that are accessible on a network. The instruction-based representation is discussed above and in the copending '234 application. Although the content and representations of the payloads 110 and 310 differ, the same type of information is included within the headers 110 and 310 of the biological data units 100 and 300, respectively.

The distributed packetizing of segmented DNA sequence data files and the embedding of biologically and clinically relevant information in biological data units will enable development of a networked processing architecture within which such data may be organized and configured in a layered format. Based on preliminary results, the architecture is expected to be particularly suited for effecting rapid analysis of large amounts of data of this type.

In one approach, the header which is contained within such biological data units, is used to qualify or characterize the fragmented or otherwise segmented genome sequence data included within the payloads of such data units. In so doing, biological data units containing segmented DNA sequence data or other sequence data may now be sorted, filtered and operated upon based on the associated attribute information contained within the ancillary metadata files of the highly distributed data units.

For example, a data repository containing biological data units incorporating segmented DNA sequence data and related attribute information similar to that associated with the header 110 of FIG. 1 may be quickly and efficiently sorted in accordance with parameters defined by an application. This has been recently demonstrated with a system that has reduced to practice the concepts and ideas of the current disclosure as the repository that is now known as the Cancer Genome Hub (CGHub) operated by the University of California. In other words, the same segments of genome sequence may be sorted and analyzed in several different ways by using the header information associated with, or otherwise directly or indirectly linked to, the payload representation of the sequence segments.

It is highly expected that it would be beneficial to arrange and represent all of the genomic sequence information from an individual, e.g., from bacteria, animals, plants to humans, in accordance with the layered data architecture illustrated in FIG. 2. For example, consider the case in which a segment of a genome sequence data file of interest is included as the payload of a biological data unit stored in a data container which includes biological data units associated with DNA sequence data of other organisms.

Consider further that if, for example, the DNA sequence data of interest is a particular variant of a human gene associated with breast cancer, such as BRCA1, then such data could be extracted from the container by filtering the contents of the data container for metadata attributes associated specifically with the segment of DNA sequence data from the organism homo sapiens. The data units containing the specific BRCA1 variant along with all other DNA data packets containing human DNA sequence data may be easily extracted. However, sorting human DNA sequence data from the DNA sequence data from other organisms may not be sufficient enough of a challenge in view of the technical requirements of certain applications. Accordingly, additional processing and comparative analysis may be performed in which specific data units comprising certain segments of sequence data from human chromosome 17 would be filtered out from the data container.

Biological data units having payloads containing DNA sequence segments from chromosome 17 may provide a reasonable level of filtering. However, in order to efficiently analyze the gene most notably associated with breast cancer, further processing, sorting and filtering will be necessary. This may be achieved using several methods including but not limited to filtering on the specific start and end positions within the chromosome (S pos and E pos) or the gene ID (GID) or by disease, breast cancer. If the biological data units that are being sorted contain sequence segments data associated with an alternately-spliced variant of BRCA1, then this information may be contained in the header information representing the total exon count (see, e.g., header section 105 of FIG. 1), in addition to within the header sections including start exon and end exon information sections (see, e.g., header sections 103 and 104). Furthermore, additional information concerning tissue or cell type may need to be provided in order to perform the most intricate level of sorting and filtering of the biological data units associated with a specific BRCA1 variant.

The packetized structural configuration of the disclosed distributed biological data units further enable functional integration of a layered data models such as that depicted in FIG. 2. In particular, each metadata attribute of headers forming at least a part of or is linked to a particular biological data unit which may be associated with one or more specific layers of the model. One advantage of using a layered data model is that data from the various layers may interrelate during processing of the header information included within the set of biological data units being operated on or otherwise analyzed. For example, in the exemplary case described above, information from the RNA layer of the model relating to the splicing of introns from pre-mRNA was used to identify BRCA splice variants, thereby correctly facilitating determination of exon start and end positions.

The use of header information which are consistent with a layered data architecture also advantageously enables substantial changes to be made to the information associated with one layer of the model without necessitating that corresponding modifications be made to other layers of the model. For example, sequence variants may be observed at splice donor and splice acceptor sites which may change the splicing pattern and mRNA size, protein structure and function, and these changes may yet be accommodated and mapped to the DNA layer without requiring that corresponding changes be made the DNA layer of the existing knowledge data model.

Figure 4:
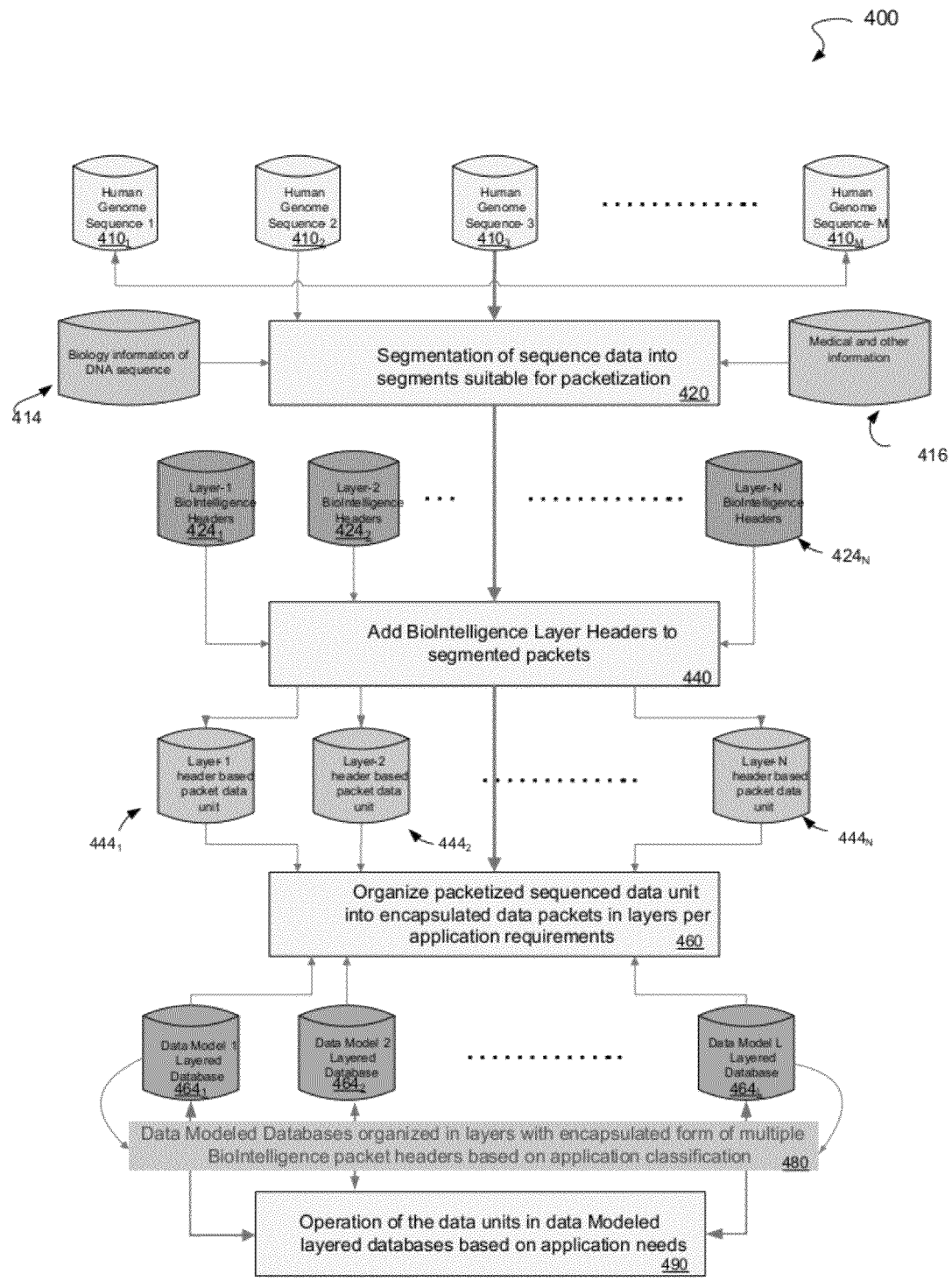
FIG. 4 is a logical flow diagram of a process for segmentation of biological sequence data and combining the segments with metadata attributes to form biological data units encapsulated with headers.

Attention is now directed to FIG. 4, which provides a logical flow diagram of a process 400 for segmentation of biological sequence data and combining the segments with metadata attributes to form biological data units encapsulated with headers. The process 400 provides one example of a way in which source DNA sequence data may be fragmented to generate biological data units containing DNA sequence segments and associated header information in accordance with a layered data model such as the biological data model 200.

In one embodiment the process 400 utilizes sequence feature information of the type annotated in well-established nucleotide databases 410 such as, for example, NCBI, EMBL and DDBJ for sorting, configuring and operating on the sequence data. By mapping the biological information within these databases into various layers of header information, a layered data model of existing knowledge can be constructed.

Referring to FIG. 4, human genomic DNA data is shown to be accessible from different storage elements 410. In this regard, the DNA sequence data can be stored in segments as sequences of individual chromosomes or partial chromosomes or as individual genes, and may comprise all or part of a genome. In addition, the DNA sequence data could be generated from a sequencing machine and the results made accessible to a network of computers. Further, genomic sequence data might be represented in any file format and produced using any approach including, for example, as a partial dipolar charge and phosphorescence sequence profile indicative of the sequence data.

In a stage 420, the sequence data obtained from storage elements 410 is mapped and aligned with the reference genomic sequence data. The DNA sequence is associated with a set of relevant molecular features using, for example, biological data 414 deemed valid by the scientific community. This data 414 is mapped to specific regions of a sequence entry. In addition, clinical and pharmacological data 416 demonstrated to be associated with any coding or non-coding regions of a sequence entry is also mapped.

In one embodiment layer-1 biological data units $444_1$ include a payload comprised of segmented DNA sequence data and a DNA layer header. Similarly, layer-2 biological data units $444_2$ may include a payload comprised of segmented DNA sequence data, a DNA layer header and an RNA layer header. A layer-N biological data unit $444_N$ may include a payload comprised of segmented DNA sequence data, a DNA layer header, an RNA layer header, and other headers associated with higher layers of the relevant data model.

Alternatively, in one embodiment layer-1 biological data units $444_1$ may include a payload comprised of segmented DNA sequence data and a DNA layer header, layer-2 biological data units $444_2$ may be comprised of a segmented RNA sequence data and an RNA layer header, and so on. In one embodiment a base unit may be prepended to or otherwise associated with each biological data unit in order to identify the specific headers included within the data unit and/or the number thereof.

In one embodiment headers 424 may include physical, chemical, or biological knowledge or findings, or any related molecular data that has been peer reviewed, published and accepted as valid. headers 424 may also include clinical, pharmacological and environmental data, as well as data from gene expression and methylation.

In certain embodiments headers 424 may further include information relating to gene and gene product interaction with other components of a pathway or related pathways. The information within headers 424 may also be obtained form, for example, microarray studies, copy number variation data, SNP data, complete genome hybridization, PCR and other related techniques, data types and studies.

The prior scientific knowledge and information associated with a specific sequence and included within a header 424 may be of several different types including, for example, molecular biological, clinical, medical and pharmacological information. In this regard such molecular and biological information could be separated and layered based on data from, for example, genomics, exomics, epigenomics, transcriptomics, proteomics, and metabolomics in order to yield data.

The data may also include DNA mutation data, splicing and alternative splicing data, as well as data relating to post-transcriptional control (including microRNA and other non-coding silencing RNA and other nuclease degradation pathways). Mass spectrometric data on protein structure and function, mutant protein products with reduced or null function, as well as toxic products could also be utilized as information.

In addition, pharmacological and clinical data relating to specific genes or gene regions disposed to exert effects through interaction with gene products or other components of a pathway could be considered as a class of header information. Finally, header information could also include environmental conditions or effects correlated with certain genes or gene products known or predicted to be related to a certain phenotypic effect or disease onset.

As mentioned above, during stage 440 headers 424 are associated with segmented DNA sequence data form biological data units comprised of a header 424 encapsulating a payload containing the segmented DNA sequence data. In this process the association of a header 424 to payload containing segmented genome sequence data may be carried out in any of a number of ways. For example, such association may be effected using a pointer table, tag, graph, dictionary structure, key value stores or by embedding header information directly into the segmented sequence data.

In a stage 460, the biological data units 444 may be organized into encapsulated data units in accordance with the requirements of particular applications. For example, in certain cases it may be desired to create encapsulated biological data units including only a subset of the headers which would otherwise be included in the biological data units associated with at least one particular layer of the biological data model of prior knowledge. For example, a certain application may require encapsulated biological data units having headers associated with only layers 1, 2 and 5 of a data model.

Another application may require, for example, encapsulated biological data units having headers associated with only layer 2, 3 and 4 of the data model. Similarly, other applications may require that the headers of the encapsulated biological data units be arranged in a particular order, e.g., the header for layer 4, followed by the header for layer 1, followed by the header for layer 2.

In a stage 480, the encapsulated biological data units created in stage 480 are stored in a manner consistent with being interoperable with one or more multi-layered, multi-dimensional data containers 464. The content of the headers of the encapsulated biological data units is chosen to promote optimal interoperability among and between layers. For example, in one simplified case each biological data unit included within the data container $464_1$ may include at least a DNA layer header, an RNA layer header, and a protein layer header. It is a feature of the present system that information within higher-layer headers (e.g., RNA layer headers or protein layer headers) may be "mapped" to lower-layer headers and/or sequence information in such way as to establish a relationship provenance between information within various layers.

Consider an example wherein data concerning a particular protein product that is expressed in a certain tissue type (i.e., protein layer information) may also provide information relating to splicing (i.e., RNA layer information) or to a SNP at the genomic level (i.e., DNA layer information) resulting in a premature termination codon. In other words, protein structure related data can provide RNA level knowledge on alternative splicing as well as data on primary sequence data of amino acids substitutions revealing SNPs and indels at in the DNA sequence.

In another case, the diagnosis of a certain disease in a certain patient or, for example, results from a mammogram screen or prostate-specific antigen results, may provide information that is directly related to hyper-methylation of certain regions of the DNA sequence segment included within a DNA layer biological data unit. These epigenetic markers, along with the methylation profile at CpG islands associated with certain genes, could provide crucial header information to relate and correlate with appropriate gene and disease conditions.

One advantage of the layered architecture of the data containers 464 is that modification or updating of the data content associated with a given layer has minimal or no effect on the processing of data in the remaining layers. In one embodiment layers are advantageously designed to be operated on independently while retaining the capability to integrate, and interoperate with, data and existing knowledge of other layers. In addition, data can be organized within each data container 464 in accordance with the requirements of specific applications.

All or part of this data may be mapped, via linked relationships between information within headers or metadata attributes that are associated with different layers of a data model, to a disease condition capable of being associated with a region of segmented DNA sequence data contained within a biological data unit. This enables biological data units to be grouped and analyzed based upon the classification schema required by a particular application.

In a stage 490, biological data units encapsulated with headers and stored with the data containers 464 may subsequently be filtered, sorted or operated upon based on information included within such headers. The layered structure of biological data units comprised of biological data units including encapsulated headers enables querying of the information included within one or more such headers to be performed and results returned based upon a set of rules specified by, for example, the application issuing the query.

Architectural Components of Biological Data Networks

Figure 5:
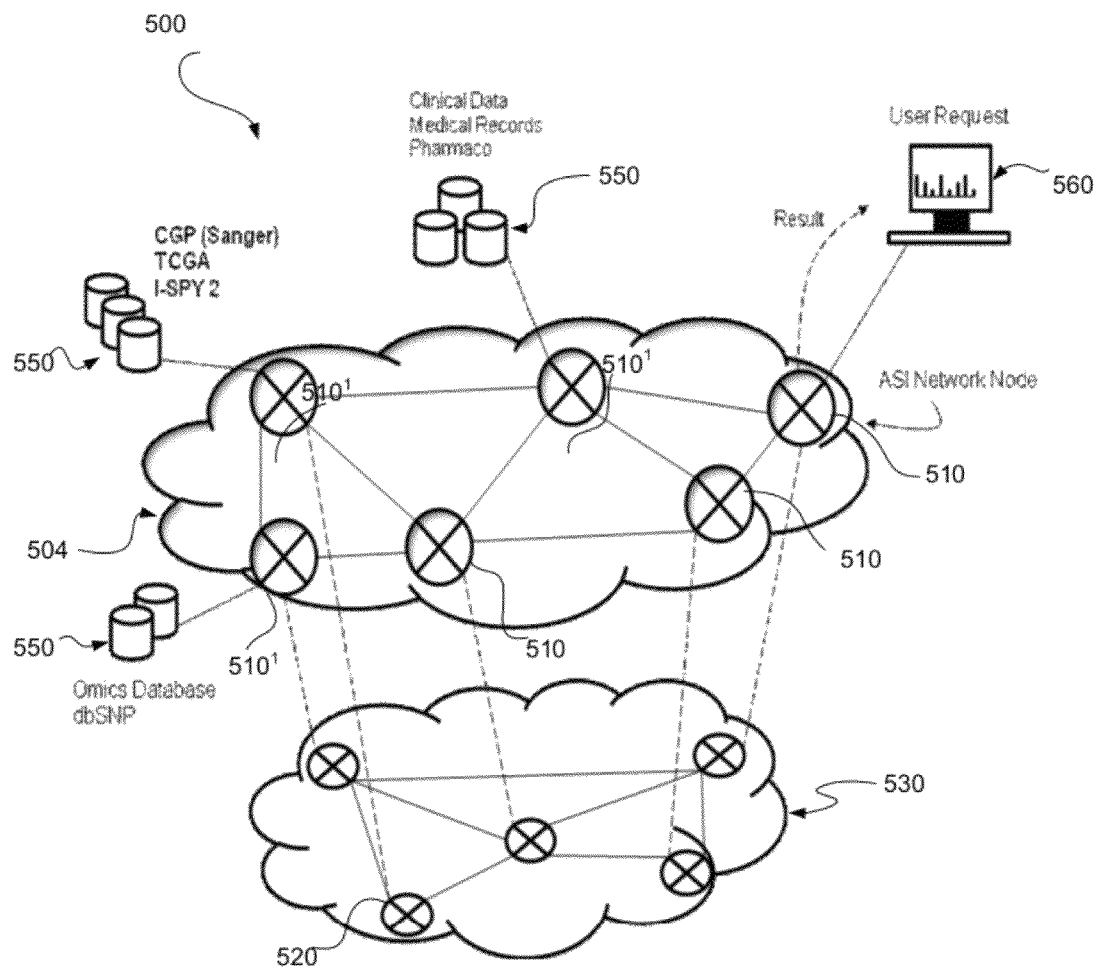
FIG. 5 depicts a biological data network comprised of representations of biological data linked and interrelated by an overlay network containing a plurality of network nodes.

Attention is now directed to FIG. 5, which depicts a biological data network 500 comprised of representations of biological data linked and interrelated by an overlay network 504 containing a plurality of network nodes 510. In one embodiment the network nodes 510 are in communication via network elements 520 (e.g., routers and switches) of the Internet 530 and thus overlay such Internet elements. Certain of the network nodes 510' may have localized access, via a local area network or the like, to databases 550 containing the representations of biological sequence data, clinical data, drug response or other information types which are networked in the manner described herein.

In one embodiment the network nodes 510' may be configured to locally process information within a database 550 and make available all or part of the results of such processing, and potentially information within the database 550 itself, to other of the network nodes 510. In addition, the network nodes 510' may also be designed to perform network processing functions along with the network nodes 510 in the manner described hereinafter.

The biological data network 500 may in one aspect be viewed as comprising a network of data stored within the databases 550 as well as within storage (not shown) at the network nodes 550. In one embodiment each biological data sequence or other sequence information stored within the network 500 may be accorded a unique identifier such as, for example, IP addresses, unique universal identifiers (UUIDs), or tags in order to facilitate the establishment of such a data network. Moreover, tables may be maintained at each network node 510 for data tracking purposes (references herein to network node 510 are generally also intended to refer to network nodes 510', unless the context of the reference clearly suggests otherwise). In particular, such tables may be used to track the sequence information available directly or indirectly (via other network nodes 510) from other network nodes 510, as well as the results of processing such sequence information at various nodes 510. These tables may be updated as biological data units containing sequence information and/or and or MetaIntelligence™ headers are transported between nodes for processing. Alternatively or in addition, overhead messages may be exchanged between network nodes 510 for the purpose of propagating the information stored within ones of these table to the tables maintained by other nodes 510. Such messaging and updating of tables between network nodes 510 generates a type of BioIntelligent™ data awareness that provides a distinct advantage for processing and sharing data on network 500. Furthermore, the network processing that is carried out allows seamless access to network-associated processing functions, shared data as well as support databases that also contain properties of and information about the data.

Structure and Operation of Biological Data Network Nodes

During operation of the network 500, requests from a client terminal 560 are received by a network node 510. Such requests are interpreted at the network node 510 and appropriate processing is carried out at such network node 510, and potentially other network nodes 510, in order to produce the requested results. In this regard metadata attribute information contained in headers are linked to all of the data throughout the network 500 that is designated as or otherwise made network accessible may be accessed and processed in response to requests from a client terminal 560. In this way intelligent information concerning data stored remote from a client terminal 560 and its associated network node 510, and/or such data itself, may be processed in a manner transparent to such terminal 560 and node 510.

Although certain of the embodiments disclosed herein contemplate that various ones of the network nodes 510 may perform specialized processing functions and operate cooperatively to produce an overall processing result, in other embodiments certain nodes may be capable of performing all of the processing functions necessary to deliver results in response to queries.

In certain aspects of the invention whereby cooperative operations and processing functions are coordinated at various distributed network nodes 510 queries can be made that would facilitate the simulation, study and comprehension of systems in biology. In this case, header information fields at the DNA, RNA and protein layers along with query dependent processing function requirements serve as the activated substrates for generating a result.

In general, when a query/request is made, a suite of protocols are invoked which are based upon the properties of the request. For example, a request can be made from any client on the network 500 and the stack of application protocols use processing functions at multiple nodes to access the associated data and a process management function to sort, aggregate, tabulate, coordinate and combine the partial information from multiple nodes to return the query result. In this regard, processing at a network node 510 can be achieved using either of at least two approaches. In a first approach of cooperative processing functions, data and or partial processing results can be moved to the desired functional node 510 to be processed. Alternatively, the required processing function can be moved form a network node 510 to the location of the network accessible data at 550 and the data is processed at the site at which it resides on the network 504. Furthermore, a combination of the two approaches can be used to return the query result to end nodes or terminals 560. In addition, any result from processing that is new network information can be used to update tables at nodes 510 to enhance network awareness.

The network nodes 510 are aware of the types, the content and location of all network accessible data and its intelligence. Moreover, the network nodes 510 are aware of the types, locations and capabilities of processing functions on the network 504. In this regard each node 510 is regularly updated with the activities being performed by, and processing results generated by, each other node 510 of the network 500. In one embodiment, network-based applications and protocols are aware of the information contained in the different fields of the BI headers associated with the biological data units stored within the highly distributed databases 550 and access such information to the extent necessary to process queries from terminals 560.

Figure 6:
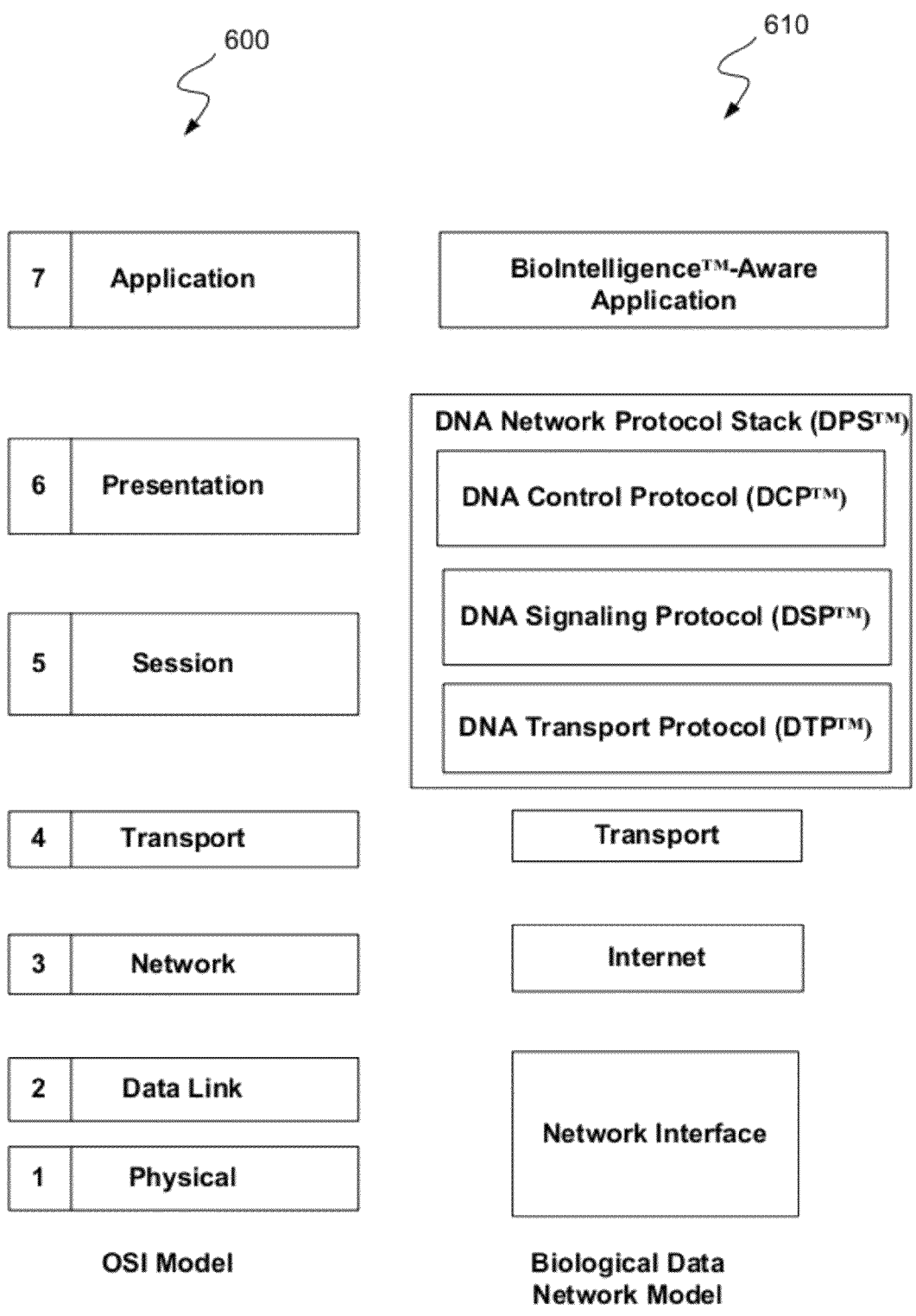
FIG. 6 illustrates an exemplary protocol stack implemented at a network node together with corresponding layers of the OSI network model.

Turning now to FIG. 6, there is illustrated an exemplary protocol stack 610 implemented at a network node 510 together with corresponding layers of the OSI network model 600. As shown, the protocol stack 610 includes a DNA Network Protocol Stack (DPS™) over TCP/IP layers. The DPS™ is consistent with utilization of biological data units and supports a-Aware Network Application capable of processing requests from a client terminal 560 and delivering results. As is discussed below, a network node 510 configured with the protocol stack 610 is capable of performing processing, switching and routing functions based upon not only the information within messages associated with the TCP/IP layers of the protocol stack 610 but also in accordance with the higher-layer information within headers and other information associated with the DPS™. As a consequence, a network node 510 may use this higher-layer information to prioritize the processing of packets received by the network node 510. For example, the network node 510 may control quality of service ("QoS") and effect load balancing based upon this higher-layer information.

The DPS™ is intended to enable existing Internet infrastructure to efficiently process and transport DNA sequence-based data. The DPS™ protocol stack comprises a DNA Transport Protocol™ (DTP™), DNA Signaling Protocol™ (DSP™), and DNA Control Protocol™ (DCP™). In one embodiment the DTP™ protocols enable network elements such as routers and switchers to process, transport, and communicate biological data such as DNA sequence data and related information between single or multiple sources of streaming DNA servers (discussed below). The servers will include or have access to data containers (e.g., storage devices) including biological data units and/or unprocessed or partially processed DNA sequence data.

The functions of the DPS™ protocol suite comprise processing, transporting, controlling, switching and routing biological data such as DNA sequence information as streaming data so as to enable such data to be utilized for a variety of "streaming" applications. In this regard the DPS™ protocol stack will be used for pulling streaming biological data from servers having access to containers of biological sequence data. Such streaming applications are capable of continuously "pushing" and "pulling" biological sequence data and the high level abstracted information from this data as necessary to support the functionality of each particular application.

Various options exist for introducing the DPS™ protocol suite into existing network infrastructure. In one implementation, for example, the DPS™ protocol suite may be distributed throughout the routers/switches of a given service provider. In another implementation, the DPS™ protocol suite may reside only in one or more network elements near an edge of the service provider's network in an overlay network.

Figure 7:
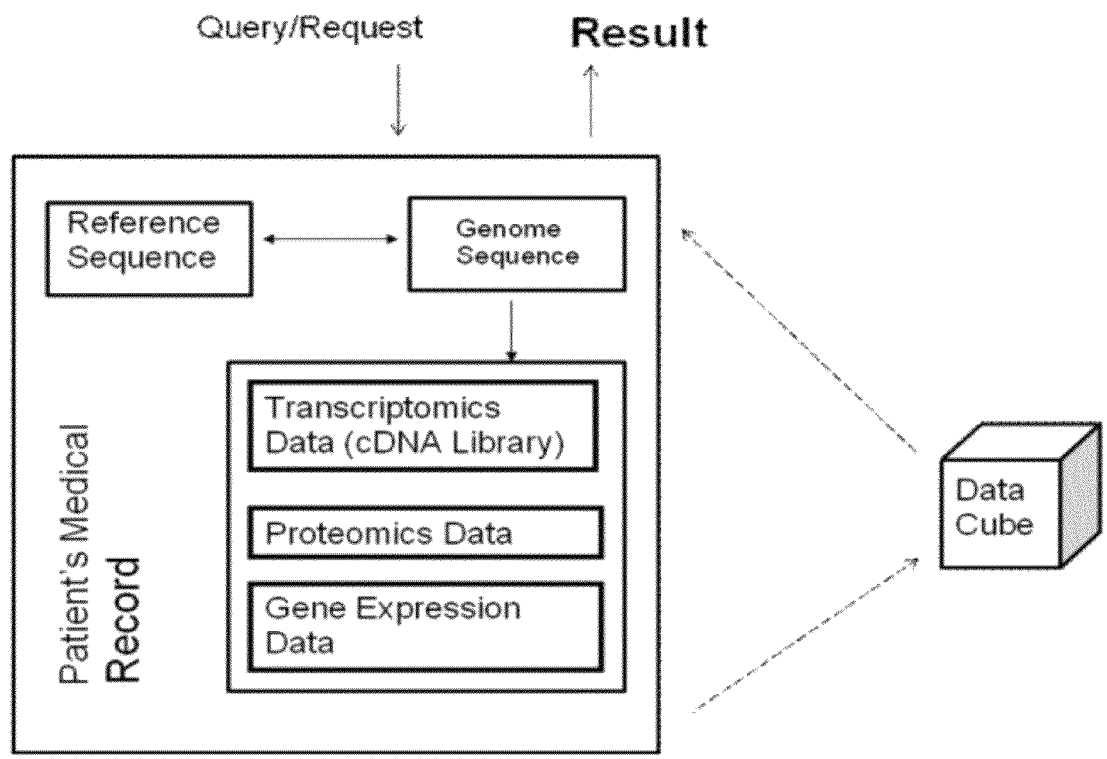
FIG. 7 shows a high-level view of various data types that may be processed by a group of network nodes in response to a query/request received from a client terminal.

FIG. 7 shows a high-level view of the various data types that may be processed by a group of network nodes 510 in response to a query/request received from a client terminal 560. As shown, transcriptomics data, proteomics data and/or gene expression data along with a patient's medical record information is a small sample of the type of data that may be stored as biological data units within databases or data containers accessible to the nodes 510 may be processed.

FIG. 7 illustratively represents a query request message being sent to a network controlled by an "operating system" of protocols and programs. Such a network operating system is capable of processing the request by using biological data units consisting of the metadata attributes that are associated with distributed sequence data accessible on the network. The system is able to locate, aggregate, sort and filter the highly distributed but linked data units and sent a response to the query request.

In addition, the "data cube" represents one or more databases of all the prior knowledge that may be associated with the biological data units that are aggregated based on a query. The information that is contained in the existing knowledge base (data cube) will be stored in a manner consistent with the concepts of a data model disclosed herein.

Figure 8:
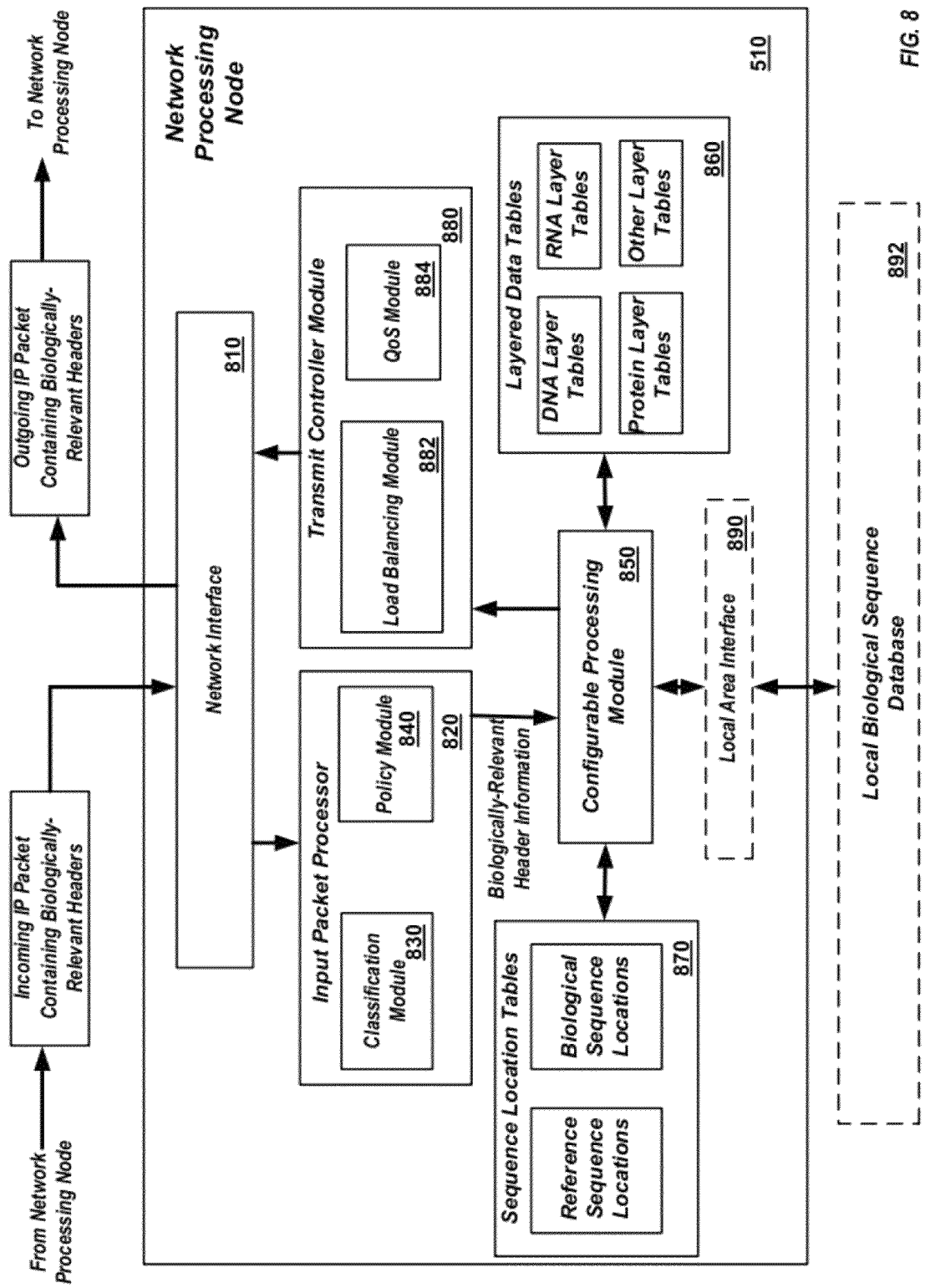
FIG. 8 provides a block diagrammatic representation of the architecture of an exemplary network node.

Attention is now directed to FIG. 8, which provides a block diagrammatic representation of the architecture of an exemplary network node 510. As shown, the network node receives incoming IP packets containing BioIntelligent™ biologically-relevant headers. Encapsulated within such incoming IP packets will typically be, for example, information identifying the particular segments of genome sequence data with which such biologically-relevant headers are known, calculated or predicted to be associated with. Such information could include, for example, the particular chromosome and position within the chromosome with which the gene is associated, protein information associated with the gene, whether any part of the sequence of the gene corresponds to a normal or minor allele, or other information pertinent to the gene including association with any disease or phenotype or drug metabolism information. In addition, each incoming packet could also include information uniquely identifying the specific DNA sequence or other biological sequence information and the network location at which such sequence is stored.

For example, such identifying information (which could be in the form of, for example, an IP address separate from the IP address of the incoming IP packet) could identify a particular network-accessible database and a location or position with such database. In other embodiments both information identifying the gene associated with the biologically-relevant headers within the incoming IP packet and information specifying a particular location at which the sequence information associated with such headers is stored could be inherent within a unique identifier included within the incoming IP packet.

Each incoming IP packet containing biologically-relevant headers is received via a network interface 810 and provided to an input packet processor 820. In one embodiment the network interface is comprised of a physical port in communication with an external network and further includes, for example, buffers, controllers and timers configured to facilitate transmission and reception of packetized sequence data and other information over such network. The input packet processor 820 removes the IP header information and parses the higher-layer content included within the packet. A classification module 830 may then assign the packet to a particular class based upon this higher-layer content. The biologically-relevant header information included within the packet may then be passed to a configurable processing module 850 for processing in the manner described hereinafter based upon the determined class and any policies applicable to such class defined by policy module 840. As is also described hereinafter, the biologically-relevant header information may then be processed by configurable processing module with reference to various sequence location tables 870 and layered data tables 860 maintained at the network node 510. The layered data tables 860 are structured consistently with the biological data model (FIG. 2) used to define the biologically-relevant headers within each incoming IP packet.

Based upon the results of the processing performed by the configurable processing module 850, outgoing biologically-relevant header information associated with the biological sequence identified within the input IP packet or other processing results is provided to a transmit controller module 880 for packetization within an outgoing IP packet. To the extent the outgoing biologically-relevant header information requires further processing by another network node 510 in order to render an appropriate response to the user request received by the network 500, a load balancing module 882 within the transmit controller module 880 selects such a network node 510 from among the group of such nodes capable of performing the required processing. Such selection may be based upon, for example, the processing loads associated with each node within the group. Additionally, selection may be based upon processing results that are passed to the transmit controller module 880. A QoS module 884 places each outgoing IP packet in one or more queues in accordance with, for example, the applicable class accorded the corresponding incoming IP packet by the classification module 830 and the policy associated with such class. Each outgoing IP packet will generally include identifying information similar to that included within each incoming IP packet. The outgoing IP packets are provided by the transmit controller module from the applicable queue to the network interface for transmission to a destination network node 510.

In one embodiment the headers within each IP packet received by a network node 510 will be functionally associated with or contain information having biological relevance to a segment of DNA sequence data, MetaIntelligence™ metadata, or both. It should be appreciated that the headers may be arranged in any order, whether dependent upon or independent of any associated payload data. However, in one embodiment the headers are each respectively associated with a particular layer of a biological data cube model representative of the biological sequence data contained within the payloads of the biological data units with which such headers are associated. Moreover, it should be understood that any patient-related data which is not predicated upon genomic sequence information but is nonetheless pertinent to the processing by the network 500 of a request may be included within the headers of a received IP packet.

It should be further understood that BI headers may be realized in essentially any form capable of embedding information within, or associating such information with, all or part of any biological or other polymeric sequence or plurality thereof. BI headers may also be placed within a representation of associated DNA sequence data, or could be otherwise associated with any electronic file or other electronic structure representative of molecular information. In particular, biological data units containing segmented DNA sequence data may be sorted, filtered and operated upon based on the associated information contained within the header fields.

Figure 9A:
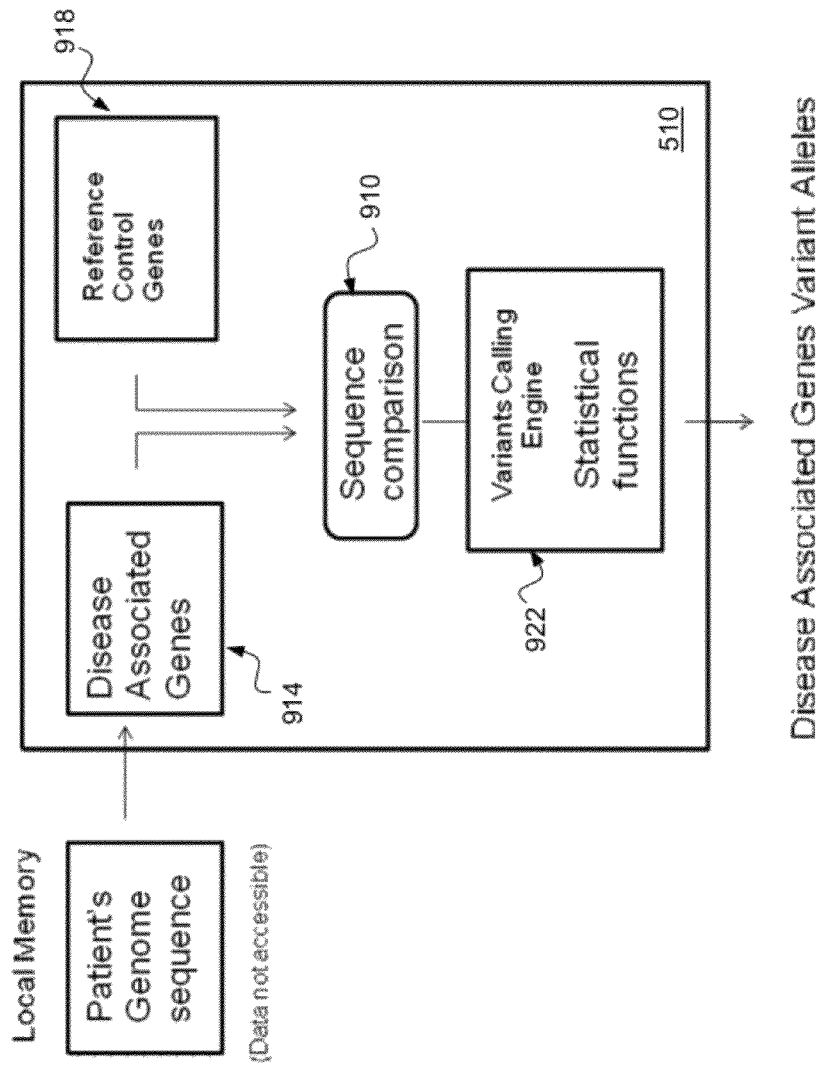
FIG. 9A illustratively represents a process effected by a network node to implement a sequence variants processing procedure.

Attention is now directed to FIG. 9A, which illustratively represents a process effected by a network node 510 to implement a sequence variants processing procedure. In many instances the first process performed within the network 500 in response to receipt of a user query is the execution of a variants calling function at a network processing node 510. The variants calling function may be executed at the network node 510 receiving the user query. Alternatively, the procedure may be executed at a network node 510 specially configured for performing a comparative analysis of the subject patient whole or partial genome sequence against the selected reference/control sequence.

In an initial step of the variants processing procedure, a determination is made as to whether any differences exist between the biological data sequence associated with the query and the reference sequence. To the extent differences are detected, the nature of the differences and their locations with respect to the reference sequence are recorded. In this regard the sequence data associated with the query could comprise a portion of a gene or plurality of genes, an entire genomic sequence from normal cells, and/or an entire genomic sequence from diseased cells. The sequence data for a particular patient could comprise any, or a combination, of these types of sequence data.

In other embodiments a clinically transformed version of a patient's genomic sequence data, rather than the sequence data itself, is associated with user requests received by the network 500. Such a clinical transformation may involve, for example, associating a patient's medical records or health related information with any or a combination of the patient's genomic sequence or the patient's transcriptomic, proteomic, metabolomic or lipidomic information, or any other such related data. For example, such transformation could involve using certain minor allele variations in or near certain genes that are associated with certain phenotypes, symptoms, syndromes, diseases, disorders, etc. Furthermore, certain knowledge of the linkage disequilibrium that is associated with the haplotype map genome sequence of the patient might provide a detailed transformation of this genotyping data into information on protein concentrations in blood, urine and other body fluids. Information on functional activity of these proteins and their metabolic state which might include posttranslational modifications could be a useful part of improving the granularity of the patient's genomic-based transformed data. Accordingly, the present disclosure advantageously provides a mechanism for networking and sharing genomic-based data without requiring a corresponding sharing of a patient's genomic sequence data.

Again considering the process of FIG. 9A, in a comparison operation 910 packets of genomic sequence segments 914 are mapped to corresponding portions of a reference sequence 918. In an operation 922, statistical corrections are then carried out at the network node 510 on the basis of the comparison in order to make a variant call. Variants calls can be checked against a database of variant alleles since each node has awareness of such data location on the network. For example, a rare variant in a certain gene associated with breast cancer might be contained in TCGA database with pertinent information on drug response. This information will have information on clinical responses to certain drugs that relate directly to the minor allele. The network can access the TCGA database and extract the required information for processing on the network or locally at the client server.

For simplicity, in the case where SNPs are the only variants dbSNP can be used to validate common SNPs. In addition, data on minor alleles with disease association might be present in other cancer genome databases that are maintained by public and private entities such as but not limited to CGP (Cancer Genome Project at Sanger Institute), TCGA (at NIH's National Cancer Institute), RCGDB (Roche Cancer Genome Database), and the like.

Figure 9B:
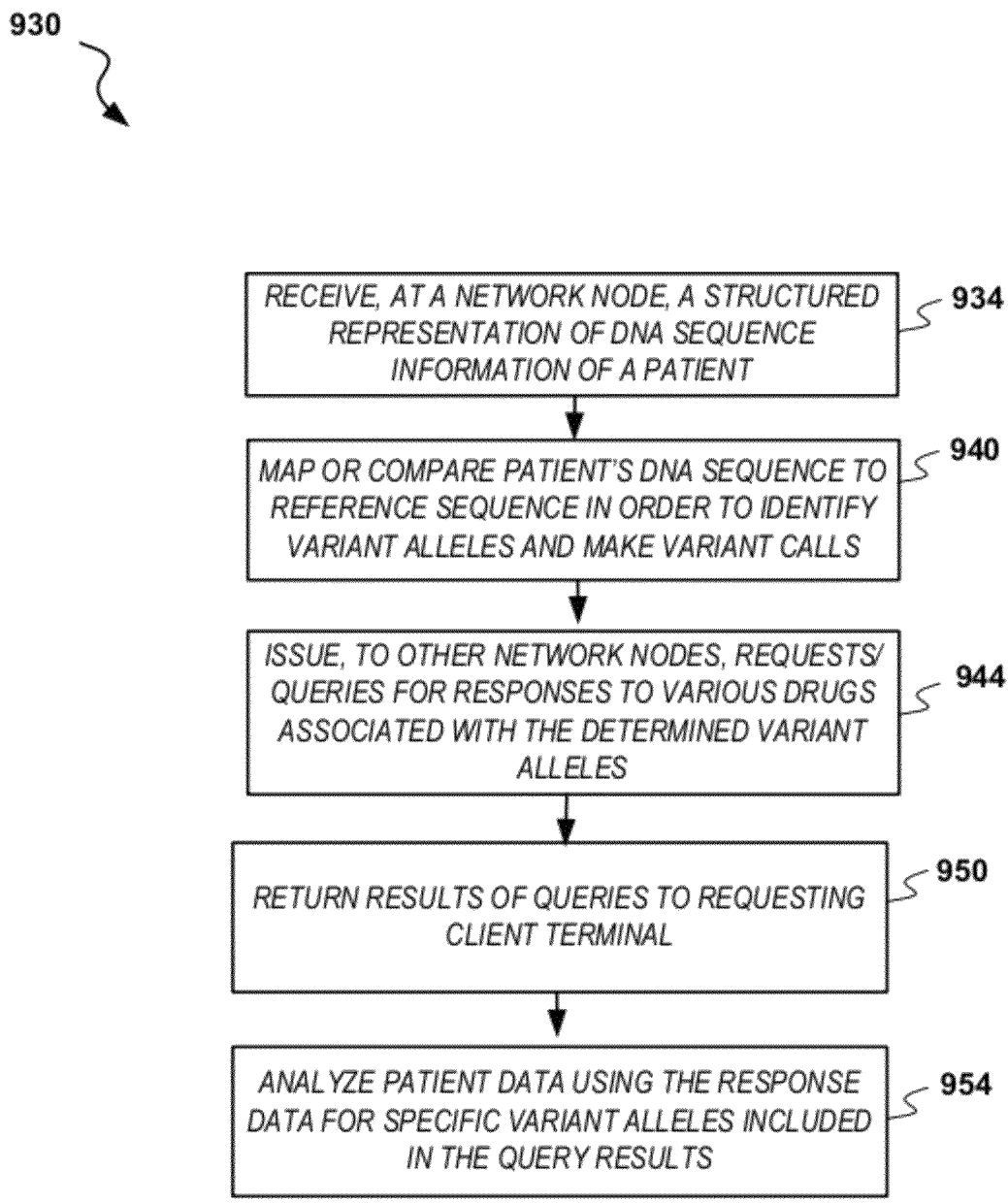
FIG. 9B is a flowchart of an exemplary variants processing procedure.

Attention is now directed to FIG. 9B, which is a flowchart of an exemplary variants processing procedure 930 representative of one manner in which a network node 510 configured for variants processing may be utilized in connection with processing a particular user request. In particular, consider the case in which a structured representation of the DNA sequence data of a breast cancer patient is received at a network node 510 configured for variants processing along with a reference sequence (stage 934). The structured sequence data is then mapped against the reference in order to produce the specific variant alleles forming the basis of variants calls made by the node 510 (stage 940). In this example it is assumed that the request accompanying the sequence data comprised a request to determine the pharmaceutical drug with the highest efficacy and with lowest toxic effects in view of the DNA sequence data of the patient. Once the specific variant alleles of the patient have been determined, the network node 510 configured for variants processing may issue a query/request that is processed by those network nodes 510 having access to public and private databases containing information relating to pharmacogenomics-based responses to various drugs (stage 944). The results of such queries may then be returned to the requesting client terminal 560 (stage 950), and the drug response data for specific variant alleles included within such results may then be used for analysis of the patient data (stage 954).

In the general case, once the processing to be performed at a given network node 510 has been completed, a decision will be made to route or switch the processing to another network node 510 based upon the results of such processing (stage 960). The extent of the processing to be performed by the network 500 with respect to a particular request will of course be dependent upon the nature of the request.

Figure 10:
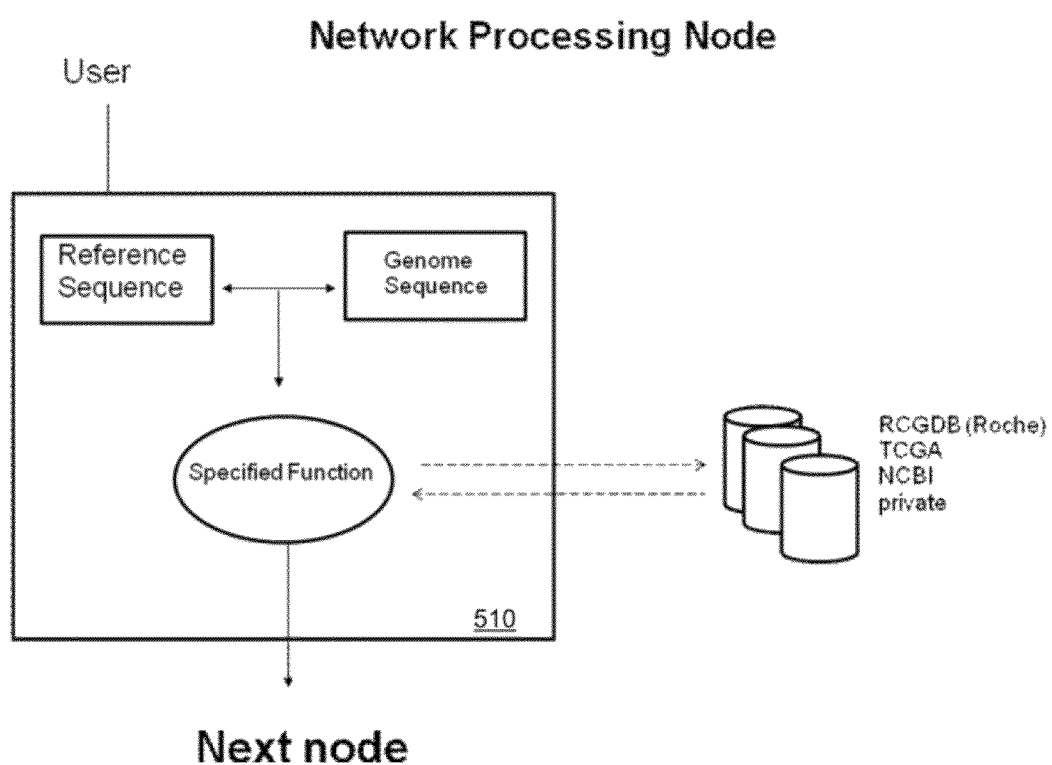
FIG. 10 illustratively represents the processing occurring at a network node configured to perform a specialized processing function.

Turning now to FIG. 10, an illustrative representation is provided of the processing which occurs at a network node 510 configured to perform a specialized processing function. As may be appreciated with reference to FIG. 10, a specialized processing function which is required to be performed is first carried out and the result of such a processing function is supported by access to public and private databases with relevant associated data.

In one embodiment each network node 510 implements a method which generally involves performing a processing operation involving ones of a first set of biological data units and a second set of biological data units. The processing might further involve a comparison of the called variant with access to established variants databases.

In the general case, the biological data unit encapsulated within the IP packet received by a network node 510 will contain a first header associated with first information relating to segmented biological sequence data and a second header associated with second information relating to the segmented biological sequence data. The method includes processing of the first information and the second information in relation to the content of the payload of the biological data unit. In one embodiment processing is carried out at each network node 510 with respect to biological data units including a first header associated with information relating to a first-layer representation of biological sequence data and a second header associated with information relating to a second-layer representation of biological sequence data wherein a biological, clinical, pharmacological, medical or other such relationship exists between the first-layer and second-layer representations. For example, the DNA sequence for a gene may be related to the cDNA or RNA sequence of that gene or the protein sequence, structure or function of the gene product. In one embodiment all of the data contained within a layered representation of the DNA sequence information (see FIG. 2) would be available for a subset of patients at each client server.

As may be appreciated with reference to FIG. 2, a biological data unit predicated upon the layered data model of FIG. 2 includes a transformed representation of a biological sequence and a first header associated with first information relating to such sequence. Since the headers included within such a biological data unit may generally correspond to the layers of the layered data structure of FIG. 2, it should be understood that a processing node 510 that operates on a given layer of data will typically be able to access only a certain type of data. For example, in one embodiment "layer 1" headers are associated with the DNA layer and a network node 510 configured for "layer 1" processing would access DNA-related data.

Figure 11:
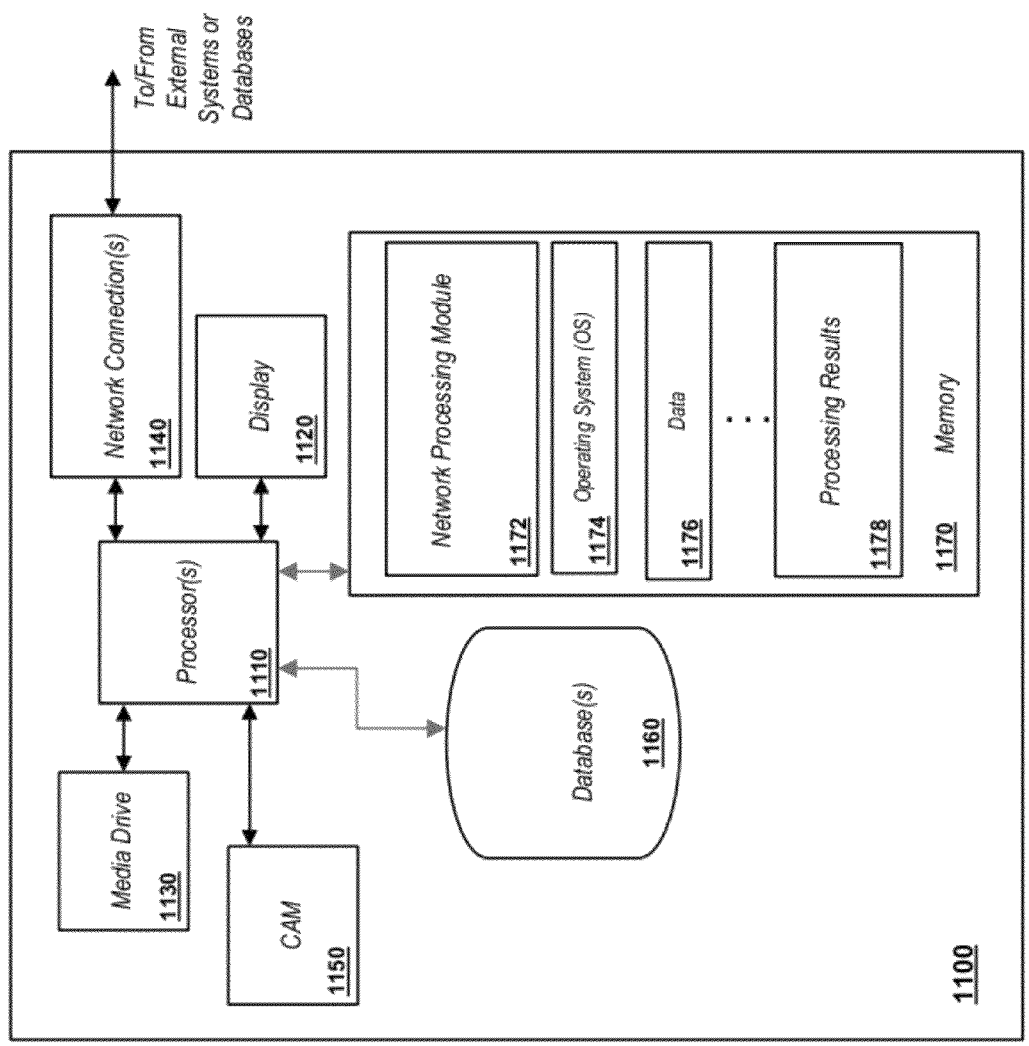
FIG. 11 provides a representation of an exemplary processing platform capable of being configured to implement a network node.

Attention is now directed to FIG. 11, which provides a representation of an exemplary processing platform 1100 capable of being configured to implement a network node 510. The processing platform 1100 includes one or more processors 1110, along with a memory space 1170, which may include one or more physical memory devices, and may include peripherals such as a display 1120, user input output, such as mice, keyboards, etc (not shown), one or more media drives 1130, as well as other devices used in conjunction with computer systems (not shown for purposes of clarity).

The platform 1100 may further include a CAM memory device 1150, which is configured for very high speed data location by accessing content in the memory rather than addresses as is done in traditional memories. In addition, one or more database 1160 may be included to store data such as compressed or uncompressed biological sequences, dictionary information, metadata or other data or information, such as computer files. Database 1160 may be implemented in whole or in part in CAM memory 1150 or may be in one or more separate physical memory devices.

The platform 1100 may also include one or more network connections 1140 configured to send or receive biological data, sequences, instruction sets, or other data or information from other databases or computer systems. The network connection 1140 may allow users to receive uncompressed or compressed biological sequences from others as well as send uncompressed or compressed sequences. Network connection 1140 may include wired or wireless networks, such as Etherlan networks, T1 networks, 802.11 or 802.15 networks, cellular, LTE or other wireless networks, or other networking technologies are known or developed in the art.

Memory space 1170 may be configured to store data as well as instructions for execution on processor(s) 1110 to implement the methods described herein. In particular, memory space 1170 may include a network processing module 1172 for performing networked-based processing functions as described herein. Memory space 1170 may further include an operating system (OS) module 1174, a data module 1176 configured to temporarily store sequence data and/or associated attributes or metadata, a module 1178 for storing results of the processing effected by the network processing module 1172.

The various modules included within memory space 1170 may be combined or integrated, in whole or in part, in various implementations. In some implementations, the functionality shown in FIG. 11 may be incorporated, in whole or in part, in one or more special purpose processor chips or other integrated circuit devices.

Figure 12:
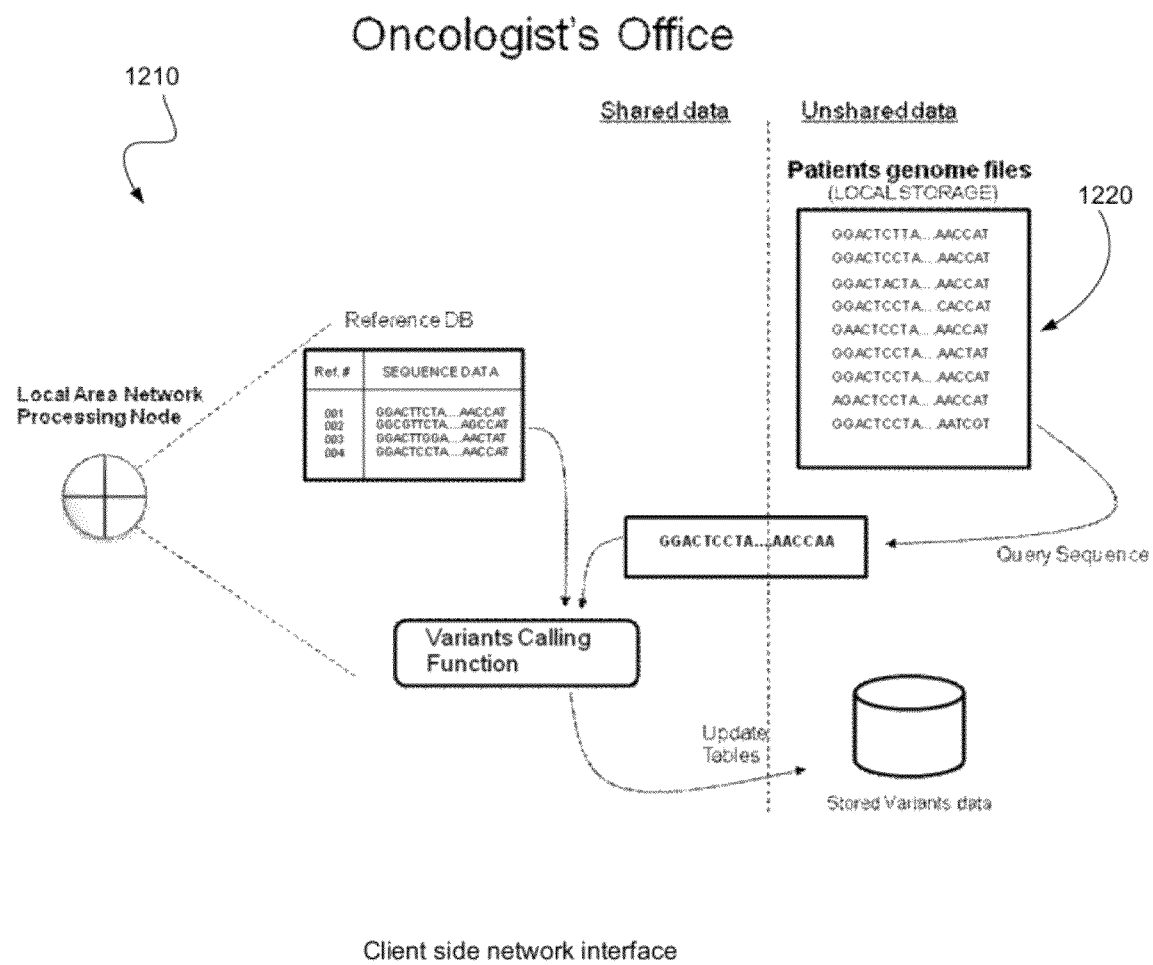
FIG. 12 illustrates one manner in which data may be processed, managed and stored at an individual network node in an exemplary clinical environment.

Attention is now directed to FIG. 12, which illustrates one manner in which data may be processed, managed and stored at an individual network node 510 in an exemplary clinical environment. In particular, FIG. 12 depicts one way in which the information technology systems of a medical provider (e.g., an oncologist) could interface with network processing at a node 1210 included within a local area network in communication with the data network 500. In one embodiment the network processing node 1210 may have similar or identical processing functionality as the nodes 510 of the network 500 and would be in communication with at least one such node 510, but could also be locally networked with other information technology infrastructure in a campus environment not part of the network 500.

In one embodiment none of the data which is stored in the local storage container 1220 is generally accessible to clients 560 of the network 500. Movement of data between storage containers associated with or accessible to different network nodes 510 may be governed by the policies established by the one or more clients 560 controlling such containers. For example, depending on the policy in place at a first network node 510, certain aspects of actual patient data or a transformed version of such data might be "pulled" in whole or in part from data containers accessible to a second network node 510.

Access to Existing Knowledge

Attention is now directed to FIGS. 13-18, which illustratively represent the manner in which information within the layered data structure 200 is utilized at an individual network processing node 510. In particular, each of FIGS. 13-18 depict an exemplary representation of the relationship between information in the headers 1304 of a biological data unit associated with a query message and prior knowledge 1308 within storage accessible to the node 510 that is used in generating a response to the message. It should be understood that FIGS. 13-18 provide only one example of a set of three layers of a BI header information or metadata attributes which are directly associated with the various layers of the knowledge structure.

As may be appreciated by reference to FIGS. 13-18, the first field of information present within each BI layer header specifically relates to a first source of data and/or knowledge associated with such BI header. For example, the fields within the "layer 1" header 1310 will relate directly with a first layer of the structured knowledge data model. In this case the fields within the layer 1, or "L1" header 1310 can relate with L1 data (i.e., DNA-related data in the case of the data model 200). Consequently, information that is contained in the fields of the layer 2, or "L2", header relate directly but not strictly with the data presented in the second layer or the RNA layer data and knowledge presented in that layer.

Figure 13:
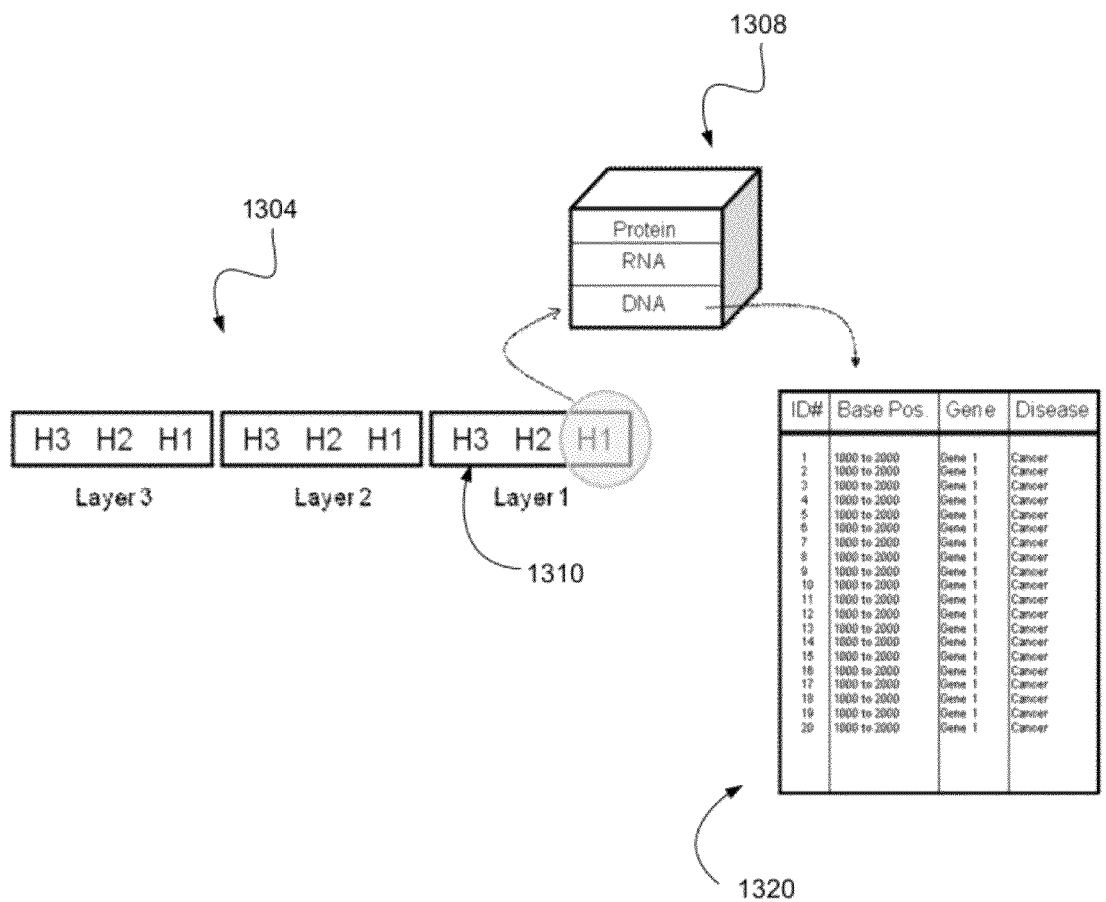
FIGS. 13-18 illustratively represent the manner in which information within the layered data structure is utilized at an individual network processing node.

Referring now specifically to FIG. 13, "H1" represents a first of the information within the L1 set of attributes that represent header 1310 of a given data packet. In the example of FIG. 13 the particular attributes within section L1 header 1310 directly correspond to characteristics of the first layer (i.e., the DNA layer 210) of the layered model of existing related knowledge 200.

It should be noted that FIG. 13 depicts only the different layers of headers and the various header information fields, and not any associated payload of segmented sequence data, of a particular biological data unit. As discussed above, IP packets based upon a particular biological data unit which is exchanged between network nodes 510 may or may not include such payload data (i.e., such IP packets may only include higher level abstracted attribute information corresponding to the biological data unit).

In the embodiment of FIG. 13, the header field H1 within the L1 header 1310 relates to a particular type of information pertinent to the DNA layer 210. For example, as indicated by DNA-layer table 1320 maintained by the individual network processing node 510, the field H1 within the L1 header 1310 may point to the base positions for a sequence of genomic data within the payload of the biological data unit containing headers 1304. The layered prior knowledge that is being accessed or related or pointed to by attributes such as H1 is specifically associated with DNA layer information of data 1308.

The segmented sequence data within the payload of the biological data unit identified by the field H1 within the L1 header 1310 may represent a certain region of a genome that may be positioned in similar but not necessarily identical base positions. For example, the comparison of this region or section of the genome that is represented in the payload for a particular gene would be expected to code for the same genes or at least different isoforms of the same gene.

As a result, the effect of L1H1 header field (layer 1, header field 1) from the stored DNA data would give comparable results for the various DNA layer annotations that are present in that data container. Such DNA layer information could include, for example, gene ID, chromosome, base positions, regulatory regions, 5' and 3' UTR, variant alleles and other DNA-based information related to the gene. Based on the query message, the individual network processing node 510 accesses information within data cubical of prior knowledge 1308 relating to, for example, chromosome number (for simplicity, not shown) and base positions identified by the L1H1 header field.

Figure 14:
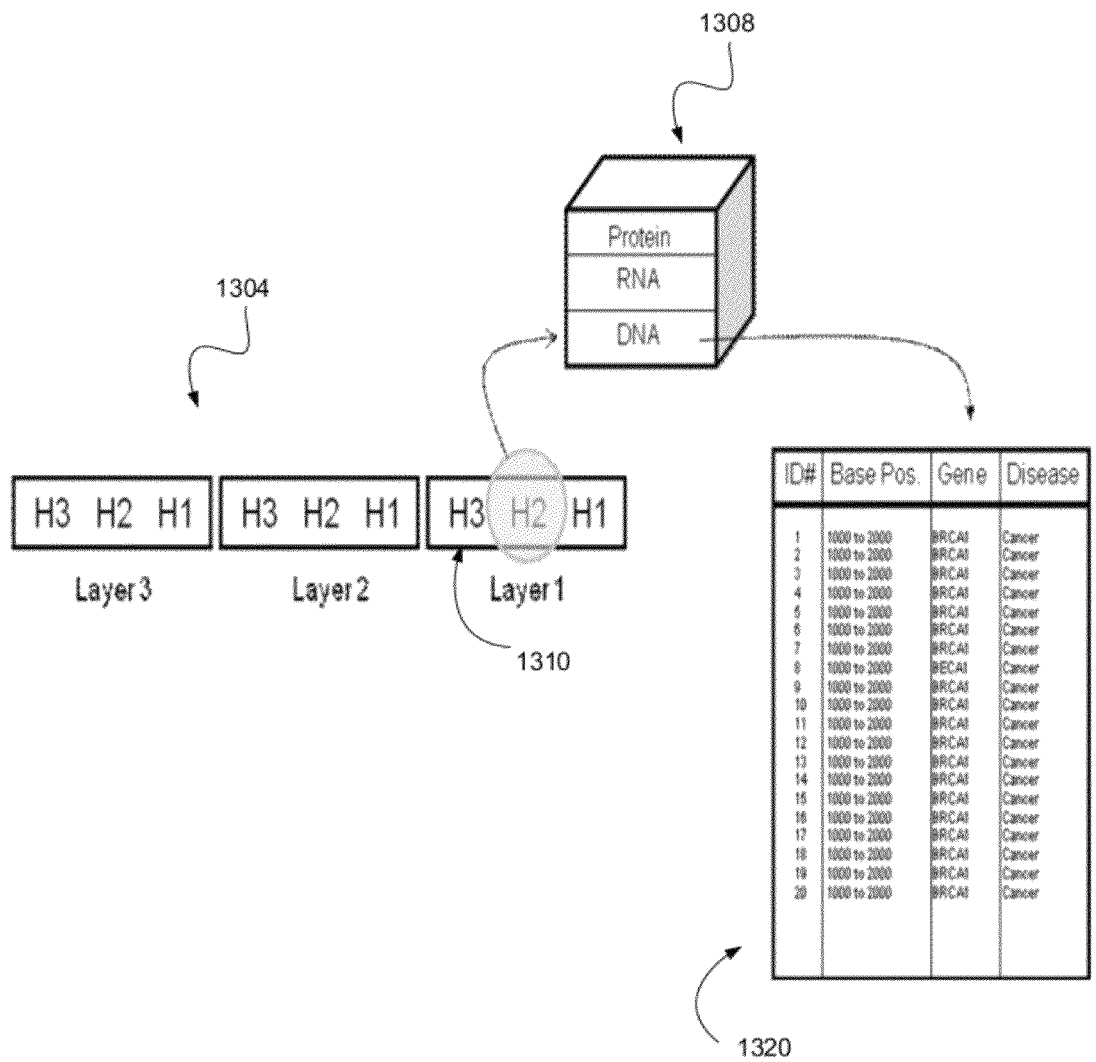

Referring now to FIG. 14, "H2" represents a second attribute of header information within the L1 header 1310 of the certain data packet (i.e., the "L1H2" header field). In this case, the L1H2 header field refers to a second field in the DNA layer that points specifically to the associated gene or gene product related to the packetized segment of DNA sequence data within the biological data unit associated with headers 1304. Such sequence data could, for example, code for one gene, a plurality of genes or a part of a gene (represented in either the + or − orientation based on the 5' to 3' direction of the sense strand). As indicated by FIG. 14, the L1H2 attribute field relates or points to the gene ID section of the distributed network-accessible data 1308.

In one embodiment this field should contain at least one representation for the name of the gene and or gene product that is encoded by the DNA sequence in the payload of the biological data unit associated with headers 1304. In cases where more than one name is used to identify a gene, gene product or the activity associated with that gene the most current and widely accepted names are listed. Any gene ID name that is used to relate specifically to the sequence represented by the chromosome number and base positions that are indicated in the first header field of the layer 1 should be encoded by this particular sequence in this region of the genome. However, because of gene duplication, copy number variations, existence of gene families, repeat sequences, mobile transposable elements and other such related molecular phenomena certain classes of redundancy will exist. Furthermore, one gene or the polypeptide product of a gene or the enzymatic activity of a gene could be associated with more than one disease, syndrome, disorder, phenotype, etc.

Figure 15:
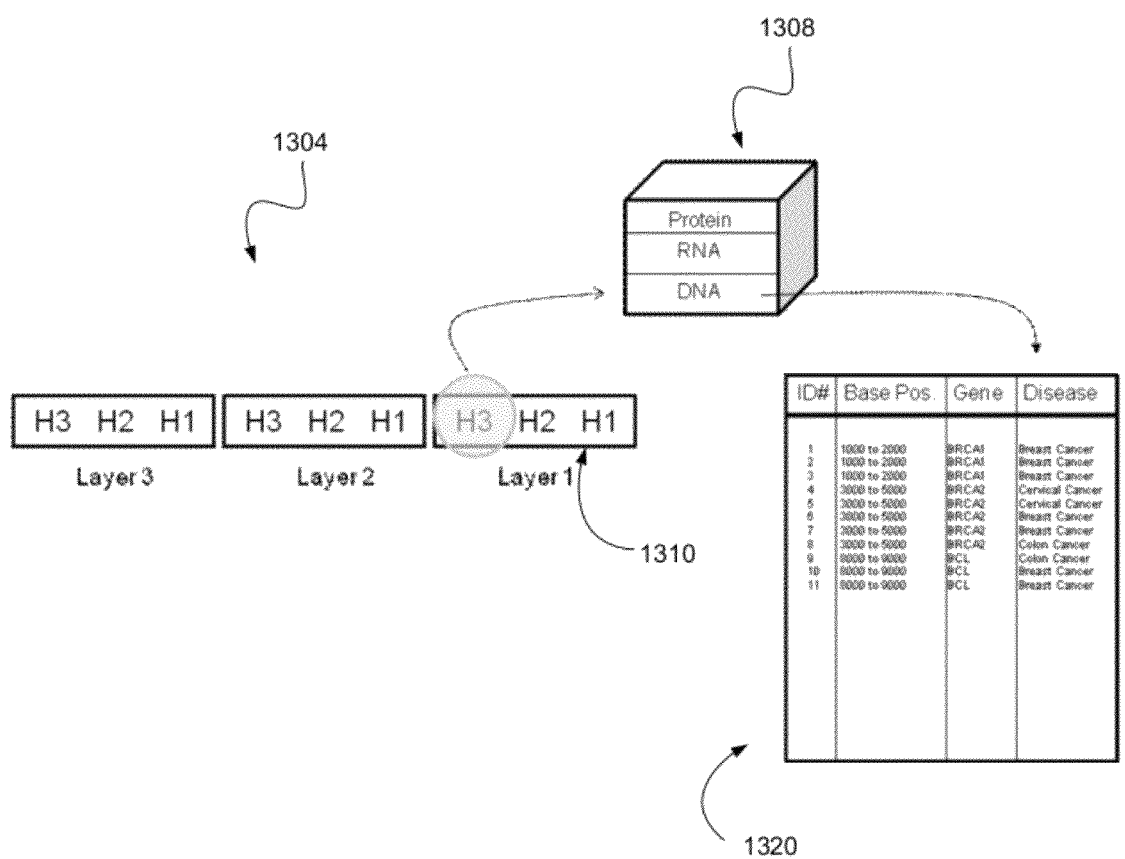

Turning now to FIG. 15, "H3" represents a third field of header information within the L1 header 1310 of the certain data packet (i.e., the "L1H3" header field). In this case, the L1H3 header field relates to any phenotypic expression of encoded gene that is associated with a disease or disorder. That is, in the example of FIG. 15 the L1H3" header field points to disease(s) known or predicted to be associated with the gene, a mutated or variant form of the gene, or an expressed gene product.

For simplicity and clarity, the supportive data in this case show three different cancer types that are associated with packaged genome sequence data attached to the exemplary header fields. The diseases that are known to have association with the segmented sequence in the payload of this biological data unit in this case are colon, cervical and breast cancers. The gene or sequence segment might represent an up-regulated oncogene or proto-oncogene, a down-regulated tumor suppressor gene or a structural or functional gene involved in a pathway with other genes associated with the disease.

Figure 16:
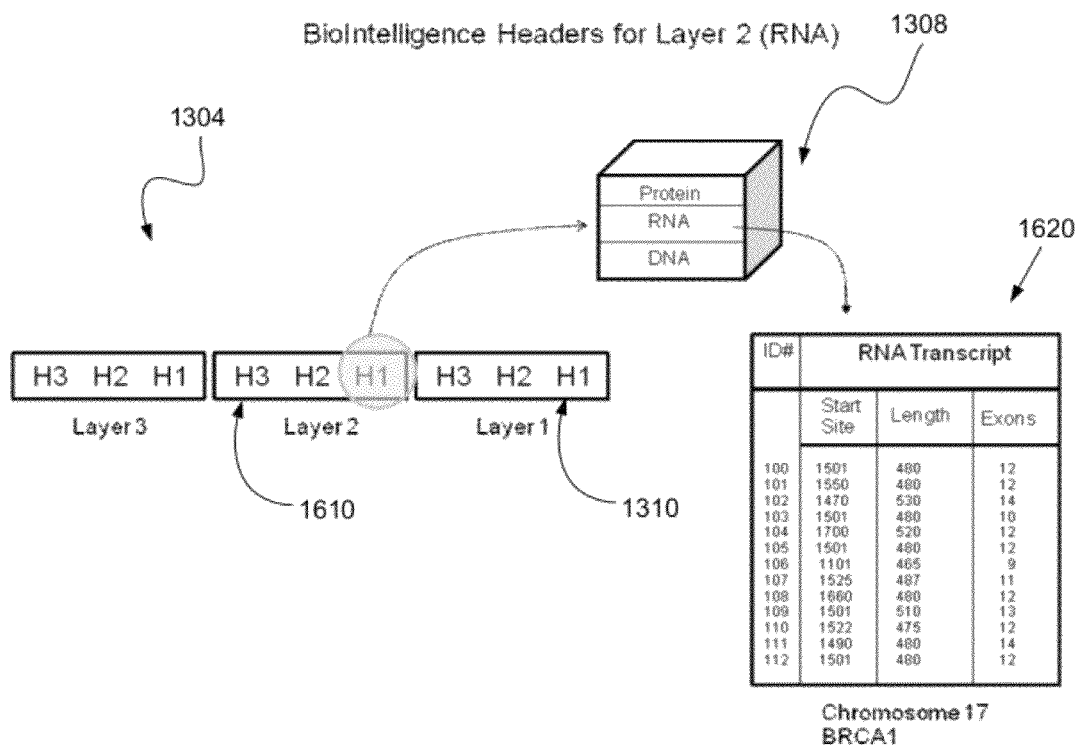

Referring now to FIG. 16, a first field of information within the L2 header 1610 of the certain data packet is denoted by "H1". In the example of FIG. 16 the header fields within the L2 header 1610 directly correspond to characteristics of the second layer (i.e., the RNA layer 210) of the layered data model 200. It should be appreciated that network access to the data that relates to the diseases associated with any packetized segment of DNA sequence data will be through a layer 1 (DNA layer) access. Access to data associated with other layers, e.g., layer 2 and layer 3, will require access to information associated with the header fields of layer 2 or layer 3. That is, the header fields associated with the L1 header 1310 will generally relate only to data in the DNA layer 210 of the layered data structure 200, the header fields within the L2 header 1610 will relate only to data within the RNA layer 220, and so on. Such RNA-layer data related to a gene of interest could include, for example, the lengths of the pre-mRNA and mature mRNA, exon selection, alternate splicing, data on differential expression of RNA, transcription control and any RNA-related information.

As shown in FIG. 16, fields within the L2 header 1610 relate to the RNA layer 220 of the layered data structure 200. For example, in the embodiment of FIG. 16 the H1 field may relate to the transcription start site of the mRNA for the gene identified by fields of the L1 header 1310. In other words, the transcription start site information included within the RNA layer 220 would relate to the chromosomal position of the gene. It should be understood that all of the information and field data in FIG. 16 is exemplary, and none of such information actually relates to any information concerning any particular gene. For instance, where BRCA1 might be used to indicate a gene and chromosome 17 the chromosome, all of the information in the related table 1620 is exemplary. Thus, information within the RNA layer 220 and the DNA layer 210 are associated and interrelated by layered data structure 200 in a manner that allows independent access to the different information and or data types or layers.

Figure 17:
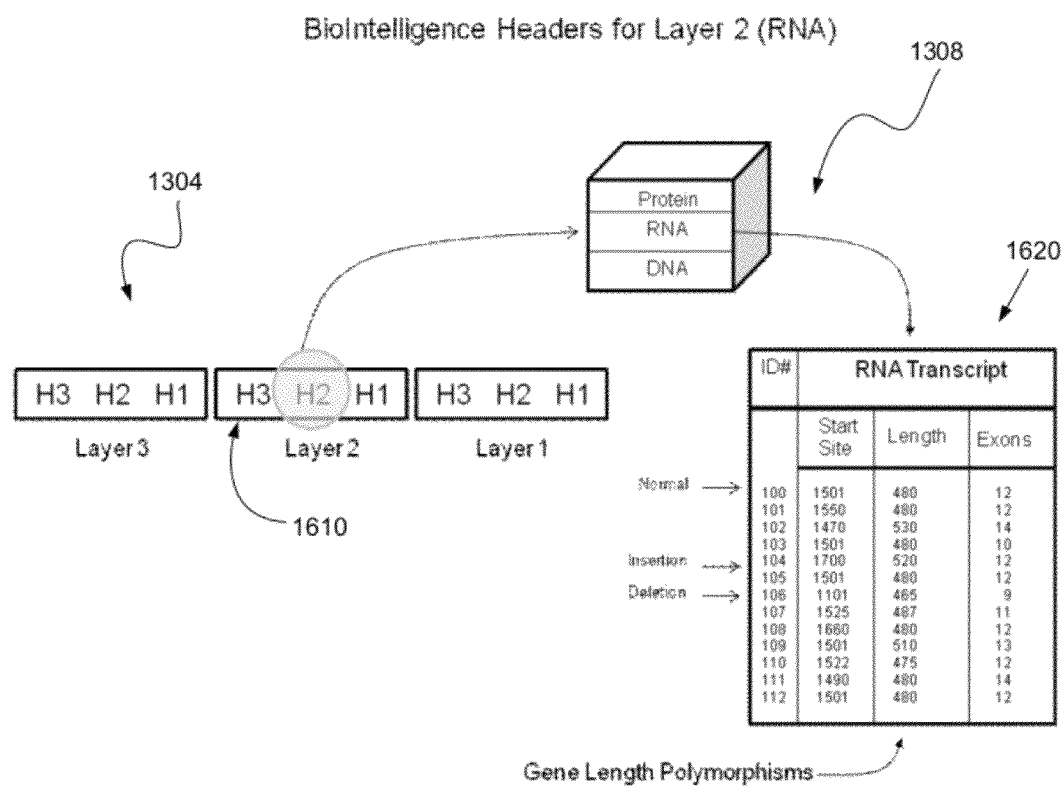

Attention is now directed to FIG. 17, in which "H2" represents a second field of header information within the L2 header 1610 of the certain data packet (i.e., the "L2H2" header field). In this case, the L2H2 header field relates to RNA-layer information pertaining to the length of a transcript. The RNA data on this particular gene shows a variety of lengths for the transcript. Entries that harbor an insertion show relatively longer transcript length; conversely, the shorter length transcripts show deleted bases in comparison with the normal case.

Figure 18:
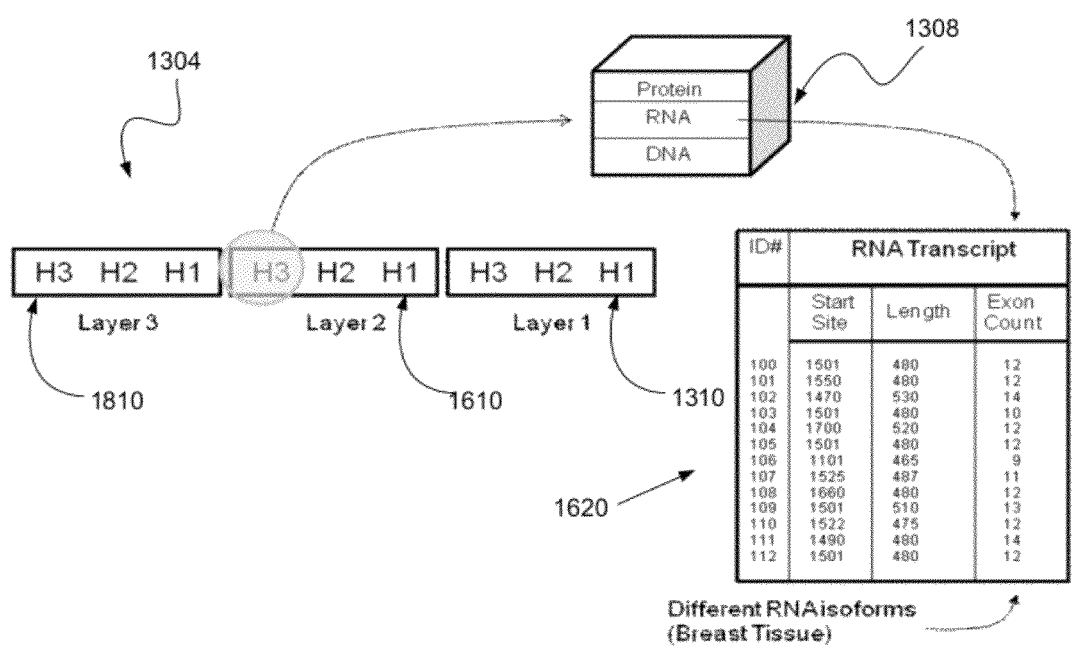

Referring now to FIG. 18, the third field ("H3") of header information within the L2 header 1610 may relate to other information associated with the RNA layer 220. For example, this "H3L2" header field may relate to the exon selection of a gene associated with breast cancer.

In this example, the variations in the number of exons that are contained in this gene indicate the existence of different splice variants that are associated with the transcripts from cell taken from the breast tumor tissue. The defect in splicing could be from variants of the gene or some component of the splicing mechanism.

In the embodiment of FIG. 18, layer 3 ("L3") headers 1810 may include information associated with a protein layer of the data model 200. Such protein-layer information may include, for example, the molecular weight of the protein product of the gene identified by the L1 header 1310, amino acid count and content, expression level, activity, posttranslational modifications, structure, function and other related information.

Although FIG. 18 does not explicitly depict the relationship between the fields of the L3 header 1810 and corresponding portions of the data cubical 1308, such fields are related to the protein-layer data within cubical 1308 in a manner consistent with that described above with respect to DNA-layer and RNA-layer information.

Figure 19:
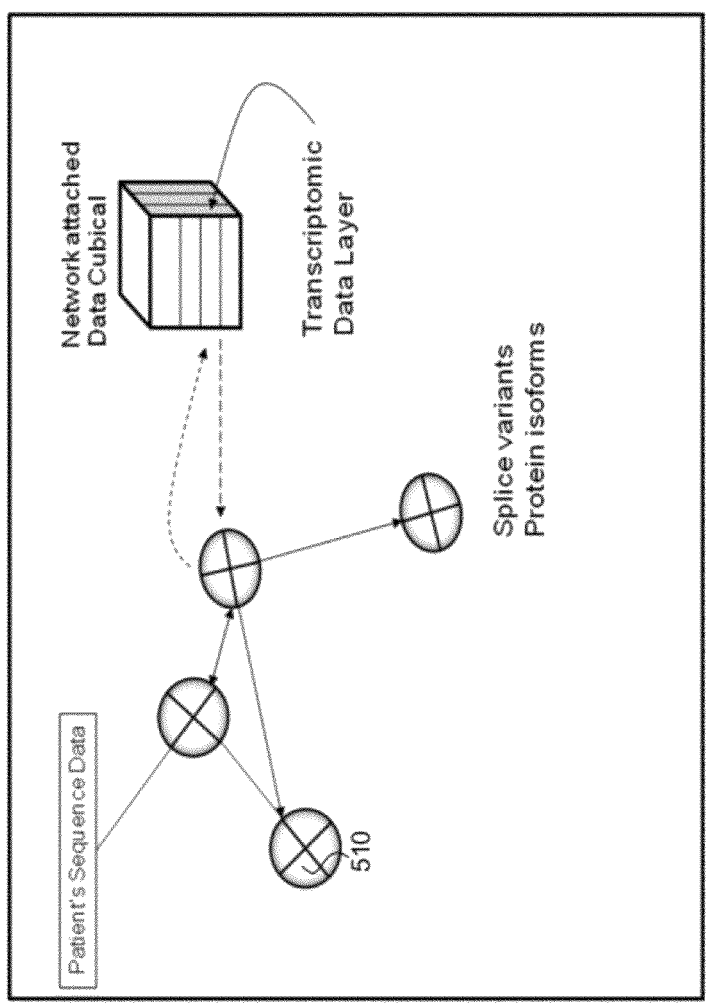
FIG. 19 illustrates the cooperative performance of an exemplary result-based network processing using multiple network nodes.

Attention is now directed to FIG. 19, which illustrates the performance of an exemplary result-based network processing operation involving the cooperation of multiple network nodes 510. As discussed above, messages will generally be regularly exchanged between network nodes 510 in order to update tables identifying the biologically-relevant data and other information accessible to each such node 510 as well as the processing capabilities of each such node 510. In addition, when certain processing operations are completed at a network node 510, the results of such processing may be used to update various tables maintained by the node 510. In one embodiment such processing results are evaluated to determine the type, if any, of further processing is required in view of the applicable client request. To the extent it is determined at a current node 510 that further processing is required, tables at such current node 510 may be consulted in order to identify a subsequent node 510 capable of performing the required additional processing. The current node 510 may then forward a set of partially processed data to the subsequent node 510 for further processing.

As a simple example of such result-based processing, consider a request message that requires processing at multiple nodes 510 on the network 500. Depending on the query and the headers that are assigned or associated with the patient-based or other data related to the query, partially-processed results are passed to successive nodes 510 as processing is completed at each such node. In the case in which the initial processing at a current node 510 requires performing operations with respect to a header corresponding to the DNA layer 210 of the data model 200, information pertinent to the layer 210 may be retrieved from memory or storage accessible to such current node 510. Such network-accessible memory or storage may include a layered data model of related prior knowledge containing biologically-relevant information organized in a manner consistent with the data model 200. To the extent it is determined based upon the results of this initial processing that access is required to information relevant to the RNA layer 220 of the data model 200, then such information may also be retrieved from the network-accessible storage. The result from this data access function could return a simple categorical binary response (zero or one).

Consider the case where access to the second layer is to determine if there are any alternative splicing associated with the phenotype or disease. The disease could be one of the many molecular classifications of breast cancer and the drug target for treatment could be specific functions of splicing or kinase function for example. The first of two molecular functions might be targeted by a first class of drug and the second molecular function might be the target of a second class of drug. Both of these drugs would normally be treatment of choice for this patient whose genome and medical data was used to make the query. The patient might fall in a certain category based on age, weight, tumor cell morphology, tumor size and position as well as other social, environmental and physical aspects to place the patient and disease in a category. However, the type of genomic variants that gives rise to the molecular cascade of events that characterize the onset of the disease may involve certain molecular targeted activities.

For example, in the case where a mutation affects a transcription factor binding site to up the over expression of a gene associated with many cancers versus a minor allele variant that is known to cause alternative splicing resulting in a protein product associate with the disease onset and progression. Different classes of drugs that target certain molecular pathways or functions or activities will be more suitable for treating certain diseases and the ability to be able to discriminate between them would improve treatment selection.

Again referring to FIG. 19, consider the processing occurring at a current network node 510 where access to the RNA layer is a necessary path for the request message to return a result. In this case associated data is retrieved from network-accessible storage containing a data cubical organized consistent with the data model 200 in order to facilitate comparison or other processing of RNA-layer information. If the result of such RNA-layer data access and processing at the current node 510 indicates, for example, a splice variant, then a next node 510 selected to performed the processing steps subsequently required would be different than the node 510 selected had the initial processing indicated that there was no alternate splicing involved. Moreover, in the case where the response indicated alternate splicing the subset of drug selections for final results would be different from those listed when the splice variant query is returned as null.

In one embodiment a path of a query request may involve execution of a limited number of preferred processing steps selected based upon specific characteristics of the query. For example, the network application may monitor the results of processing at a particular node 510 and then determine which of a number of possible successive processing steps is most consistent with returning the best available results based on the characteristics of the data accessible to the network 500.

Figure 20:
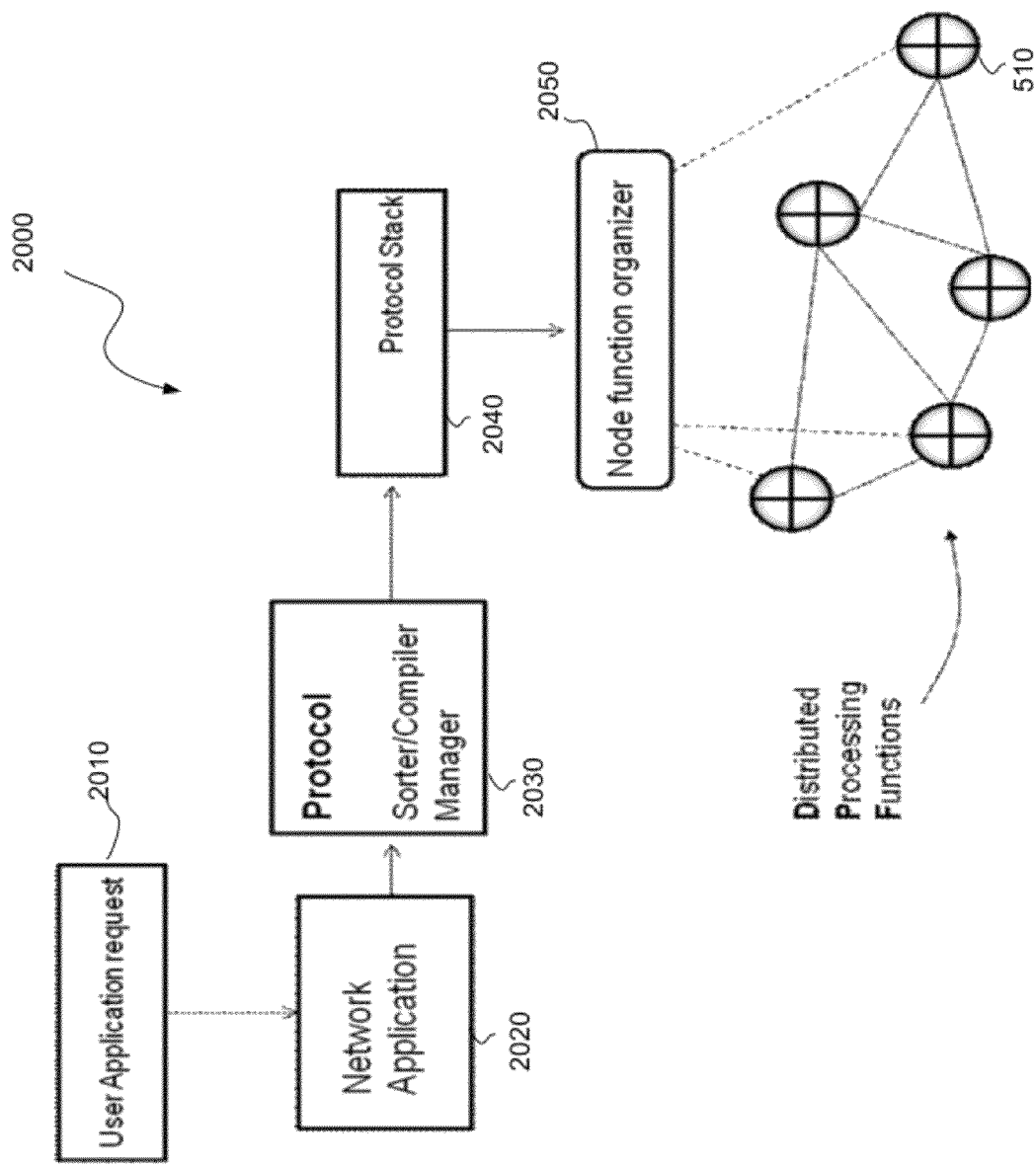
FIG. 20 illustrates an exemplary process flow corresponding to the result-based network processing illustrated by FIG. 19.

Turning now to FIG. 20, there is illustrated an exemplary process flow 2000 corresponding to the result-based network processing discussed above. As shown, a request message 2010 is sent by a user application executing on a network client 560. The network application 2020 the message 2010 activates a set of protocols associated with processing the message sent from the user application. Protocols are compiled and sorted by a protocol sorter/compiler manager 2030 and a representative stack 2040 which is consistent with the processing of the user application request is selected. The suite of protocols that is required to process the message includes a set of processing functions that are performed at each network node. Nodal functions are organized and updated constantly by a node function organizer 2050. In particular, the organizer 2050 selects and configures a set of network nodes 510 to effect distributed processing of the set of required network functions.

In one embodiment the processing functions executed by the network nodes 510 are highly distributive; that is, each network node 510 performs one specialized function and thus functions are distributed throughout the network. The network application message management and processing function engine coordinate the widely distributed network nodes to perform a system function using MetaIntelligence. As is explained below, a function organizer is adapted to select a sequence of nodes to effect a set of distributed functions to be performed in processing a message or request from a client 560.

In one embodiment the network 500 may be regarded as operate as a system in which multiple nodes 510 will be configured to be of capable of performing particular processing functions. That is, the network nodes 510 would generally be configured such that the frequency and distribution of the available processing functions would be selected based upon prior usage. As a consequence, a relatively large percentage of network nodes 510 could be configured to implement those functions most often required in connection with generation of a result in response to a request message; conversely, a relatively small percentage of network nodes 510 could be configured to implement those functions least often required in connection with generation of a result in response to a request. For example, depending on the usage load of processing functions at certain high volume network node the updating messages sent between nodes can be used for load balancing and congestion control. As a result, network recommendations can be made based on nodal usage to provide updated node functions to optimize the network.

Figure 21:
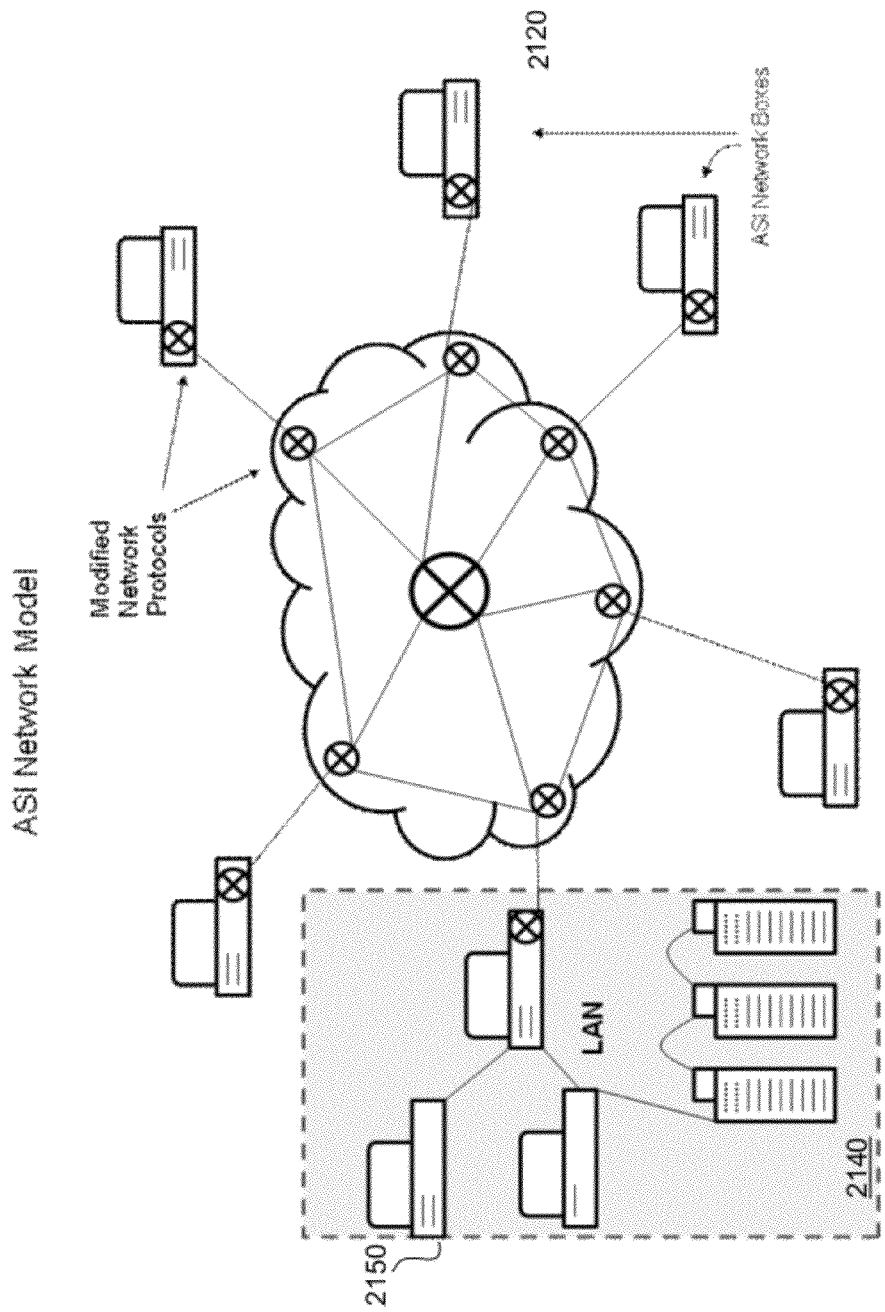
FIG. 21 depicts a biological data network comprised of a plurality of network nodes.

Attention is now directed to FIG. 21, which depicts a biological data network 2100 comprised of a plurality of network nodes 2110. In one embodiment each of the network nodes 2110 is substantially similar or identical to each network node 510. Similarly, the network nodes 2110 form an overlay network and communicate by way of IP packets delivered through the Internet (not shown in FIG. 21). A plurality of network-associated devices 2120 are configured to send messages to the network 2100 to receive updated data and result information in response to such messages. Each device 2120 may also structure any data provided to the network 2100 consistent with the layered data structure 200 utilized by the network 2100.

During operation of the network 2100, a user application executing on a device 2120 will determine a set of processing functions which are required for responding to a request message. This determination will generally require interaction between the user application and the protocols that are running on the network. In one embodiment frequent "push and pull" between user application 2340 and the user net software 2350, coupled with frequent updating of information at the network nodes 510, enables an approximation of required functionalities to be made based on a combination of factors. For example, such an approximation could be predicated upon knowledge of previous query messages, available data, and available network functions.

As shown in FIG. 21, a local area network 2140 contains a plurality of processing devices 2150 and a network-associated device 2120' in communication with the network 2100. The processing devices 2150 may be connected in a manner by which access to the network can be achieved through at least the network-associated device 2120'. The single network-associated device 2120' will generally regularly communicate with the plurality of network nodes 2110 and can broadcast messages over the network 2100 sent from any user in the local area network 2140.

Figure 22:
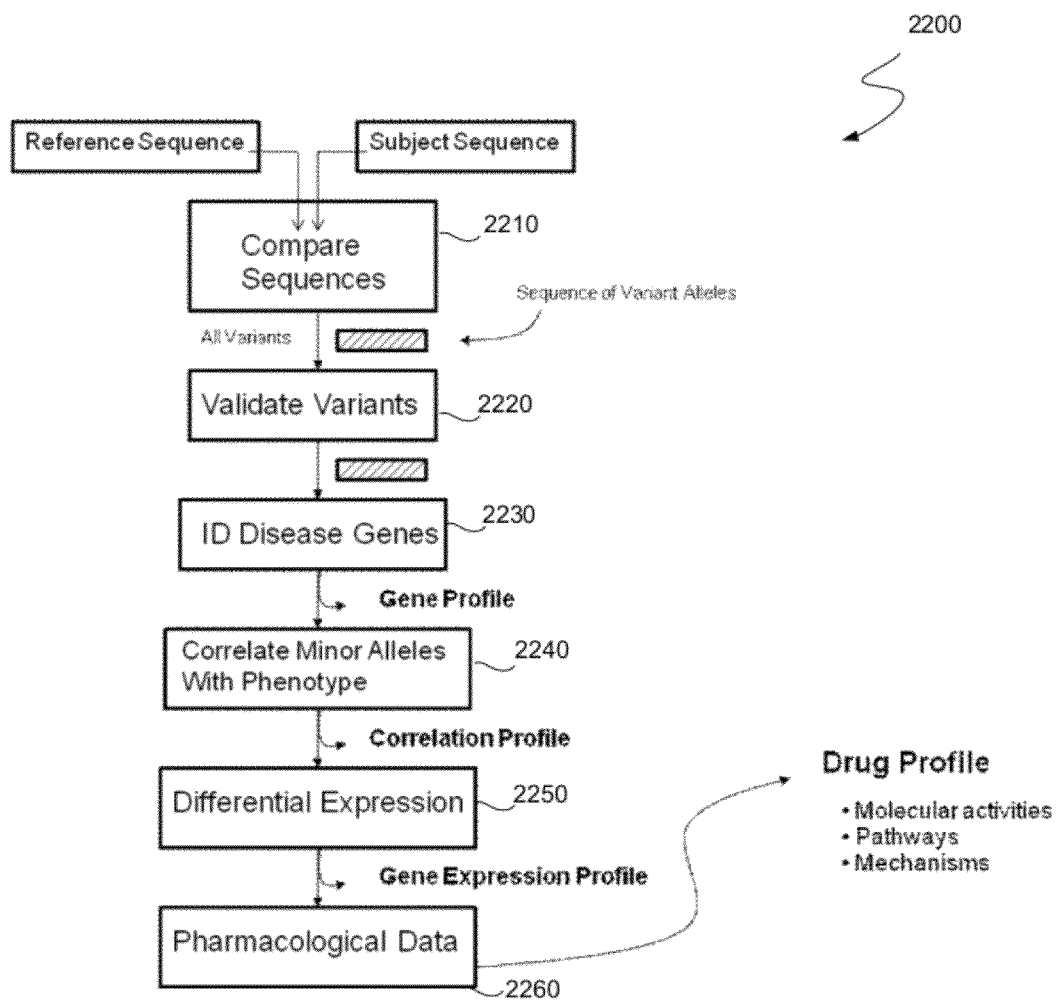
FIG. 22 is a flow chart representative of a set of exemplary processing operations performed by a biological data network in response to a user query or request.

Attention is now directed to FIG. 22, which is a flow chart 2200 representative of a set of exemplary processing operations performed by the biological data network 500 in response to a user query or request. In a stage 2210, at least one subject sequence is received at a first network node 510 and compared to a reference sequence. This comparative sequence analysis can be done locally (i.e., at the first network node 510), or at another network node 510.

In one embodiment a result of this sequence comparison is a large file of minor alleles with relation to the reference sequence. The variants can range from single nucleotide polymorphisms to larger insertions, deletions, reversions, translocation, chromosomal rearrangements, mobile elements, and the like. Initially, all the variant alleles are arranged sequentially based on position in the reference sequence. In a stage 2220, these variants are matched or otherwise validated against a database of known and implicated variant alleles for at least one disease, phenotype, symptom, biomarker, etc.

The list of variants alleles that have been validated are used to isolate genes that are associated with the onset, progression or prognosis of a disease (stage 2230). In this case, the locus for a trait can fall within the coding region or regulatory region or in introns associated with a gene. The gene profile has disease specificity and along with the information on the particular variant alleles that are characterized validated in the genome of this patient, the gene profile becomes very personalized. Statistical analytical functions may be performed to generate a correlation profile between the validated variant alleles and various phenotypes, symptoms, biomarkers, scans, scores etc. that are associated with the disease condition (stage 2240).

Differential gene expression data and clinical results from various pharmacological drug studies may then be used to generate a drug efficacy and toxicity profile (stage 2250). Based on the results of the gene profile, correlation profile and gene expression profile, a particular molecular classification could be accorded to a patient so as to enable a health care provider to develop various clinical profiles. For example, a drug profiling scheme could be developed for the patient in order to facilitate selection of more effective treatments (stage 2260). For example, rather than treating a disease based exclusively on symptoms, drug selection may be made based on molecular-level clinical profiles such that drugs targeting a specific molecular activity, mechanism or pathway could be selected based upon such profiles.

Figure 23:
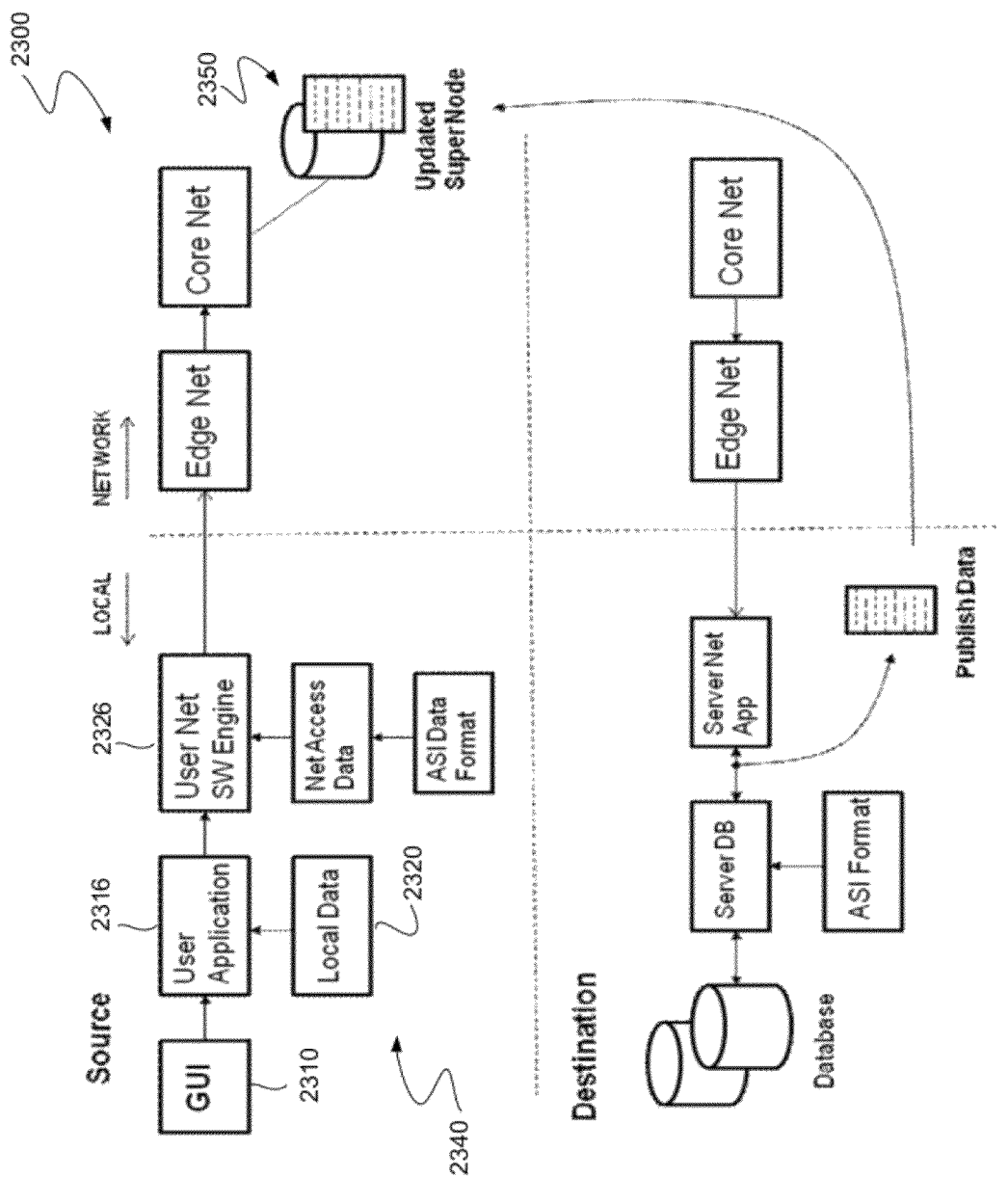
FIG. 23 illustratively represents a separation of localized and network-based processing functions within a portion of a biological data network.

Turning now to FIG. 23, an illustration is provided of the separation of localized and network-based processing functions within a portion of a biological data network 2300. During operation, a user may make a request through a graphical user interface ("GUI") 2310 generated by a user application 2316 utilized to access local data 2320 and other application software. As the local data 2320 is operated upon by the user, a user network software engine 2326 monitors the activities of the user and determines if the outcome of the operation may be useful to other users on the network. The network accessible data at the local source is converted to a normalized to a format consistent with, for example, the biological data model 200. For example, the network accessible data may comprise a plurality of biological data units containing a payload including a segment of biological sequence data and a set of headers associated with the sequence segment.

In this case the sequence data could comprise actual, "raw" sequence data, or sequence data represented in an instruction format as described in the above-referenced copending patent applications. Alternatively, the network accessible data could include only the header information associated with a collection of biological data units. In this case the sequence data comprising the payloads of such sequence data could, for example, remain stored only within local data 2320. This arrangement advantageously permits the selective sharing of various characteristics of a collection of sequence data without permitting access to the sequence data itself.

The network software engine 2326 evaluates the request message and is able to intelligently distribute the required processing functions between the local server 2340 and one or more network nodes 510. For example, to generate a list of variant alleles relative to a reference sequence, the comparative sequence analysis yielding a list of variants could be performed on the local server 2340. The list of variants could then be validated using one or more network nodes 510 to access relevant databases and broadcast results for updating network nodes.

In one embodiment nodes 510 at the edge of the network 500 use applications to communicate and update core network elements. The information about the data that is accessed at the various network nodes 510 may be transmitted between nodes 510 as a result of the functions and the inherent awareness of the network 1810 to biologically-relevant information.

It should be understood that a source or user node in one instance can access multiple network node and associated databases at various destinations. However, in another instance the previous source can serve as a destination for network processing functions and biologically relevant information concerning the requested data ( ).

Certain information that is learned, updated, stored or otherwise made accessible based on a query might be published or broadcast on the network 500 based on a previous request for the specific or related data. For example, when a query relating to a new drug is processed by the network 500, the result of the query could be used to update a multi-function super node 2350.

Figure 24:
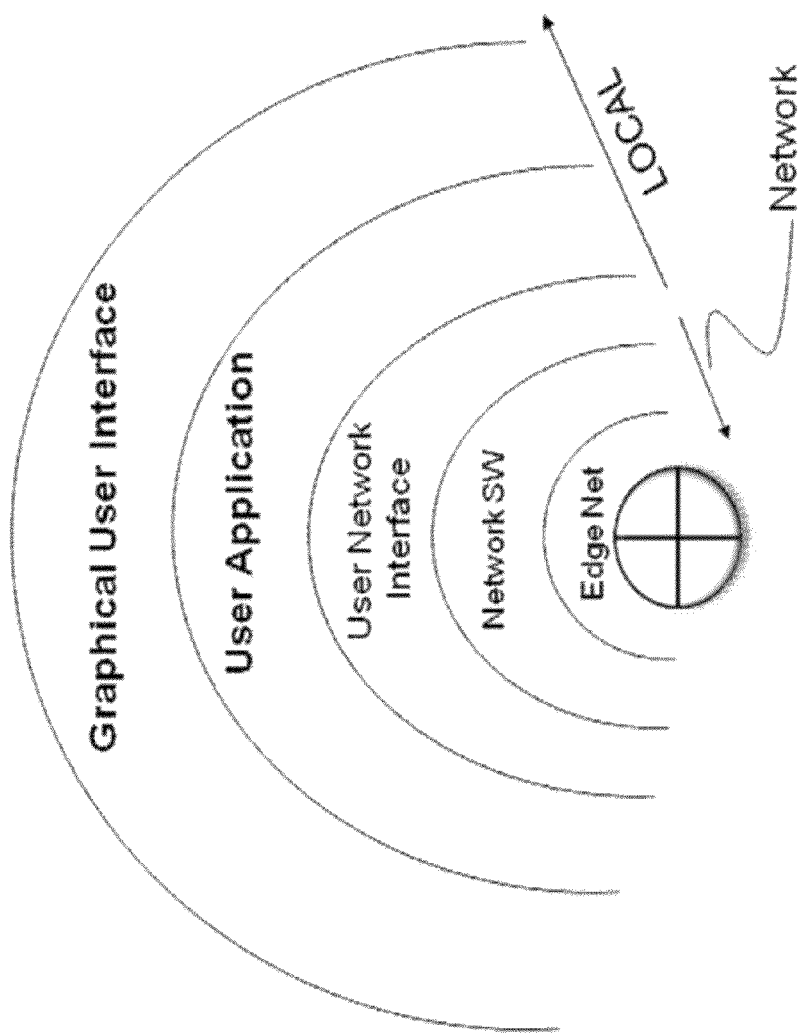
FIG. 24 provides an illustration of various functional interactions between network-based and localized applications.

Turning now to FIG. 24, an illustration is provided of various functional interactions between network-based and localized applications. The network-based applications executing on the network nodes 510 interact in a manner that allows the use of biologically-relevant information to distribute functional processing between the local processor and network processors. In response to a request message received through the graphical user interface, user application software begins performing some portion of the network-based and local processing that is required to return the desired response. The user network interface relates to the network software in such a manner that allows the network software to operate based on updated information at network nodes.

Figure 25:
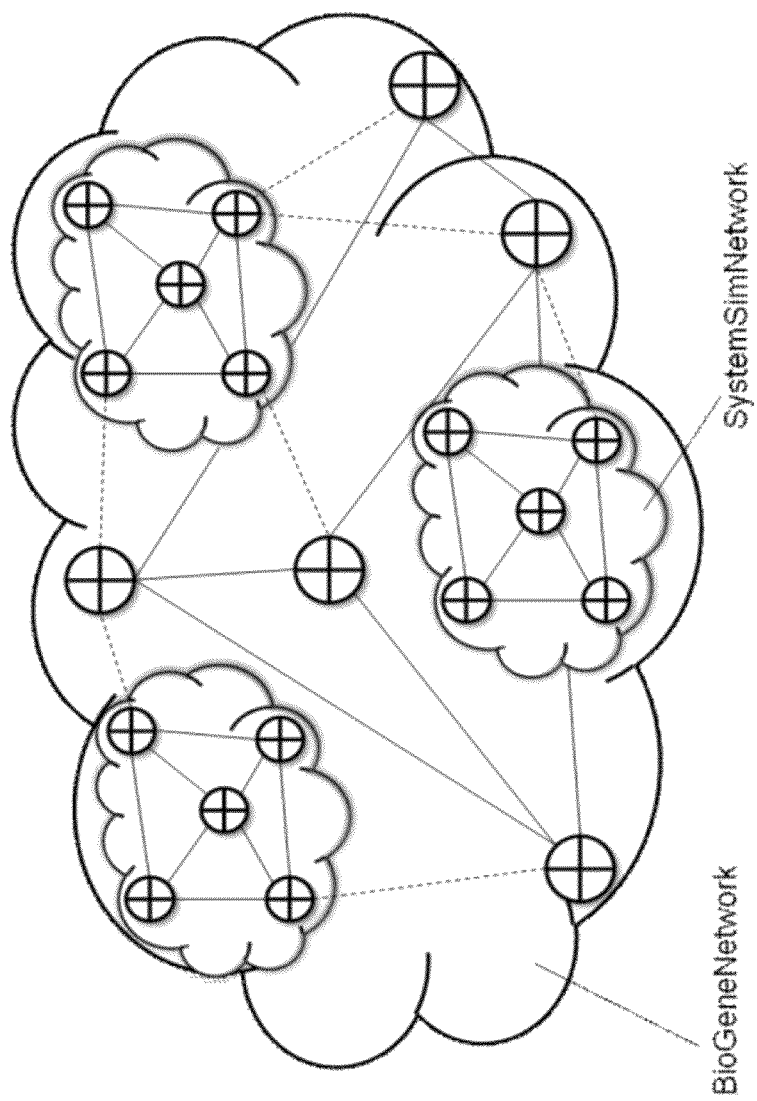
FIG. 25 depicts a biological data network which includes a collaborative simulation network.

Attention is now directed to FIG. 25, which depicts a biological data network 2500 including a collaborative simulation network 2510. In addition to the collaborative simulation network 2510, the biological data network includes a plurality of network nodes 2504. The collaborative simulation network 2510 is comprised of a plurality of processing nodes 2514.

In one embodiment the network nodes 2504 and processing nodes 2514 are structured and function in a manner substantially similar or identical to that described above with respect to the network nodes 510. In this embodiment the biological data network 2500 is implemented as an overlay network to the Internet (not shown in FIG. 25), which facilitates packetized communication between ones of the network nodes 2504 and between ones of the processing nodes 2514. As discussed below, packetized communication also occurs between certain processing nodes 2514 and network nodes 2504.

Each processing node 2514 of the collaborative simulation network 2510 is capable of performing at least one function required to process a user request or message. In one embodiment the applications executed by the collaborative simulation network 2510 are interactive and capable of distributing and coordinating processing function requirements with available updated information to return results to a user. In general, results generated at a given processing node 2514 on the collaborative simulation network 2510 are propagated to, and stored at, the other nodes 2514 of the network 2510. In addition, this data can also be made available, through one or more of the processing nodes 2514, to the network nodes 2504.

The collaborative simulation network 2510 could be used by, for example, groups such as consortia, a network of providers, at least one processing event involved in a genome sequence data analysis workflow or in connection with performance of a clinical trial. Users associated with particular processing nodes 2514 may access the processing functions and data associated with other such nodes 2514.

In one embodiment the ability of users of processing nodes 2514 to access the processing capabilities of other nodes 2514 would be controlled in accordance with an access policy. Local data that is made available on the processing nodes 2514 of the simulation network 2510 could be published or broadcast to the network nodes 2504 of the data network 2500 based upon, for example, the interests of users associated with such nodes 2504.

Although FIG. 25 depicts only one simulation network 2510 operative within the network 2500, in other embodiments multiple different simulation networks could be simultaneously functioning on the data network 2500. In this case the data types and processing functions utilized in the collaborative effort effected by each simulation network would generally be specific to each such network. For example, a particular collaboration facilitated by a given simulation network could include or involve use of, for example, image data, biomarkers including proteomic, metabolomic and transcriptomic markers, and other related data.

BioIntelligence Processing on Biological Data Networks

Figure 26:
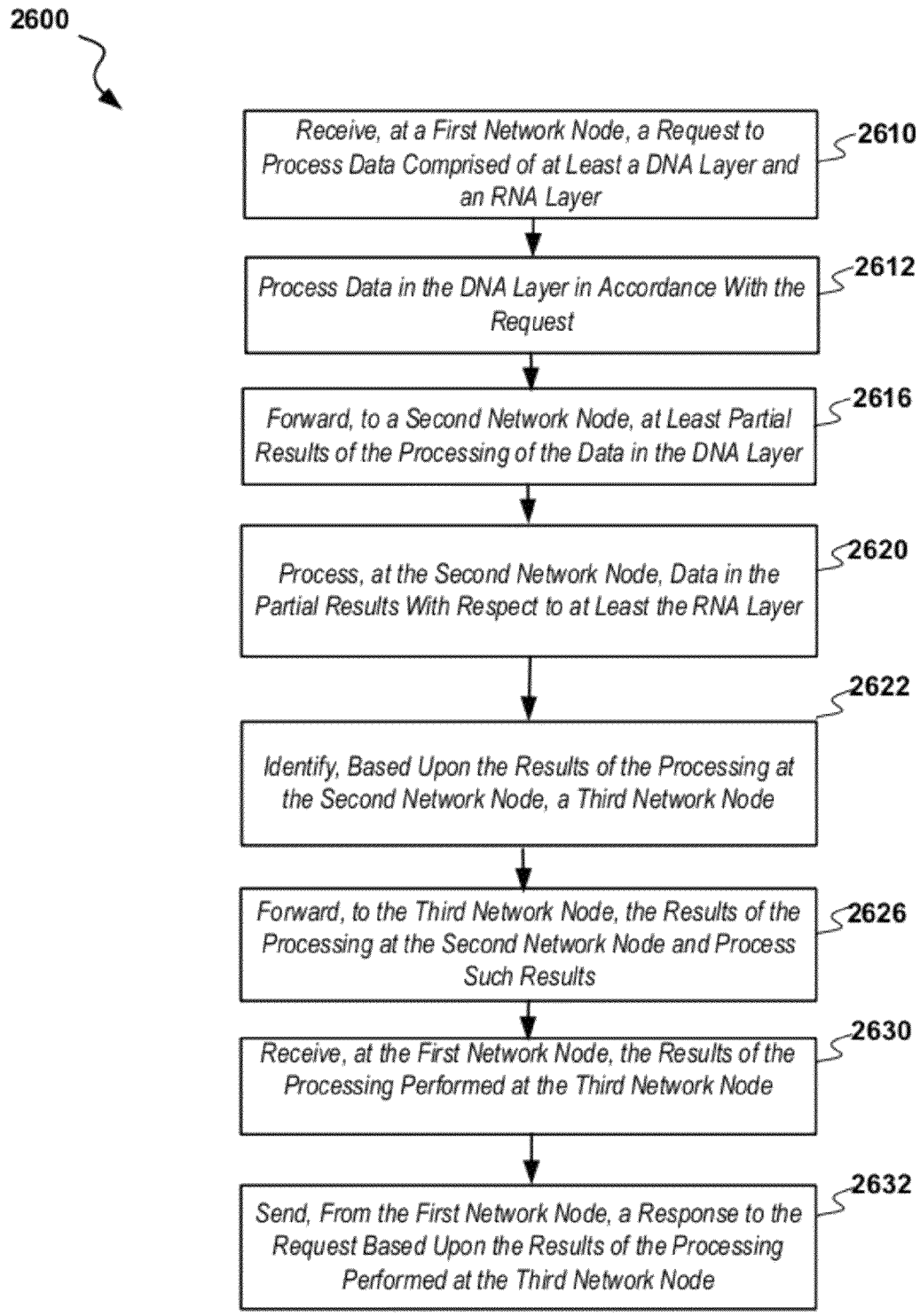
FIG. 26 is a flowchart representative of a manner in which information relating to various different layers of biologically-relevant data organized consistently with a biological data model may be processed at different network nodes.

Attention is now directed to FIG. 26, there is shown a flowchart 2600 representative of the manner in which information relating to various different layers of biologically-relevant data organized consistently with the biological data model 200 may be processed at different network nodes 510. In a stage 2610, a request to process data comprised of at least a DNA layer 210 and an RNA layer 220 is received at a first network node. Data in the DNA layer is then processed in accordance with the request (stage 2612). At least partial results of the processing of the data in the DNA layer is then forwarded to a second network node (stage 2616). Data within the partial results is then processed at the second network node with respect to at least the RNA layer (stage 2620). A third network node is then identified based upon the results of the processing at the second network node (stage 2622). The results of the processing at the second network node are then forwarded to the third network node, which then processes such results (stage 2626). The results of the processing performed at the third network node are then sent and subsequently received at the first network node (stage 2630). A response to the request is then sent from the first network node to, for example, a client terminal based upon the results of the processing performed at the third network node 510 (stage 2632).

Figure 27:
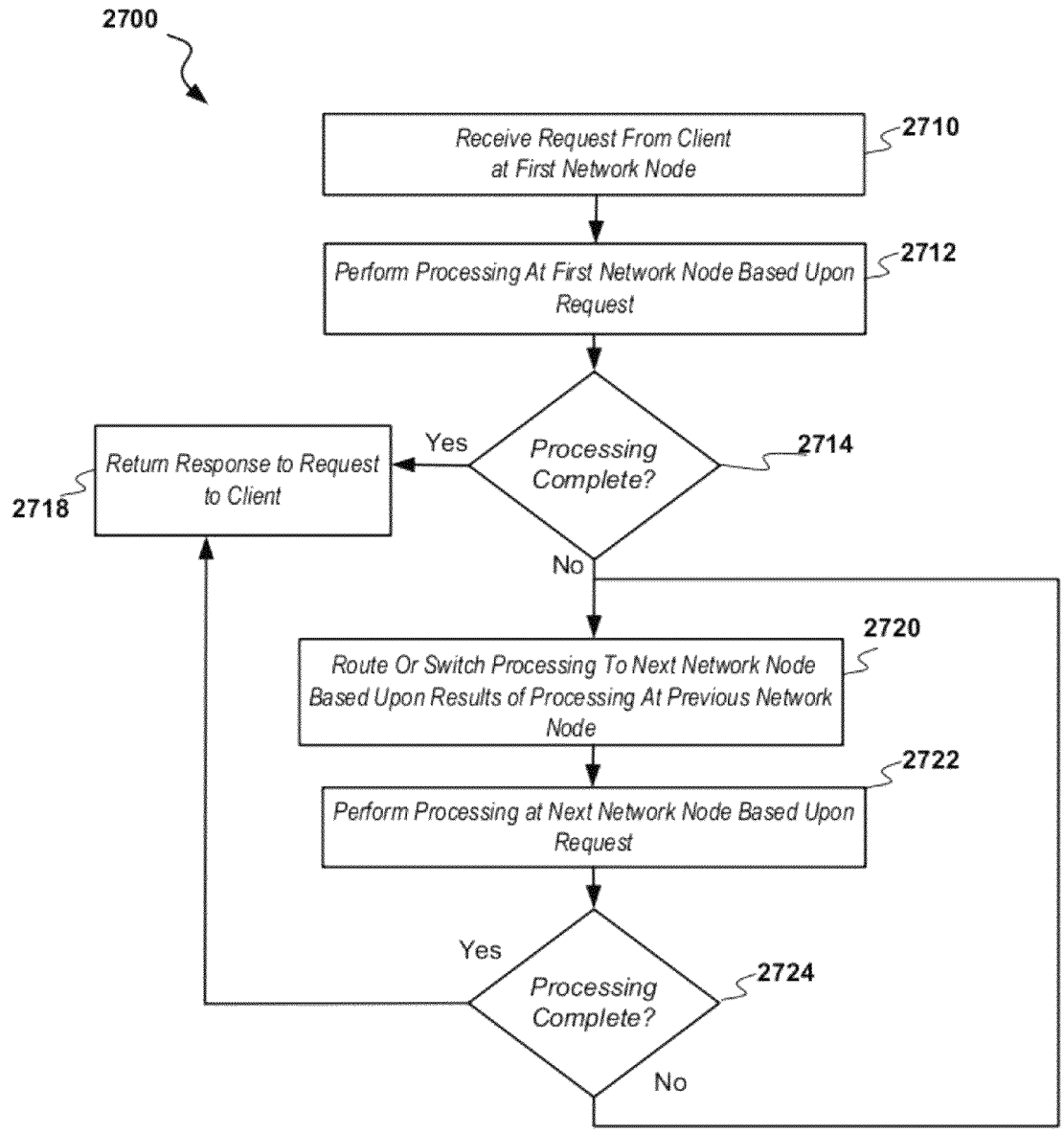
FIG. 27 is a flowchart representative of an exemplary manner in which network nodes of a biological data network may cooperate to process a client request.

Turning now to FIG. 27, a flowchart 2700 provides an overview of an exemplary manner in which network nodes 510 of the biological data network 500 may cooperate to process a client request. In stage 2710, a request is received from a client device at a first network node 510. Based upon the request, processing is performed at the first network node based upon the request (stage 2712). In stage 2714, it is determined whether processing at the first network node is complete. If such processing is complete, then an appropriate response is returned to the client (stage 2718). If not, the results of the processing at the first network node 510 may be routed or switched to a next network node 510 selected or otherwise scheduled in accordance with the nature of such processing results (stage 2720). In a stage 2722, processing is performed at the next network node based upon the request (stage 2722). It is then determined whether processing at the next network node has been completed (stage 2724). If such processing has been completed, a response is returned to the client (stage 2718); otherwise, some or all the accumulated processing results may again be routed or switched to a next network node 510 stage 2720.

Figure 28:
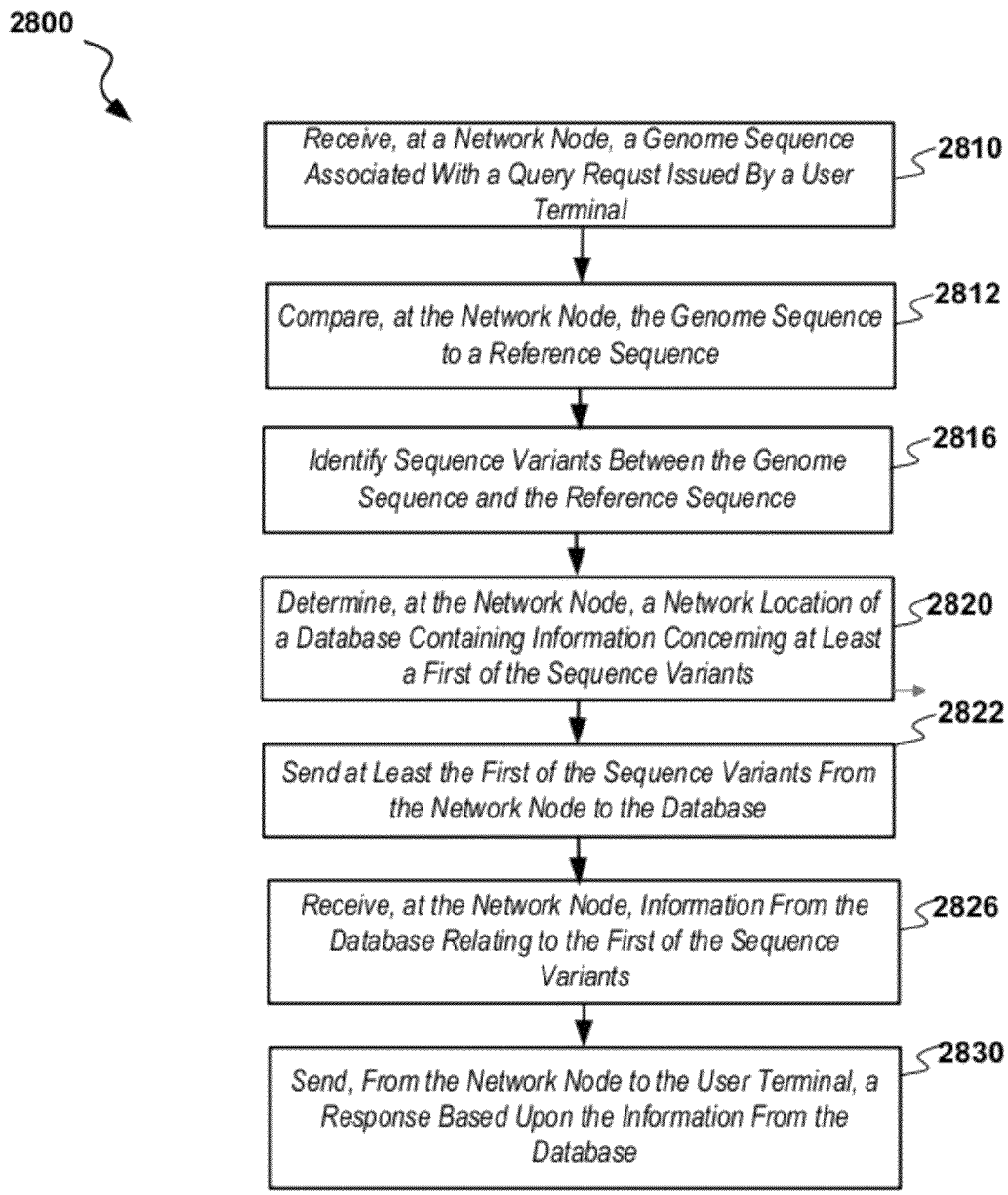
FIG. 28 is a flowchart representative of an exemplary sequence of operations involved in the identification and processing of sequence variants at a network node.

FIG. 28 is a flowchart representative of an exemplary sequence of operations involved in the identification and processing of sequence variants at a network node 510. In stage 2810, a genome sequence (e.g., a segment of the entire genome of an organism) associated with a request issued by a user terminal or other client device is received at a network node 510. The genome sequence is then compared with a reference sequence at the network node (stage 2812). Through this comparison sequence variants between the genome sequence and the reference sequence are identified (stage 2816). In a stage 2820, a network location of a database containing information concerning at least a first of the sequence variants it is determined. Next, at least the first of the sequence variants is sent from the network node to the database (stage 2822). In a stage 2826, information from the database relating to the first of the sequence variants is received at the network node (stage 2826). A response is then sent from the network node to the user terminal based upon the information from the database (stage 2830).

Figure 29:
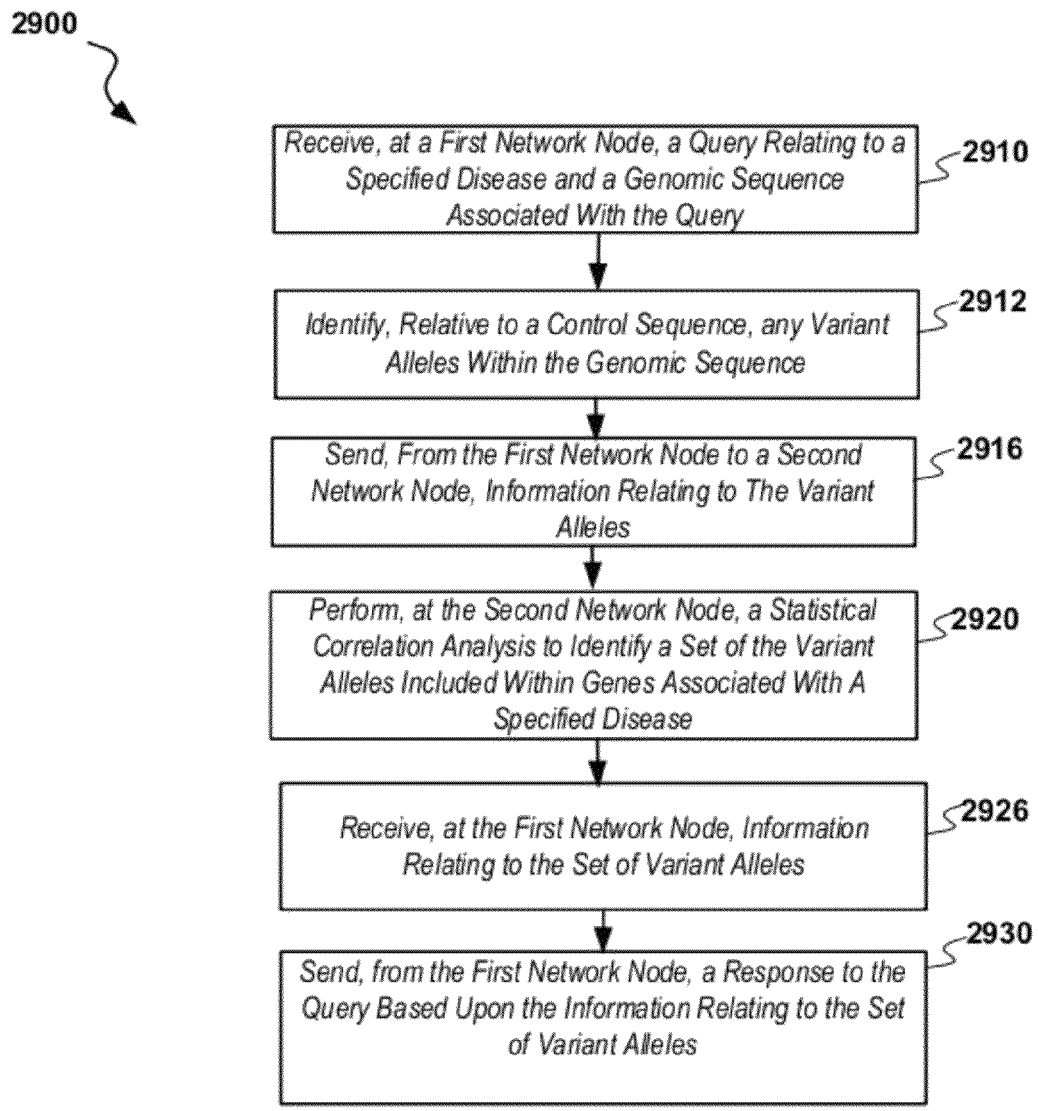
FIG. 29 is a flowchart representative of an exemplary sequence of operations carried out by network nodes of a biological data network in connection with processing of a disease-related query.

Turning now to FIG. 29, a flowchart 2900 is provided of an exemplary sequence of operations carried out by network nodes 510 of the biological data network in connection with processing of a disease-related query. In a stage 2910, a query relating to a specified disease and a genomic sequence associated with the query is received at a first network node 510 (stage 2910). Any variant alleles within the genomic sequence are then identified relative to a control sequence (stage 2912). Next, information relating to the variant alleles is sent from the first network node to a second network node (stage 2916). In a stage 2920, a statistical correlation analysis is performed at the second network node 510 in order to identify a set of the variant alleles included within genes associated with a specified disease (stage 2920). Information relating to the set of variant alleles is then received at the first network node (stage 2926). In a stage 2930, a response to the query is sent from the first network node 510 based upon the information relating to the set of variant alleles (stage 2930).

Figure 30:
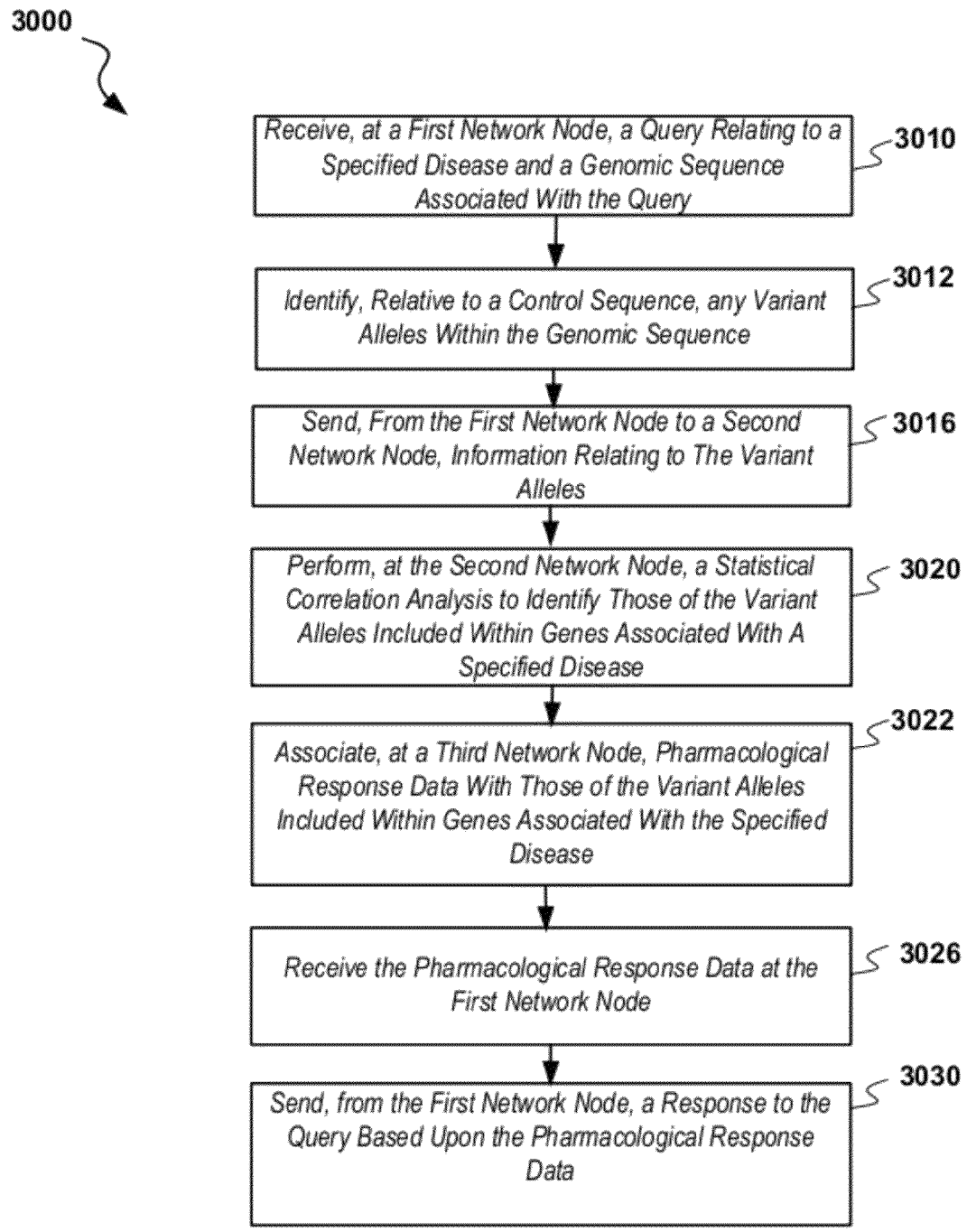
FIG. 30 is a flowchart representative of an exemplary sequence of operations involved in providing pharmacological response data in response to a user query concerning a specified disease.

Attention is now directed to FIG. 30, which is a flowchart 3000 representative of an exemplary sequence of operations involved in providing pharmacological response data in response to a user query concerning a specified disease. In a stage 3010, a query relating to a specified disease and a genomic sequence associated with the query are received at a first network node 510. Next, any variant alleles within the genomic sequence are identified relative to a control sequence. In a stage 3016, information relating to the variant alleles is sent from the first network node 510 to a second network node. A statistical correlation analysis is then performed at the second network node in order to identify those of the variant alleles included within genes associated with a specified disease (stage 3020). At a third network node 510, processing is performed to associate pharmacological response data with those of the variant alleles included within genes associated with the specified disease (stage 3022). Such pharmacological response is sent from the third network node 510 and received at the first network node (stage 3026). A response to the query is then sent from the first network node to, for example, a client terminal based upon the pharmacological response data (stage 3030).

Transmission and Reconstitution of Genome Sequence Data

Figure 31:
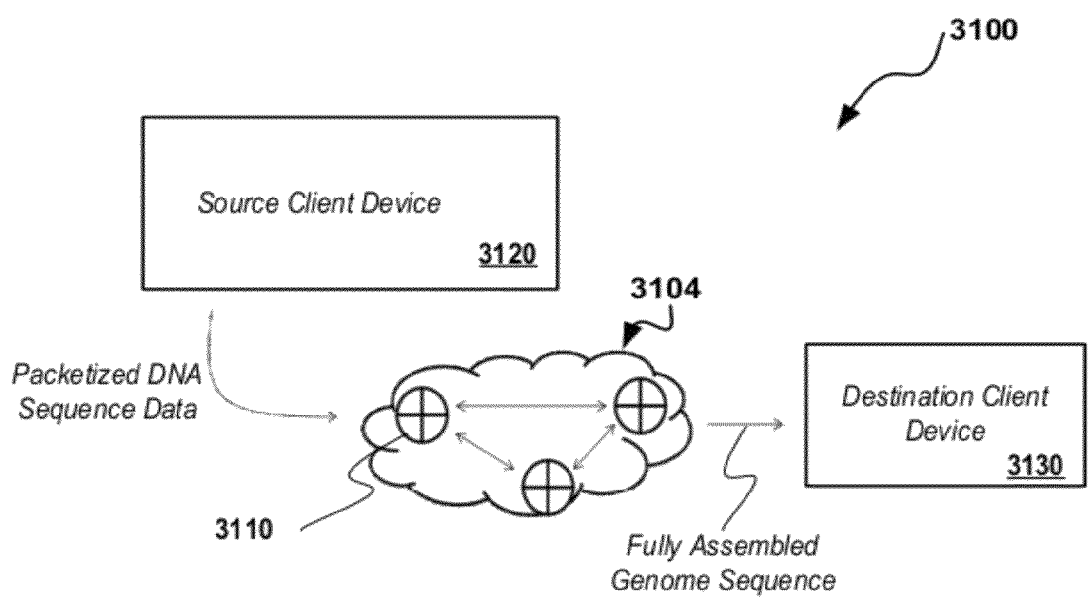
FIG. 31 illustratively represents communication of DNA sequence data or other biological sequence information between a pair of devices supporting a biological data network.

Attention is now directed to FIG. 31, to which reference will be made in describing the communication of DNA sequence data or other biological sequence information between a pair of devices supporting a biological data network 3100. In one embodiment the biological data network 3100 comprises representations of biological data linked and interrelated by an overlay network 3104 containing a plurality of network nodes 3110. In one embodiment the biological overlay network 3104 incorporates networking applications and protocols similar to those described with reference to the biological data network 1800.

As shown, the biological overlay network 3104 includes a plurality of network nodes 3110, a source client device 3120 and a destination client device 3130. In one embodiment both the source client device 3120 and the destination client device 3130 are configured to generate IP packets encapsulating biological data units comprised of one or more biologically-relevant headers and a payload including a representation of a segment biological sequence data and to provide such IP packets to a network node 3110 for distribution within the network 3100. Likewise, both the source client device 3120 and the destination client device 3130 are capable of receiving such IP packets from a network node 3110 and extracting the biologically relevant headers and payload sequence data.

In one embodiment the source client device 3120 stores or has access to DNA sequence data. Such sequence data may, for example, be accessed from storage or from a sequencing machine (not shown) configured to produce "reads" of DNA sequence data. Within the source client device 3120, the DNA sequence data may be compared to a reference sequence and represented in an instruction format in the manner described above. A plurality of biological data units may then be generated based upon segments of this sequence data and stored with in the source client device 3120. Each biological data unit will include a suitably-sized segment of DNA sequence data and a plurality of biologically-relevant headers. These biological data units may then be encapsulated with TCP/IP and/or other network protocol headers to facilitate transmission through the biological data network 3100.

The packetized biological data units sent by the source client device 3120 are routed and switched through the Internet or other network connecting the network nodes 3110 of the biological data network 3100 and delivered to the destination client device 3130. In the case in which DNA sequence data comprising an entire genome is sent by the client device 3120, the destination client device 3130 may reconstruct such genome from the packetized biological data units sent by the source client device 3120.

Load Balancing

Figure 32:
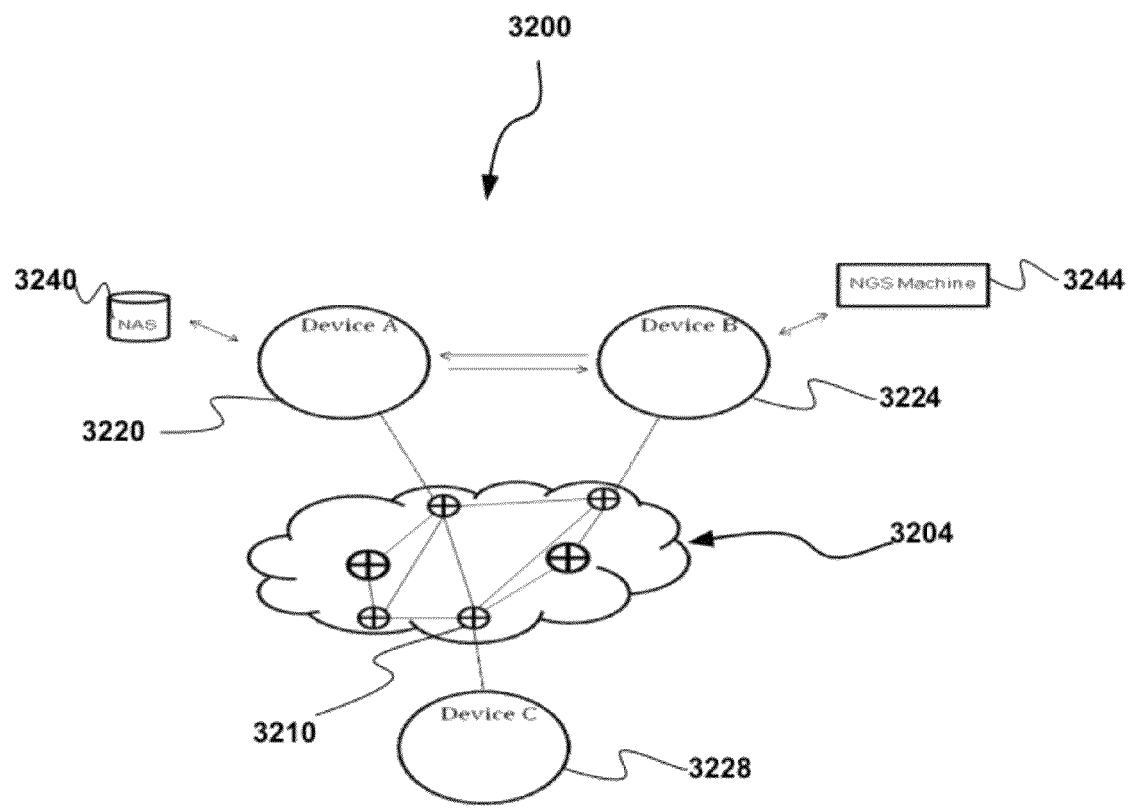
FIG. 32 illustratively represents one manner in which multiple devices may support various operations within a biological data network.

Attention is now directed to FIG. 32, to which reference will be made in describing various ways in which multiple devices supporting a biological data network 3200 may share responsibility for mapping, assembling, fragmenting, packetizing, transmitting, re-assembling and otherwise processing DNA sequence data or other biological sequence information.

In one embodiment the biological data network 3200 comprises packetized representations of biological data linked and interrelated by a biologically-relevant-data-aware overlay network 3204 containing a plurality of network nodes 3210. As is discussed below, such packetized DNA sequence data may be stored within a storage element, or may be created by directly accessing data produced by a high-throughput sequencing machine.

In the embodiment of FIG. 32, a device 3220 (i.e., device 3220 or "Device A") is associated with a network area storage element 3240. The information stored can be accessed and mapped by transmitting the data to any device having access to the BioIntelligent™ data network 3200. A device 3224 (i.e., device 3224 or "Device B") is attached to a high-throughput next generation sequencing machine 3244 and data can stream directly to the device. In this case fragments of sequences flow into the Device B, which may further divide such segments in order to generate sequence fragments of optimal length in view of the desired size of the payloads of packets used for data transport within the network 3200.

In one embodiment both Device A and Device B are configured to generate IP packets encapsulating biological data units comprised of one or more biologically-relevant headers and a payload including a representation of a segment biological sequence data and to provide such IP packets to a network node 3210 for distribution within the network 3200. Likewise, both Device A and Device B are capable of receiving such IP packets from a network node 3210 and extracting the biologically relevant headers and payload sequence data.

Packetized sequence data may be transmitted by direct networking between Device A and Device B, in which case both Device A and B have access to the machine-read data and both contain a stored copy of the reference sequence. As a result, both Device A and Device B may share the load of assembling the genome for example. Using a specific set of dynamically interactive network application and protocols, the direct connection between Devices A and B means that all of the DNA sequencing machine read data that are accessible to one device can be distributed through a local network to the second device for load sharing. One or more reference sequences used for mapping and assembly may also be shared between Device A and Device B. In one embodiment Device A and Device B are networked and able to transmit and track specific reads that have been mapped, along with the site or sites on the reference sequence that correspond to the packetized machine-read sequence.

Referring again to FIG. 32, a network-attached storage container (NAS) 3240 contains DNA sequence data in the form of raw machine-read sequences. When read size is short and sequencing has a high level of redundancy, the consensus of the redundant reads is stored. The DNA sequence reads in this storage element 3240 could have been generated from, for example, an image data-sequencing platform or direct-to-digital sequence device. In any case, the DNA sequence is packetized with BI header information that can be used to characterize such sequence in a way that allows it to be mapped to a specific region of the genome using a separately stored reference sequence. The sequence information stored within NAS 3240 need not necessarily comprise whole genome sequence data, but rather could have been generated using a method of sequence enrichment such as, for example, ChIP-Seq, RNA-Seq, ribosome profiling, and the like.

During operation, Device A is capable of accessing data from the NAS 3240. As the DNA sequence data streams into Device A from the NAS 3240, the sequence data is processed and BI header information is attached to the packetized data, thereby yielding data units that are fully recognizable by the network elements and devices, including but not limited to hardware, software, firmware, middleware, etc. In this regard the Device A may be configured to generate a biologically-relevant header for each segment of sequence data accessed from the NAS 3240 based upon the position to which such segment maps in a stored reference sequence being used for assembly. Once this mapping has been effected for each sequence segment, an entire assembled sequence (e.g., of an entire genome) may again be stored in NAS 3240.

In one embodiment the sequencing machine 3244 comprising any sequencing platform capable of generating reads of DNA sequence data. As such that reads are being generated, the sequencing machine 3244 may stream the data directly to Device B. Reads of DNA sequence data accessed from the sequencing machine 3244, or sequence segments thereof, are assigned biologically-relevant headers having one or more fields pertaining at least to the position or positions on a reference sequence corresponding to the particular read or sequence segment.

Alternatively, in order to facilitate sharing the load of mapping and assembling the reads generated by the sequencing machine 3244, Device B may forward such sequence data from the machine 3244 directly to another device, such as Device A, or to any other device operatively coupled to the network 3200.
Based upon the configuration of Device A and Device B, the reads of sequence data streamed into Device B can also be read directly by Device A. Since in this case both Device A and Device B are mapping the DNA sequence reads from a single sequencing machine 3244, the reference sequence being used by both Device A and Device B will generally be the same. In this way Device A and Device B may be configured to cooperatively share the load of mapping and assembling the reads of sequence data generated by the machine 3244.

In one embodiment Device A and Device B would implement a protocol stack developed specifically to handle such shared-mapping assembly and to effect load balancing. For example, a user could configure the devices such that Device A would be responsible for mapping sequence reads (or segments thereof) to chromosomes 1 to 10, while the sequence reads (or segments thereof) mapping to all other chromosomes could be assembled by Device B.

Considering now the processing by Device B (and/or by Device A) of reads of DNA sequence data produced by the machine 3244 by Device B, in a first stage a size of such reads is determined. If the sizes of the sequence fragments comprising such reads are determined to be too large for convenient inclusion in biological data packets, then such sequence fragments are further segmented into appropriately-sized segments. Subsequent stages in the process including aligning the incoming sequence fragments against a stored reference sequence.

Once the incoming sequence fragments or segments thereof have been properly aligned to the stored reference sequence, then biological data packets including biologically-relevant headers may be generated. Information pertaining to the alignment site (or sites) at which such sequence fragments or segments map to the reference will generally be included in the "Layer 1" header of each biological data packet. Each such Layer 1 header will also generally include other information required for the mapping and assembly of such sequence fragments or segments thereof into whole genome sequences.

Referring again to FIG. 32, another network-connected device 3228 (i.e., "Device C") may receive biological data units encapsulated within IP packets sent through the network 3200 by, for example, Device A and Device B. In one embodiment the Device C is substantially similar or identical to Device A and Device B, and may also share the load of mapping sequence fragments or segments thereof produced by sequencing machine 3244, or stored within NAS 3240, to a reference sequence. For example, sequence fragments generated by machine 3244 could be streamed over the network 3200 to Device C, which would map such sequence fragments (or segments thereof) to a stored reference sequence identical to the reference sequence utilized by Device A and/or Device B. Because the two devices are networked with a protocol suite capable of establishing a robust level of communication, communication can also be established with a third device (e.g., Device C in FIG. 32) through the existing transport and control protocols of the existing Internet.

Figure 33:
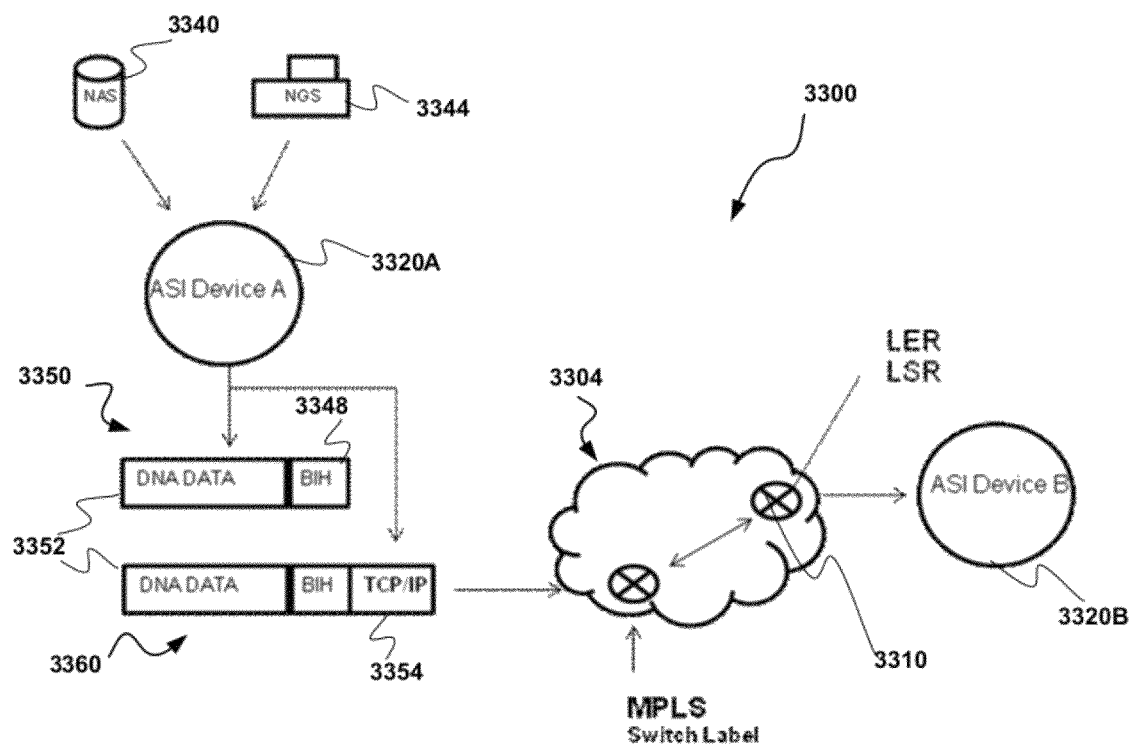
FIG. 33 illustrates a biological data network configured to utilize techniques such as, for example, multiprotocol label switching ("MPLS") to facilitate the distribution of DNA sequence data and related information between client devices.

Turning now to FIG. 33, a high-level illustration is provided of a biological data network 3300 configured to utilize techniques such as, for example, multiprotocol label switching ("MPLS") to facilitate the distribution of DNA sequence data and related information between client devices 3320. In the embodiment of FIG. 33, each client device 3320 is configured to generate IP packets encapsulating biological data units comprised of one or more biologically relevant headers and a payload including a representation of a segment biological sequence data and to provide such IP packets to a network node 3210 for distribution within the network 3300. Likewise, each client device 3320 is capable of receiving such IP packets from a network node 3310 and extracting the biologically relevant headers and payload sequence data.

In the embodiment of FIG. 33, MPLS may be utilized in edge and backbone routers to analyze IP packets and encapsulate DNA sequence data with appropriate labeling for switching. This enables service providers the ability to select particular traffic paths and supports virtual private networks with superior performance. MPLS is capable of seamlessly addressing the issue of scalability and the switch routing of DNA sequence data using a modification of existing protocol suites or newly developed protocol suites. Such DNA-based multiprotocol label switching provides a convenient "short cut" to packet routing that may be made compatible with existing protocols such as, for example, open shortest path first (OSPF) and resource reservation protocol (RSVP). Packets that will share the same transmission path will be grouped together in a label switching protocol.

As shown, device 3320A ("Device A") is associated with a network area storage element ("NAS") 3340. The information stored can be accessed and mapped by transmitting the data to any device supporting the data network 3300. Device A is also attached to a high-throughput next generation sequencing machine 3344, from which fragments of sequences are received. Device A which may further divide such segments in order to generate sequence fragments of optimal length in view of the desired size of the payloads of packets used for data transport within the network 3300 to, for example, device 3320B (i.e., "Device B").

Figure 34:
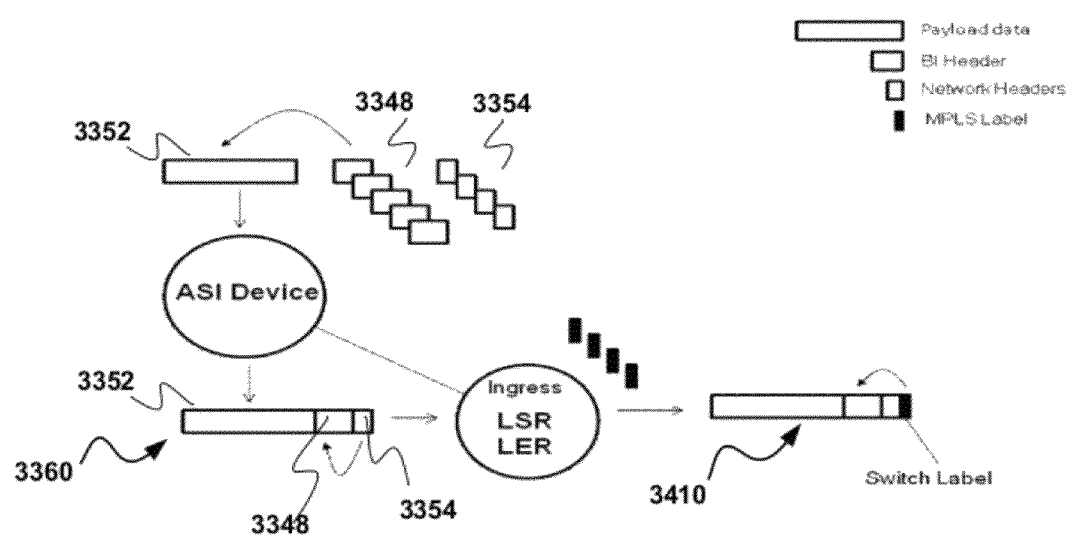
FIG. 34 illustrates a process for assigning biologically-relevant and network-related headers to segments of DNA sequence data stored within network-attached storage or received from a sequencing machine.

FIGS. 33 and 34 also illustrate the process of assigning biologically-relevant and network-related headers to segments of DNA sequence data stored within NAS 3340 or received from the sequencing machine 3344. As sequence fragments are received by Device A from either or both of the NAS 3344 and the sequencing machine 3344, biologically-relevant headers 3348 are generated and assigned and to such fragments or to segments thereof. This results in creation of biological data units 3350, each of which includes the fragment or segment of DNA sequence data 3352 with which one or more biologically-relevant headers 3348 are associated.

In one embodiment Device A is configured to determine the map site on a reference sequence as the biologically-relevant headers are assigned. Next, a specialized suite of networking protocol headers 3354 may be used to encapsulate the biological data units, thus creating network-enabled packets 3360. In one embodiment MPLS labels may also be assigned to the network-enabled packets 3360, thereby creating MPLS-labeled packets 3410 and facilitating more efficient switching through label swapping techniques.

As may be appreciated with reference to FIGS. 33 and 34, in one embodiment multiple protocol label switching is performed within a biologically-relevant-data-aware overlay network 3304. In one embodiment, label edge routers (LER) are used on the ingress side of the network 3304 to label as yet unlabeled IP packets, while the label switch routers (LSR) are used for swapping in the backbone of the network 3304. These labels may be used to assign DNA sequence data packets to a particular class for forwarding.

As a result, transmission along a predetermined path—namely, a label switch path ("LSP")—may be determined based on class, traffic, and quality of service, each of which can be controlled and maintained by the service provider. That is, based on the analysis performed at the ingress side of the network 3304, incoming IP packets encapsulating biological data units are classified, assigned the appropriate label, encapsulated in an MPLS header, and forwarded to the next stop in the LSP.

On the egress side of the network 3304, the labels are removed by LERs and packets are sent on through the network 3304 to their destination. Device B may receive the network enabled packets 3360 received transmitted over the network 3304 and extract the DNA sequence data therefrom. In the embodiment of FIG. 33 the Device B also communicates with Device A in order to determine which reference sequence (or version thereof) is being used by the Device A in order to create the representation of DNA sequence data contained within the network enabled packets 3360. With this arrangement, sequence mapping can be distributive and the load can be shared with multiple devices.

As an example of the use of MPLS labeling techniques, consider the case in which a biological data unit includes a payload comprised of a representation of DNA sequence data and an associated biologically-relevant header annotated with information on a particular gene or gene feature correlated with a particular phenotype and/or disease. In one embodiment an appropriate MPLS label could be associated with packets including such header information, which would enable such packets to be accorded a particular quality of service.

Streaming of Biological Sequence Data

Figure 35:
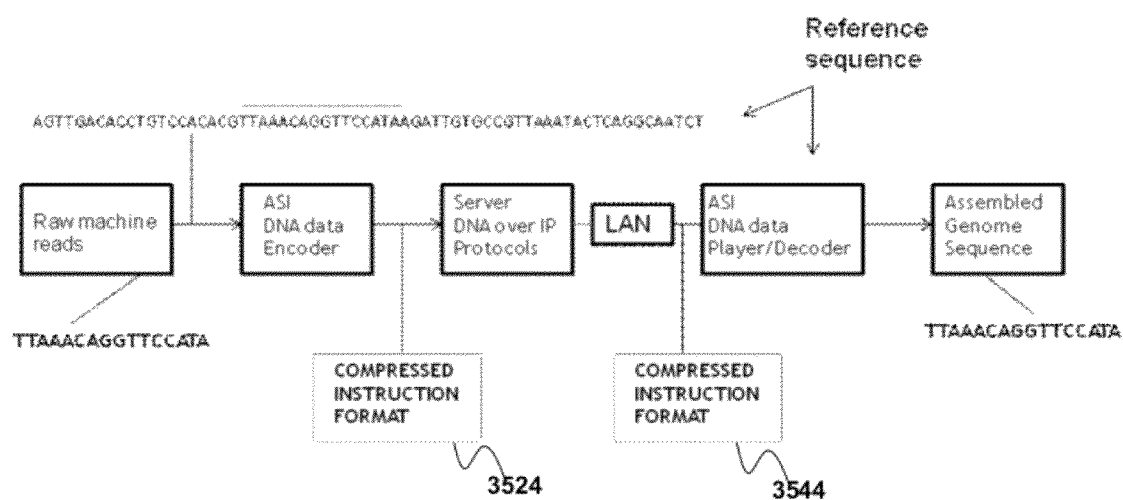
FIG. 35 illustratively represents a system and approach for using networking protocols otherwise employed for streaming media to facilitate the dissemination of DNA sequence data (SEQ ID NOS.: 2 and 3).

Referring now to FIG. 35, in one embodiment of the biological data network described herein various networking protocols otherwise employed for streaming media may be utilized to facilitate the dissemination of DNA sequence data. In a particular implementation, such networking protocols (e.g., RTP, RTSP, RTCP) are modified in order to make selecting networking devices "DNA aware". The resulting novel, specialized protocol stacks may be used to pull, in response to a request from a client application, streaming DNA sequence data from servers having access to storage containing sequence data.

In accordance with one approach, the entire human diploid genome sequence data for healthy and diseased heart, lung, and colon tissue from one individual could be transmitted with streaming packets. The DNA data in this case might stream directly from high-throughput sequencing machines to a network-enabled encoder element. The existing appliances would be able to respond to the data with specific DNA sequence data content awareness.

As the DNA data are received, the various samples and specific portions of samples can be decompressed or decoded, compared, and analyzed without the need for saving any of the data. During operation, a server streams DNA sequence data that has been encoded into a predetermined compressed file format, such as the compressed delta database format disclosed in the above-referenced copending patent applications. This format stores the DNA data as individualized encoded segments of the genome. Each biological data unit containing a segment of DNA is assigned a BioIntelligence (BI) header field that indicates the bit size of the read or segment or gene. The server parses the streaming bits of the compressed file to extract the biological data on the fly. The server sends the DNA sequence data packets to the client at periodic intervals, while the client then plays or interprets the individual encapsulated packets as they arrive from the server.

Referring to FIG. 35, sequence fragments, i.e., machine reads 3510, of any length are generated by a sequencing machine. Such sequence fragments, or segments thereof, are mapped to a reference sequence 3514 (e.g., the human genome reference sequence or an idealized reference sequence generated to optimize the process) by a data encoder 3520. The data are then converted into a compressed instruction format 3524 that is based on the reference 3514.

Compression may be carried out with no loss of information, since the reference sequence 3514 may be stored and accessible to the data encoder 3520. The DNA sequence data represented in the compressed instruction format 3524 may then be assigned biologically-relevant headers, as well as network associated headers, and the resulting encapsulated sequence information served 3530 over, for example, a DNA-aware overlay network 3534.

On the other side of the network 3534, the packets of compressed data in instruction format arrive at a receiver. In one embodiment the receiver can then decode 3540 and play the bit stream as it is being sent. One advantage of this streaming multimedia is that the DNA data can be processed and analyzed as the packets are transmitted, before the entire file is received.

After the compressed DNA sequence data 3544 in the instruction format is decoded 3540, the un-compressed read sequence can be aligned and mapped to the reference sequence. There is no loss of information due to the compression and transmission of the data. In this case, mapping of the machine-read sequences can be delocalized and assembly of the whole genome sequence 3550 can be shared among devices.

Distributed Sequence Processing, Analysis and Classification

Figure 36:
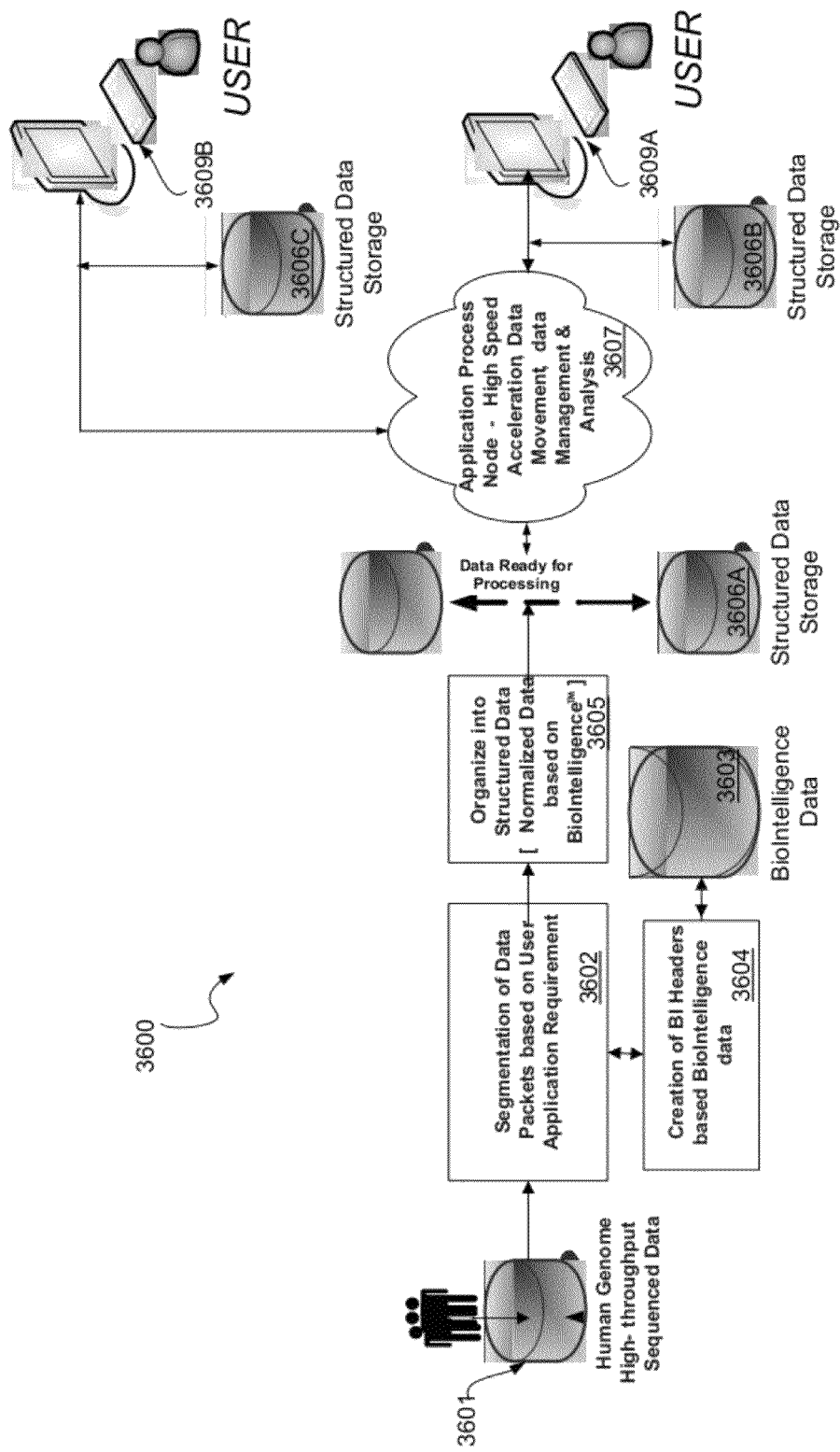
FIG. 36 is a block diagram of a high-speed sequence data analysis system.

Attention is now directed to FIG. 36, which provides a block diagram of a high-speed sequence data analysis system 3600. The analysis system 3600 may, for example, be utilized in personalized medicine applications in which genomic-based diagnosis, treatment or other services are offered. As is discussed below, the system 3600 operates to organize and represent genomic sequence data in a structured format in association with information in the manner described above. The structured data may then be further processed and delivered to end users 3606 to facilitate analysis, research and personalized medical applications. For example, the system 3600 may be configured to establish a networked arrangement among participating medical clinics in a manner enabling the provision of genomic-based diagnosis, treatment and other services.

Turning to FIG. 36, genomic data repository 3601 is representative of genomic sequence data that has been configured in accordance with standard protocols as well as newly built protocols for operating on this type of data specifically. Substantially all publicly available genomic sequence data which is currently available is provided by commonly-used genomics databases such as dbGaP, CGHub containing data for TCGA (The Cancer Genome Atlas), EMBL-Bank, DDBJ or other databases containing biological sequence information. Other sources of information represented by genomic data repository 3601 may include, for example, various sources of microarray data, gene expression data, next-generation deep sequencing data, copy number variation data, and SNP analysis data.

In a stage 3602, the accepted format for the DNA sequences from repository 3601 are segmented into multiple fragments of data sequences based upon user or application requirements. As a result, fragments or data units of DNA sequence information may be generated arbitrarily. Such fragments may include genes, introns and/or exons, regions of the genome currently referred to as "non-coding regions", or any other sequence segment relevant to a particular application.

In a stage 3604, a header comprised of data provided by storage device 3603 is assigned, associated, related or embedded with each segment of DNA sequence data, thereby forming specialized aggregates of sequence segments and attributes as biological data units. This enables the selective processing and analysis of genomic information in accordance with application requirements. For example, in the case in which a system user 3606 is an oncologist, only biological data units containing information from those genes associated or otherwise correlated with a particular cancer of interest (whether human, canine or other) are selected for processing, thereby obviating the need for inefficient processing of all of the information within data repository 3601. This selective processing is facilitated by the layered architecture of the biological data model 1400 and its implementation using headers, as discussed previously.

Similarly, if the user 3609 is a virologist, only biological data units having headers indicative of an association with viral genomic information, or with human genes or gene fragments relating to a specific viral infection, would be selected and processed.

The data within storage device 3603 may comprise any or all of the information and knowledge known to be of relevance to a particular gene. In addition, such data may also include information related to processing genes which have been fragmented into segments, and may be incorporated within headers designed to scale to accommodate future information not yet discovered or known about the particular gene or gene product or expression of that gene.

In stage 3604, the segmented genomic data is encapsulated, embedded or associated with appropriate headers to form biological data units. Further, certain fields of such headers may be further dynamically modified based upon application requirements. This may occur, for example, when genomic data is further segmented pursuant to stage 3602, which may essentially result in the generation of new headers for the associated gene. The segmented genomics data unit may then be further normalized (stage 3605) consistent with the layered data structure described herein in view of user application processing requirements. Storage devices 3606 are generally configured for storage of normalized segmented sequence data as biological data units in such a layered structure, thereby facilitating easy access based upon application requirements.

In response to requests from user applications, the data associated with biological data units stored within the devices 3606 may be processed, moved, analyzed or accelerated by one or more application processing nodes 3607 to provide services such as, for example, genomic-based diagnoses, visual exploitation of genomic studies, or research and drug discovery and development.

The user or client application desktop unit 3609 provides a mechanism to run user applications, which generate user request messages received by application processing nodes 3607 and display the data or results returned by such nodes 3607. The unit 3609 may be connected to localized ones of the processing nodes 3607 and storage elements 3606 through a local area network or the equivalent, and to remote processing and storage elements through a wide area network and/or the Internet.

The word "exemplary" is used herein to mean "serving as an example, instance, or illustration." Any embodiment described herein as "exemplary" is not necessarily to be construed as preferred or advantageous over other embodiments.

In one or more exemplary embodiments, the functions, methods and processes described may be implemented in hardware, software, firmware, or any combination thereof. If implemented in software, the functions may be stored on or encoded as one or more instructions or code on a computer-readable medium. Computer-readable media includes computer storage media. Storage media may be any available media that can be accessed by a computer.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

It is understood that the specific order or hierarchy of steps or stages in the processes and methods disclosed are examples of exemplary approaches. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both.

To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system.

Skilled artisans may implement the described functionality in varying ways for each particular application, but such implementation decisions should not be interpreted as causing a departure from the scope of the present disclosure.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Additionally, the scope of the invention includes hardware not traditionally used or thought-of having use within general purpose computing, such as graphic processing units (GPUs).

The steps or stages of a method, process or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art.

Certain of the disclosed methods may also be implemented using a computer-readable medium containing program instructions which, when executed by one or more processors, cause such processors to carry out operations corresponding to the disclosed methods.

An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein. It is intended that the following claims and their equivalents define the scope of the disclosure.

We claim:

1. A network node, comprising:
a data container including a plurality of biological data units, each of the plurality of biological data units including:
a payload containing biological sequence data,
a first BioIntelligent™ header associated with biological information relating to biological sequence data wherein the first BioIntelligent™ header identifies a first biological characteristic associated with a first subset of the biological sequence data, and
a second BioIntelligent™ header identifying a second biological characteristic associated with a second subset of the biological sequence data;
a processor configured to identify, in response to a query received by the network node, at least one of the first BioIntelligent™ header and the second BioIntelligent™ header associated with a first of the plurality of biological data units wherein the first of the plurality biological data units includes first sequence data;
a packet generator configured to generate a data packet associated with the first sequence data, the data packet including a first header containing network routing information relating to a network communications protocol and a second header associated with a layered model different from the network communications protocol wherein the layered model is representative of the biological sequence data and wherein the second header is the at least one of the first BioIntelligent™ header and the second BioIntelligent™ header and is different from the first sequence data;
a queue communicatively coupled to the packet generator, the queue storing the data packet; and
a transmit controller for controlling transmission of the data packet to a node of a network.

2. The network node of claim 1 wherein the packet generator is further configured to generate a third header and wherein the second header is associated with a first layer of the layered model and the third header is associated with a second layer of the layered model.

3. The network node of claim 2 wherein the first layer comprises a DNA-specific layer and the second layer comprises an RNA-specific layer.

4. The network node of claim 3 wherein the second header information pertains to a characteristic of DNA and the third header information pertains to a characteristic of RNA.

5. The network node of claim 3 wherein the packet generator is further configured to generate a fourth header and wherein the fourth header is associated with a third layer of the layered representation of biological sequence data.

6. The network node of claim 5 wherein the third layer comprises a protein-specific layer.

7. The network node of claim 1 wherein the biological sequence data comprises polymeric data.

8. The network node of claim 1 wherein the biological sequence data comprises DNA sequence data.

9. The network node of claim 1 wherein the biological sequence data comprises genomic sequence data.

10. The network node of claim 1 wherein the second header is associated with biological information.

11. The network node of claim 10 wherein the biological information identifies one or more portions of the biological sequence data associated with a disease condition.

12. The network node of claim 11 wherein the biological information comprises one or more characteristics of the biological sequence data.

13. The network node of claim 12 wherein the biological sequence data comprises a segment of DNA sequence data.

14. The network node of claim 13 wherein the one or more characteristics relate to a property of the segment of DNA sequence data.

15. The network node of claim 14 wherein the property comprises a number of exons included within the segment of DNA sequence data.

16. The network node of claim 14 wherein the property comprises locations of exons included within the segment of DNA sequence data.

17. The network node of claim 14 wherein the property relates to an extent of methylation within the segment of DNA sequence data.

18. The network node of claim 14 wherein the property comprises one or more molecular pathways associated with the segment of DNA sequence data.

19. The network node of claim 14 wherein the property relates to one or more gene mutations within the segment of DNA sequence data.

20. The network node of claim 1 wherein the queue includes other data packets to be transmitted.

21. The network node of claim 1 wherein the generating further includes generating a third header containing metadata associated with a different subset of the sequence data.

22. The network node of claim 1 wherein the generating the third header includes identifying an additional biological characteristic associated with the subset of the sequence data wherein a biological relationship exists between second header information included within the second header and third header information included within the third header.

23. A network node, comprising:
a data container including a plurality of biological data units, each of the plurality of biological data units including:
a payload containing biological sequence data,
a first BioIntelligent™ header associated with biological information relating to biological sequence data wherein the first BioIntelligent™ header identifies a first biological characteristic associated with a first subset of the biological sequence data, and
a second BioIntelligent™ header identifying a second biological characteristic associated with a second subset of the biological sequence data;
a processor configured to evaluate, in response to a query received by the network node, headers of the plurality of biological data units in order to identify at least one of the first BioIntelligent™ header and the second BioIntelligent™ header associated with a first of the plurality of biological data units wherein the first of the plurality biological data units includes first sequence data;

a packet generator configured to generate a data packet associated with the first sequence data, the data packet including a first header containing network routing information relating to a network communications protocol and a second header associated with a layered model different from the network communications protocol wherein the layered model is representative of biological sequence data wherein the second header is the at least one of the first BioIntelligent™ header and the second BioIntelligent™ header and is different from the first sequence data;

a queue communicatively coupled to the packet generator, the queue storing the data packet; and a transmit controller for controlling transmission of the data packet to another node of a network;

a network interface configured to receive a data packet including a first header containing network routing information and a second header associated with a layered model representative of the biological sequence data; and a processing module communicatively coupled to the network interface, the processing module parsing the data packet and separating the first header from the second header.

24. The network node of claim 23 wherein the queue includes other data packets to be transmitted.

25. The network node of claim 23 wherein the packet generator is further configured to generate a third header containing metadata associated with a different subset of the sequence data.

* * * * *